United States Patent
Wan et al.

(10) Patent No.: US 11,851,431 B2
(45) Date of Patent: Dec. 26, 2023

(54) TRICYCLIC JANUS KINASE 1 INHIBITORS, AND COMPOSITIONS AND METHODS THEREOF

(71) Applicant: LYNK PHARMACEUTICALS CO. LTD., Zhejiang (CN)

(72) Inventors: Zhaokui Wan, Hangzhou (CN); Michael Lawrence Vazquez, Hangzhou (CN)

(73) Assignee: LYNK PHARMACEUTICALS CO. LTD., Hangzhou (CN)

( * ) Notice: Subject to any disclaimer, the term of this patent is extended or adjusted under 35 U.S.C. 154(b) by 0 days.

(21) Appl. No.: 18/217,037

(22) Filed: Jun. 30, 2023

(65) Prior Publication Data

US 2023/0339950 A1 Oct. 26, 2023

Related U.S. Application Data

(63) Continuation of application No. 17/289,584, filed as application No. PCT/CN2019/115069 on Nov. 1, 2019.

(60) Provisional application No. 62/754,029, filed on Nov. 1, 2018.

(51) Int. Cl.
*C07D 471/14* (2006.01)
*A61K 31/437* (2006.01)

(52) U.S. Cl.
CPC .................. *C07D 471/14* (2013.01)

(58) Field of Classification Search
CPC ........................ C07D 471/14; A61K 31/437
USPC ............................ 546/82; 514/293
See application file for complete search history.

(56) References Cited

U.S. PATENT DOCUMENTS

| 8,426,411 | B2 | 4/2013 | Wishart et al. |
| RE47,221 | E | 2/2019 | Wishart et al. |
| 2009/0312338 | A1 | 12/2009 | Wishart et al. |
| 2013/0216497 | A1 | 8/2013 | Wishart et al. |
| 2016/0222020 | A1 | 8/2016 | Wishart et al. |

FOREIGN PATENT DOCUMENTS

| CN | 102118968 A | 7/2011 |
| CN | 102712640 A | 10/2012 |
| EP | 2924026 A1 | 9/2015 |
| WO | 2011068881 A1 | 6/2011 |
| WO | WO-2013007765 A1 | 1/2013 |

OTHER PUBLICATIONS

Kulagowski Janusz J. et al. "Identification of Imidazo-Pyrrolopyridines as Novel and Potent JAK1 Inhibitors" Journal of Medicinal Chemistry, vol. 55. No. 12. May 16, 2012, pp. 5901-5921.
Mark Zak et al. "Discovery and Optimization of C-2 Methyl Imidazopyrrolopyridines as Potent and Orally Bioavailable JAK1 Inhibitors with Selectivity over JAK2" Journal of Medicinal Chemistry, vol. 55. No. 13. Jun. 14, 2012, pp. 6176-6193.
Itteboina Ramesh et al. "Molecular docking, 3D QSAR and dynamics simulation studies of imidazo-pyrrolopyridines as janus kinase 1 (JAK 1) inhibitors" Computational Biology and Chemistry, vol. 64, May 16, 2016, pp. 33-46.
International Search Report for PCT/CN2019/115069 dated Jan. 23, 2020.
Written Opinion of the International Searching Authority for PCT/CN2019/115069 dated Jan. 23, 2020.

*Primary Examiner* — Charanjit Aulakh
(74) *Attorney, Agent, or Firm* — Milstein Zhang & Wu LLC

(57) ABSTRACT

The invention provides a novel class of therapeutics that are safe and effective inhibitors of Janus kinase 1 and pharmaceutical composition and methods of preparation and use thereof in the treatment of various diseases and disorders (e.g., inflammatory diseases, immune-mediated diseases or cancer).

8 Claims, No Drawings

TRICYCLIC JANUS KINASE 1 INHIBITORS, AND COMPOSITIONS AND METHODS THEREOF

PRIORITY CLAIMS AND RELATED PATENT APPLICATIONS

This application is a continuation of and claims the benefit of priority to U.S. Utility application Ser. No. 17/289,584, filed Apr. 28, 2021, which is a § 371 National Stage Application of PCT/CN2019/115069, filed Nov. 1, 2019, which claims the benefit of priority to U.S. Provisional Application Ser. No. 62/754,029, filed on Nov. 1, 2018, the entire content of which is incorporated herein by reference for all purposes.

PRIORITY CLAIMS AND RELATED PATENT APPLICATIONS

This application claims the benefit of priority to U.S. Provisional Application Ser. No. 62/754,029, filed on Nov. 1, 2018, the entire content of which is incorporated herein by reference.

TECHNICAL FIELDS OF THE INVENTION

The invention generally relates to novel compounds and methods for their therapeutic use. More particularly, the invention relates to a novel class of therapeutics that are safe and effective inhibitors of Janus kinase 1. The invention also relates to pharmaceutical compositions of these compounds and methods of their preparation and use in the treatment of various diseases and disorders (e.g., inflammatory diseases, immune-mediated diseases or cancer).

BACKGROUND OF THE INVENTION

Janus kinase (JAK) is a family of intracellular, nonreceptor tyrosine kinases that transduce cytokine-mediated signals via the Janus kinase—Signal Transduction Activators of Transcription (JAK-STAT) pathway. There are four members in the JAK family of enzymes in humans, i.e., JAK1, JAK2, JAK3 and TYK2. The family is defined by the presence of two adjacent kinase domains, JH1 and JH2, of which JH1 performs the phosphorylation involved in pathway activation whereas JH2 regulates JH1 function. (Thomas, et al., 2015 *British Journal of Cancer* 113, 365-371.)

These cytoplasmic tyrosine kinases are associated with membrane cytokine receptors such as common gamma-chain receptors and the glycoprotein 130 (gp130) transmembrane proteins. (Murray, et sl. 2007 *Immunol.* 178(5):2623-2629.) About 40 cytokine receptors signal through combinations of these four JAKs and their 7 downstream substrates: the STAT family members. (Ghoreschi et al. 2009 *Immunol Rev.* 228(1):273-287.)

The JAK-STAT signaling pathway plays a major role in many fundamental biological processes, such as apoptosis and inflammation via communication of chemical signals outside of a cell to the cell nucleus, resulting in the activation of genes through transcription. A dysfunctional JAK-STAT pathway may lead to a number of diseases, such as cancer and diseases affecting the immune system.

JAK1 and JAK3 are components of the common gamma-chain cytokine receptor complexes, and blockade of either inhibits signaling by inflammatory cytokines: Interleukin (IL)-2, 4, 7, 9, 15, and 21. (Ghoreschi et al. 2009 *Immunol Rev.* 228(1):273-287.) By contrast, other pathologically relevant cytokines, such as IL-6, depend uniquely on JAK1 (Guschin et al., *EMBO J.* 14(7): 1421-1429, 1995) and clinical efficacy in rheumatoid arthritis has been demonstrated by blocking IL-6 with the IL-6 receptor neutralizing antibody, tocilizumab. (Maini et al. 2006 *Arthritis Rheum.* 54(9):28 17-2829.)

Previous studies have shown that JAK1 is required for the development, function and homeostasis of the immune system and JAK1 deficiency is perinatally lethal. (Schindler, et al. 2007 *J Biol Chem.* 282(28):20059-20063.) JAK2 deficiency in mice also is lethal, with JAK2 embryos dying between Day 12 and Day 13 after conception because of deficits in erythropoiesis. (Neubauer et al. 1998 *Cell* 93(3): 397-409.) JAK3 deficiency has been described in humans and presents as severe combined immunodeficiency in the first few months of life, with symptoms such as failure to thrive, severe and recurrent infections, thrush, and diarrhea. Infants with JAK3 deficiency have an absence of circulating T cells and NK cells and abnormal B cell function. TYK2-deficiency additionally has been described in humans, manifesting with impaired antimicrobial responses, elevated serum IgE, and atopic dermatitis (Minegishi, et al, 2006 *Immunity* 25(5):745-755.)

Anti-cytokine therapies have become standard in the treatment of rheumatoid arthritis and other autoimmune disorders. Multiple clinical trials have demonstrated statistically significant efficacy in rheumatoid arthritis, psoriatic arthritis and ulcerative colitis. (Kremer, et al. 2009 *Arthritis Rheum.* 60(7):1895-1905; Riese, et al. 2010 *Best Pract. Res. Clin. Rheumatol.* 24(4):5 13-526; Fleischmann, et al., Safety and efficacy of baricitinib in elderly patients with rheumatoid arthritis. RMD Open 2017; 3:e000546.)

Despite diverse treatment options, many patients with autoimmune diseases fail to experience substantial decreases in disease activities. Although studies have shown that JAK blockade may be effective in managing disease and achieving remission, the first generation JAK inhibitors (such as tofacitinib and baricitinib) have failed to reach their full potential, at least in part due to their tolerability and safety issues that limit dose. (Fleischmann et al, *Curr. Opin. Rheumatol.* 24:335-341, 2012; Riese et al, *Best Pract. Res. Clin. Rheumatol.* 24:513-526, 2010.) Even with the high selectivity of these two compounds for JAKs over other kinase families, these inhibitors may not be optimally selective for kinases within the JAK family. These effects could arise due to inhibition of EPO and IL-15 signaling via JAK2 and JAK3 respectively. (Jost, et al. 2013 *Annu. Rev. Immunol.* 31:163-194; Kennedy, et al. 2000 *J. Exp. Med.* 191: 771-780; Richmond, et al. 2005 *Trends Cell Biol.* 15:146-155.) Modulation of immune activity through inhibition of JAK1 kinase activity can prove useful in the treatment of various immune disorders while avoiding JAK2 dependent erythropoietin (EPO) and thrombopoietin (TPO) signaling. (Murray 2007 *J. Immunol.* 178, 2623-2629; Kisseleva, et al. 2002 *Gene,* 285, 1-24; O'Shea, et al. 2002 *Cell* 109, S121S 131; Neubauer, et al. 1998 *Cell* 93(3), 397-409; Parganas, et al. 1998 Cell 93(3), 385-95.)

Thus, notwithstanding current treatment options for inflammatory diseases, immune-mediated diseases or cancer and other diseases associated with JAK1, there remains an urgent unmet need for novel JAK1 inhibitors having improved potency and selectivity with less side effects than existing therapeutics.

SUMMARY OF THE INVENTION

The invention provides a series of novel, orally and/or topically available, selective and potent JAK1 inhibitors that have improved safety and/or efficacy profiles than currently available therapeutics. The invention also provides pharmaceutical compositions of these compounds and methods of their preparation and therapeutic use.

In one aspect, the invention generally relates to a compound having the structural formula (I):

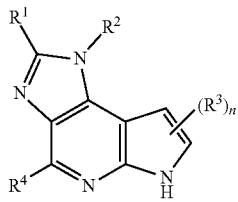

(I)

wherein
- $R^1$ is selected from hydrogen, $C_1$-$C_6$ (e.g., $C_1$-$C_3$) unsubstituted or substituted alkyl, OR', COOR' and CONR'R";
- $R^2$ is selected from $C_3$-$C_{10}$ (e.g., $C_3$-$C_6$) cycloalkyl, bicycloalkyl, spirocyclic or bridgedcycloalkyl, substituted with NR'C(=O)$R^x$, NR'C(=O)O$R^x$, NR'C(=O)NR$^x$R$^y$, C(=O)NR$^x$R$^y$, NR'SO$_2$R$^x$, NR'SO$_2$NR$^x$R$^y$, CR'R"SO$_2$R' or CR'R"SO$_2$NR$^x$R$^y$;
- each $R^3$ is independently selected from hydrogen, $C_1$-$C_6$ (e.g., $C_1$-$C_3$) unsubstituted or substituted alkyl, OR', COOR' and CONR'R";
- $R^4$ is a group selected from hydrogen, halogen, CN, $C_1$-$C_6$ (e.g., $C_1$-$C_3$) unsubstituted or substituted alkyl, OR', and NHR';
- each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and $R^x$ and $R^y$ may together form a 3- to 7-membered (e.g., 3- or 4-membered) ring, and each of $R^x$ and $R^y$ is optionally substituted with one or more of halogen (e.g., F, Cl), CN, OR', NR'R", alkyl (e.g., $C_1$-$C_6$ alkyl), haloalkyl (e.g., CHF$_2$, CF$_3$), cyanoalkyl (e.g., CH$_2$CN), hydroxyalkyl (e.g., CH$_2$OH) and alkoxyalkyl (e.g., CH$_2$O-alkyl); each of R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and
- n is 1 or 2, or a pharmaceutically acceptable form or an isotope derivative thereof.

In another aspect, the invention generally relates to a compound having the structural formula (VII):

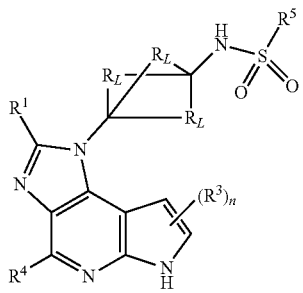

(VII)

wherein
- $R^1$ is selected from hydrogen, $C_1$-$C_6$ (e.g., $C_1$-$C_3$) unsubstituted or substituted alkyl, OR', COOR' and CONR'R";
- each $R^3$ is independently selected from hydrogen, $C_1$-$C_6$ (e.g., $C_1$-$C_3$) unsubstituted or substituted alkyl, OR', COOR' and CONR'R";
- $R^4$ is a group selected from hydrogen (e.g., F, Cl), halogen, CN, $C_1$-$C_6$ (e.g., $C_1$-$C_3$) unsubstituted or substituted alkyl, OR', and NHR';
- $R^5$ is $R^x$ or NR$^x$R$^Y$, wherein each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and $R^x$ and $R^y$ may together form a 3- to 7-membered (e.g., 3- or 4-membered) ring, and each of $R^x$ and $R^y$ is optionally substituted with one or more of halogen (e.g., F, Cl), CN, OR', NR'R", alkyl (e.g., $C_1$-$C_6$ alkyl), haloalkyl (e.g., CHF$_2$, CF$_3$), cyanoalkyl (e.g., CH$_2$CN), hydroxyalkyl (e.g., CH$_2$OH) and alkoxyalkyl (e.g., CH$_2$O-alkyl); provided that when $R^5$ is $R^x$, $R^x$ is not H (i.e., $R^5$ is not H);
- each $R_L$ is independently (CH$_2$)$_m$ and m is independently 0, 1, 2 or 3, wherein when m is 0, the respective bridge is absent;
- each R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and
- n is 1 or 2, or a pharmaceutically acceptable form or an isotope derivative thereof.

In yet another aspect, the invention generally relates to a pharmaceutical composition comprising a compound according to the herein disclosed invention, effective to treat or reduce one or more diseases or disorders, in a mammal, including a human, and a pharmaceutically acceptable excipient, carrier, or diluent.

In yet another aspect, the invention generally relates to a pharmaceutical composition comprising a compound having the structural formula (I):

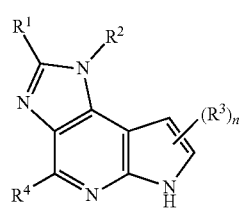

(I)

wherein
- $R^1$ is selected from hydrogen, $C_1$-$C_6$ unsubstituted or substituted alkyl, OR', COOR' and CONR'R";
- $R^2$ is selected from $C_3$-$C_{10}$ cycloalkyl, bicycloalkyl, spirocyclic or bridgedcycloalkyl, substituted with NR'C(=O)$R^x$, NR'C(=O)O$R^x$, NR'C(=O)NR$^x$R$^y$, C(=O)NR$^x$R$^y$, NR'SO$_2$R$^x$, NR'SO$_2$NR$^x$R$^Y$, CR'R" SO$_2$R$^x$ or CR'R" SO$_2$NR$^x$R$^y$;
- each $R^3$ is independently selected from hydrogen, $C_1$-$C_6$ unsubstituted or substituted alkyl, OR', COOR' and CONR'R";
- $R^4$ is a group selected from hydrogen, halogen, CN, $C_1$-$C_6$ unsubstituted or substituted alkyl, OR', and NHR';

each of R<sup>x</sup> and R<sup>y</sup> is independently selected from H, alkyl, cycloalkyl, heterocycloalkyl, aryl, heteroaryl and R<sup>x</sup> and R<sup>y</sup> may together form a 3- to 7-membered ring, and each of R<sup>x</sup> and R<sup>y</sup> is optionally substituted with one or more of halogen, CN, OR', NR'R", alkyl, haloalkyl, cyanoalkyl, hydroxyalkyl and alkoxyalkyl;

each of R' and R" is independently selected from hydrogen and $C_1$-$C_6$ unsubstituted and substituted alkyl and R' and R" may together form a 3- to 7-membered ring; and n is 1 or 2, or a pharmaceutically acceptable form or an isotope derivative thereof, and a pharmaceutically acceptable excipient, carrier, or diluent.

In yet another aspect, the invention generally relates to a pharmaceutical composition comprising a compound having the structural formula (VII):

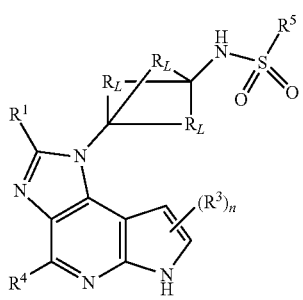

(VII)

wherein $R^1$ is selected from hydrogen, $C_1$-$C_6$ unsubstituted or substituted alkyl, OR', COOR' and CONR'R";

each $R^3$ is independently selected from hydrogen, $C_1$-$C_6$ unsubstituted or substituted alkyl, OR', COOR' and CONR'R";

$R^4$ is a group selected from hydrogen, halogen, CN, $C_1$-$C_6$ unsubstituted or substituted alkyl, OR', and NHR';

$R^5$ is $R^x$ or $NR^xR^y$, wherein each of $R^x$ and $R^y$ is independently selected from H, alkyl, cycloalkyl, heterocycloalkyl, aryl, heteroaryl and $R^x$ and $R^y$ may together form a 3- to 7-membered ring, and each of $R^x$ and $R^y$ is optionally substituted with one or more of halogen, CN, OR', NR'R", alkyl, haloalkyl, cyanoalkyl, hydroxyalkyl and alkoxyalkyl; provided that when $R^5$ is $R^x$, $R^x$ is not H;

each $R_L$ is independently $(CH_2)_m$ and m is independently 0, 1, 2 or 3, wherein when m is 0, the respective bridge is absent;

each R' and R" is independently selected from hydrogen and $C_1$-$C_6$ unsubstituted and substituted alkyl and R' and R" may together form a 3- to 7-membered ring; and n is 1 or 2, or a pharmaceutically acceptable form or an isotope derivative thereof, and a pharmaceutically acceptable excipient, carrier, or diluent.

In yet another aspect, the invention generally relates to a method for treating or reducing a disease or disorder, comprising: administering to a subject in need thereof a pharmaceutical composition comprising a compound having the structural formula (I):

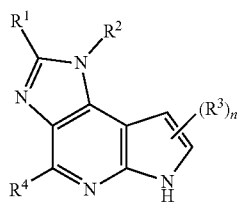

(I)

wherein $R^1$ is selected from hydrogen, $C_1$-$C_6$ unsubstituted or substituted alkyl, OR', COOR' and CONR'R";

$R^2$ is selected from $C_3$-$C_{10}$ cycloalkyl, bicycloalkyl, spirocyclic or bridgedcycloalkyl, substituted with NR'C(=O)R<sup>x</sup>, NR'C(=O)OR<sup>x</sup>, NR'C(=O)NR<sup>x</sup>R<sup>y</sup>, C(=O)NR<sup>x</sup>R<sup>y</sup>, NR'SO<sub>2</sub>R<sup>x</sup>, NR'SO<sub>2</sub>NR<sup>x</sup>R<sup>Y</sup>, CR'R" SO<sub>2</sub>R' or CR'R" SO<sub>2</sub>NR<sup>x</sup>R<sup>y</sup>;

each $R^3$ is independently selected from hydrogen, $C_1$-$C_6$ unsubstituted or substituted alkyl, OR', COOR' and CONR'R";

$R^4$ is a group selected from hydrogen, halogen, CN, $C_1$-$C_6$ unsubstituted or substituted alkyl, OR', and NHR';

each of R<sup>x</sup> and R<sup>y</sup> is independently selected from H, alkyl, cycloalkyl, heterocycloalkyl, aryl, heteroaryl and R<sup>x</sup> and R<sup>y</sup> may together form a 3- to 7-membered ring, and each of R<sup>x</sup> and R<sup>y</sup> is optionally substituted with one or more of halogen, CN, OR', NR'R", alkyl, haloalkyl, cyanoalkyl, hydroxyalkyl and alkoxyalkyl;

each of R' and R" is independently selected from hydrogen and $C_1$-$C_6$ unsubstituted and substituted alkyl and R' and R" may together form a 3- to 7-membered ring; and n is 1 or 2, or a pharmaceutically acceptable form or an isotope derivative thereof, effective to treat or reduce one or more of inflammatory diseases, immune-mediated diseases and cancer, or a related disease or disorder, in a mammal, including a human.

In yet another aspect, the invention generally relates to a method for treating or reducing a disease or disorder, comprising: administering to a subject in need thereof a pharmaceutical composition comprising a compound having the structural formula (VII):

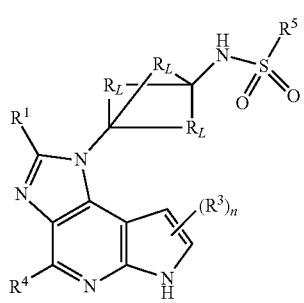

(VII)

wherein $R^1$ is selected from hydrogen, $C_1$-$C_6$ unsubstituted or substituted alkyl, OR', COOR' and CONR'R";

each $R^3$ is independently selected from hydrogen, $C_1$-$C_6$ unsubstituted or substituted alkyl, OR', COOR' and CONR'R";

R$^4$ is a group selected from hydrogen, halogen, CN, C$_1$-C$_6$ unsubstituted or substituted alkyl, OR', and NHR';

R$^5$ is R$^x$ or NR$^x$R$^y$, wherein each of R$^x$ and R$^y$ is independently selected from H, alkyl, cycloalkyl, heterocycloalkyl, aryl, heteroaryl and R$^x$ and R$^y$ may together form a 3- to 7-membered ring, and each of R$^x$ and R$^y$ is optionally substituted with one or more of halogen, CN, OR', NR'R", alkyl, haloalkyl, cyanoalkyl, hydroxyalkyl and alkoxyalkyl; provided that when R$^5$ is R$^x$, R$^x$ is not H;

each R$_L$ is independently (CH$_2$)$_m$ and m is independently 0, 1, 2 or 3, wherein when m is 0, the respective bridge is absent;

each R' and R" is independently selected from hydrogen and C$_1$-C$_6$ unsubstituted and substituted alkyl and R' and R" may together form a 3- to 7-membered ring; and n is 1 or 2, or a pharmaceutically acceptable form or an isotope derivative thereof, and a pharmaceutically acceptable excipient, carrier, or diluent, effective to treat or reduce one or more of inflammatory diseases, immune-mediated diseases and cancer, or a related disease or disorder, in a mammal, including a human.

In yet another aspect, the invention generally relates to a method for treating or reducing a disease or disorder, comprising: administering to a subject in need thereof a pharmaceutical composition comprising a compound disclosed herein, wherein the disease or disorder is one or more of inflammatory diseases, immune-mediated diseases and cancer, or a related disease or disorder.

In yet another aspect, the invention generally relates to use of a compound disclosed herein and a pharmaceutically acceptable excipient, carrier, or diluent, in preparation of a medicament for treating a disease or disorder.

Definitions

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, atropisomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example, "C$_{1-6}$ alkyl" is intended to encompass, C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$ alkyl.

Where substituent groups are specified by their conventional chemical formulae, written from left to right, they equally encompass the chemically identical substituents that would result from writing the structure from right to left, e.g., —C(=O)—O— is equivalent to —O—C(=O)—.

Structures of compounds of the invention are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions (e.g., aqueous, neutral, and several known physiological conditions).

As used herein, the term "alkyl" refers to a straight or branched hydrocarbon chain radical consisting solely of carbon and hydrogen atoms, containing no unsaturation, having from one to ten carbon atoms (e.g., C$_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a C$_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C (O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C (O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroatom" refers to oxygen (O), nitrogen (N), sulfur (S), and phosphorus (P).

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl, which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "administering" refers to oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Suitable routes of administration for a particular patient will depend on the nature and severity of the disease or condition being treated or the nature of the therapy being used and on the nature of the active compound.

Administration may be by any suitable route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies.

The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, gels, for example, water or water/propylene glycol solutions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, 1995 *J. Biomater Sci. Polym.* Ed. 7:623-645; as biodegradable and injectable gel formulations (see, e.g., Gao 1995 *Pharm. Res.* 12:857-863); or, as microspheres for oral administration (see, e.g., Eyles 1997 *J. Pharm. Pharmacol.* 49:669-674).

As used herein, the terms "disease," "condition," and "disorder" are used interchangeably herein and refer to a state of being or health status of a patient or subject capable of being treated with a compound, pharmaceutical composition, or method provided herein.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "inhibition," "inhibit" and "inhibiting" and the like in reference to a biological target (e.g., JAKs) inhibitor interaction refers to negatively affecting (e.g., decreasing) the activity or function of the protein relative to the activity or function of the protein in the absence of the inhibitor. In embodiments, inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high-performance liquid chromatography.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchlorate acid or with organic acids such as acetic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, p-toluenesulfonate, undecanoate, valerate salts, and the like. In some embodiments, organic acids from which salts can be derived include, for example, acetic acid, propionic acid, glycolic acid, pyruvic acid, lactic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate." Pharmaceutically acceptable solvates and hydrates are complexes that, for example, can include 1 to about 100, or 1 to about 10, or 1 to about 2, about 3 or about 4, solvent or water molecules. It will be understood that the term "compound"" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in Bioreversible Carriers in Drug Design, ed. Edward B. Roche, American Pharmaceutical Association and Pergamon Press, 1987, both of which are incorporated in full by reference herein.

Prodrug forms often offer advantages of solubility, tissue compatibility, or delayed release in the mammalian organism. (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif, 1992.) Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having a carbonate, carbamate, amide or alkyl ester moiety covalently bonded to any of the above substituents disclosed herein.

Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. A subject to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), rodents (e.g., rats and/or mice), etc. In certain embodiments, the non-human animal is a mammal. The non-human animal may be a male or female at any stage of development. A non-human animal may be a transgenic animal. Typically, the terms "subject" and "patient" are used interchangeably herein in reference to a human subject.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. Treating or treatment thus refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters, for example, the results of a physical examination, neuropsychiatric exams, and/or a psychiatric evaluation. As compared with an equivalent untreated control, such reduction or degree of amelioration may be at least 5%, 10%, 20%, 40%, 50%, 60%, 80%, 90%, 95%, or 100% as measured by any standard technique.

Treatment methods include administering to a subject a therapeutically effective amount of a compound described herein. The administering step may be a single administration or may include a series of administrations. The length of the treatment period depends on a variety of factors, such as the severity of the condition, the patient's age, the concentration of the compound, the activity of the compositions used in the treatment, or a combination thereof. It will also be appreciated that the effective dosage of an agent used for the treatment may increase or decrease over the course of a particular treatment regime. Changes in dosage may result and become apparent by standard diagnostic assays known in the art. In some instances, chronic administration may be required. For example, the compositions are administered to the subject in an amount and for a duration sufficient to treat the patient.

DETAILED DESCRIPTION OF THE INVENTION

The invention is based on an unexpected discovery of a novel class of orally and/or topically available, selective and potent JAK1 therapeutics. The invention also provides pharmaceutical compositions of these compounds and methods of preparation and use thereof. The JAK1 inhibitors disclosed herein exhibited exceptional potency and selectivity profiles.

More specifically, the novel JAK1 inhibitors disclosed herein enjoy improved potency as demonstrated by the superior binding affinities to JAK1 (e.g., IC50's of about 3-45 nM) and the potential for reduced hematopoietic side effects as demonstrated by their excellent specificity (e.g., JAK2 IC50's>20×JAK1).

In one aspect, the invention generally relates to a compound having the structural formula (I):

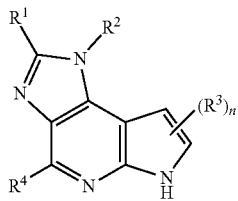

(I)

wherein
- $R^1$ is selected from hydrogen, $C_1$-$C_6$ (e.g., $C_1$-$C_3$) unsubstituted or substituted alkyl, OR', COOR' and CONR'R";
- $R^2$ is selected from $C_3$-$C_{10}$ (e.g., $C_3$-$C_6$) cycloalkyl, bicycloalkyl, spirocyclic or bridgedcycloalkyl, substituted with NR'C(=O)$R^x$, NR'C(=O)O$R^x$, NR'C(=O)NR$^x$R$^y$, C(=O)NR$^x$R$^y$, NR'SO$_2$R$^x$, NR'SO$_2$NR$^x$R$^Y$, CR'R"SO$_2$R' or CR'R"SO$_2$NR$^x$R$^y$;
- each $R^3$ is independently selected from hydrogen, $C_1$-$C_6$ (e.g., $C_1$-$C_3$) unsubstituted or substituted alkyl, OR', COOR' and CONR'R";
- $R^4$ is a group selected from hydrogen, halogen, CN, $C_1$-$C_6$ (e.g., $C_1$-$C_3$) unsubstituted or substituted alkyl, OR', and NHR';
- each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and $R^x$ and $R^y$ may together form a 3- to 7-membered (e.g., 3- or 4-membered) ring, and each of $R^x$ and $R^y$ is optionally substituted with one or more of halogen (e.g., F, Cl), CN, OR', NR'R", alkyl (e.g., $C_1$-$C_6$ alkyl), haloalkyl (e.g., CHF$_2$, CF$_3$), cyanoalkyl (e.g., CH$_2$CN), hydroxyalkyl (e.g., CH$_2$OH) and alkoxyalkyl (e.g., CH$_2$O-alkyl);
- each of R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and
- n is 1 or 2, or a pharmaceutically acceptable form or an isotope derivative thereof.

In certain embodiments of formula (I), $R^4$ is H and the compound has the structural formula (II):

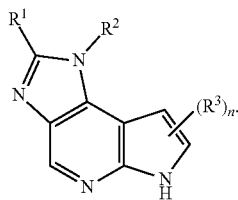

(II)

In certain embodiments of formula (II), n is 1, and the compound has the structural formula (III):

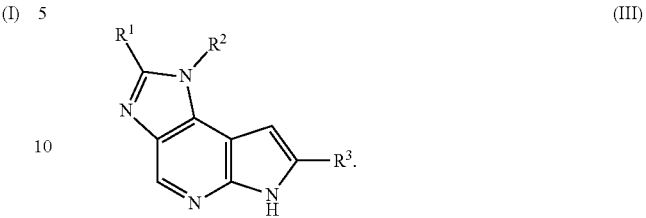

(III)

In certain embodiments of formula (I), $R^1$ is H, and the compound has the structural formula (IV):

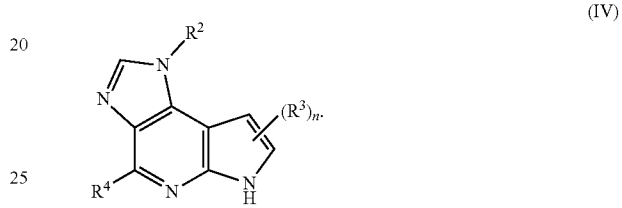

(IV)

In certain embodiments of formulas (I), (II), (III) and (IV), both of $R^1$ and $R^4$ is H.

In certain embodiments of formulas (I), (II), (III) and (IV), $R^1$ is methyl and $R^4$ is H.

In certain embodiments of formulas (I), (II), (III) and (IV), n is 1.

In certain embodiments, $R^3$ is H.

In an exemplary embodiment where $R^1$ is H, $R^4$ is H, n is 1, the compound has structural formula (V):

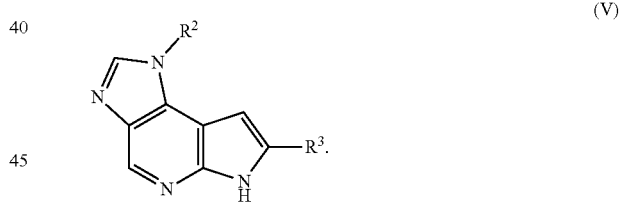

(V)

In a further exemplary embodiment in formula (V), $R^3$ is H, and the compound has the structural formula (VI):

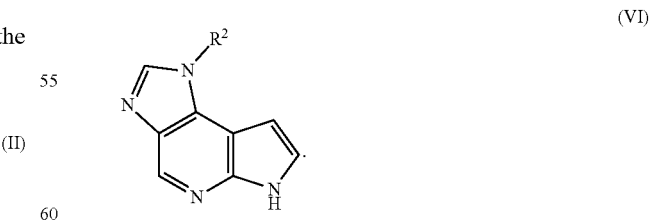

(VI)

$R^2$ may be selected from $C_3$-$C_{10}$ (e.g., $C_3$-$C_6$) cycloalkyl, bicycloalkyl, spirocyclic or bridgedcycloalkyl, substituted with a group selected from NR'C(=O)$R^x$, NR'C(=O)O$R^x$, NR'C(=O)NR$^x$R$^y$, C(=O)NR$^x$R$^y$, NR'SO$_2$R$^x$, NR'SO$_2$NR$^x$R$^Y$, CR'R"SO$_2$R' or CR'R"SO$_2$NR$^x$R$^y$, wherein each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl), and each of $R^x$ and $R^y$ is optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl), and $R^x$ and $R^y$ may together form a 3- to 7-membered (e.g., 3- or 4-membered) ring. Each of R' and R" is independently selected from hydrogen and $C_1$-$C_6$ (e.g., $C_1$-$C_3$) unsubstituted and substituted alkyl. R' and R" may together form a 3- to 7-membered ring.

It is noted that the 3- to 7-membered (e.g., 3- or 4-membered) ring, optionally formed by R' and R" together or by $R^x$ and R together, may be a hetero 3- to 7-membered (e.g., 3- or 4-membered) ring, with 0 to 3 carbon atoms replaced by one or more heteroatoms selected from N, O, S and P.

Heterocycloalkyl (e.g., $C_2$-$C_9$ heterocycloalkyl) and heteroaryl (e.g., $C_3$-$C_9$ heteroaryl) may have 1-4 carbon atoms replaced by one or more heteroatoms selected from N, O, S and P.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with NR'C(=O)$R^x$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with NR'C(=O)O$R^x$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with NR'C(=O)NR$^x$R$^y$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with C(=O)NR$^x$R$^y$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with NR'SO$_2$R$^x$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with NR'SO$_2$NR$^x$R$^y$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with CR'R"SO$_2$R$^x$.

In certain embodiments, $R^2$ is selected from $C_3$-$C_{10}$ (e.g., $C_3$-$C_6$) cycloalkyl, bicycloalkyl, spirocyclic or bridgedcycloalkyl, substituted with CR'R"SO$_2$NR$^x$R$^Y$.

In certain embodiments, $R^2$ comprises the following moiety:

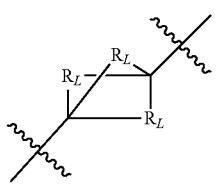

wherein each $R_L$ is independently $(CH_2)_m$ and m is independently 0, 1, 2 or 3, wherein when an m is 0, the respective bridge is absent; provided that at least one m is not 0.

In certain embodiments, no m is 0 (i.e., each m is independently 1, 2 or 3).

In certain embodiments, not more than one m is 0 (i.e., not more than one $R_L$'s is absent).

In certain embodiments, each m is independently 1, 2 or 3.

In certain embodiments, all m's are the same integer selected from 1, 2 and 3.

In certain embodiments, all m's are not the same integer selected from 1, 2 and 3.

In certain embodiments, each m is 1 (i.e., forming a [1,1,1]-bicyclic moiety).

In certain embodiments, each m is 2 (i.e., forming a [2,2,2]-bicyclic moiety).

In certain embodiments, $R^2$ comprises:

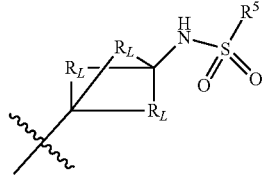

wherein $R^5$ is $R^x$ or NR$^x$R$^y$, wherein each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and $R^x$ and $R^y$ may together form a 3- to 7-membered (e.g., 3- or 4-membered) ring, and each of $R^x$ and $R^y$ is and optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl); provided that when $R^5$ is $R^x$, $R^x$ is not H (i.e., $R^5$ is not H). Each of R' and R" is independently selected from hydrogen and $C_1$-$C_6$ unsubstituted and substituted alkyl and R' and R" may together form a 3- to 7-membered (e.g., 3- or 4-membered) ring.

In certain embodiments, $R^5$ is $R^x$.

In certain embodiments, $R^5$ is a $C_1$-$C_6$ alkyl (e.g., $C_1$-$C_3$ alkyl), optionally substituted with one or more halogen (e.g., F, Cl), $C_1$-$C_6$ (e.g., $C_1$-$C_3$) alkoxy, CN or amino groups.

In certain embodiments, $R^5$ is a $C_1$-$C_6$ alkyl (e.g., $C_1$-$C_3$ alkyl).

In certain embodiments, $R^5$ is a $C_1$-$C_6$ alkyl (e.g., $C_1$-$C_3$ alkyl), substituted with a halogen (e.g., F, Cl), $C_1$-$C_6$ (e.g., $C_1$-$C_3$) alkoxy, or CN.

In certain embodiments, $R^5$ is a $C_1$-$C_6$ alkyl (e.g., $C_1$-$C_3$ alkyl), substituted with a CN.

In certain embodiments, $R^x$ is a linear or branched $C_1$-$C_6$ alkyl.

In certain embodiments, $R^x$ is a linear or branched $C_2$-$C_4$ alkyl.

In certain embodiments, $R^x$ is n-propyl or isopropyl.

In certain embodiments, $R^5$ is NR$^x$R$^y$.

In certain embodiments, one of $R^x$ and $R^y$ is H.

In certain embodiments, $R^5$ is NR$^x$R$^y$, wherein each of $R^x$ and $R^y$ is independently selected from hydrogen and $C_1$-$C_6$ (e.g., $C_1$-$C_3$) unsubstituted and substituted alkyl.

In certain embodiments, $R^5$ is NR$^x$R$^Y$, wherein the $R^x$ and $R^y$ together, along with the N in NR$^x$R$^y$, form a 3- to 7-membered (e.g., 3-, 4-, or 5-membered) heterocyclic group, optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl).

In certain embodiments, the heterocyclic group is a 4-membered heterocyclic group.

In certain embodiments, R⁵ is NRˣRʸ, wherein each of Rˣ and Rʸ is independently selected from hydrogen and $C_1$-$C_6$ (e.g., $C_1$-$C_3$) unsubstituted alkyl.

In certain embodiments, R⁵ is NRˣRʸ, wherein Rˣ and Rʸ together form a 3- or 4-membered) cycloalkyl ring, substituted with a CN.

In certain embodiments, each $R_L$ is $CH_2$.

In certain embodiments, each $R_L$ is $(CH_2)_2$.

In another aspect, the invention generally relates to a compound having the structural formula (VII):

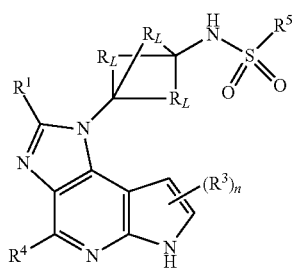

(VII)

wherein
- R¹ is selected from hydrogen, $C_1$-$C_6$ (e.g., $C_1$-$C_3$) unsubstituted or substituted alkyl, OR', COOR' and CONR'R";
- each R³ is independently selected from hydrogen, $C_1$-$C_6$ (e.g., $C_1$-$C_3$) unsubstituted or substituted alkyl, OR', COOR' and CONR'R";
- R⁴ is a group selected from hydrogen (e.g., F, Cl), halogen, CN, $C_1$-$C_6$ (e.g., $C_1$-$C_3$) unsubstituted or substituted alkyl, OR', and NHR';
- R⁵ is Rˣ or NRˣRʸ, wherein each of Rˣ and Rʸ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and Rˣ and Rʸ may together form a 3- to 7-membered (e.g., 3- or 4-membered) ring, and optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl); provided that when R⁵ is Rˣ, Rˣ is not H (i.e., R⁵ is not H);
- each $R_L$ is independently $(CH_2)_m$ and m is independently 0, 1, 2 or 3, wherein when m is 0, the respective bridge is absent;
- each R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and
- n is 1 or 2, or a pharmaceutically acceptable form or an isotope derivative thereof.

In certain embodiments of (VII), not more than one m is 0 (i.e., not more than one $R_L$'s is absent).

In certain embodiments of (VII), no m is 0 (i.e., each m is independently 1, 2 or 3).

In certain embodiments of (VII), all m's are the same integer selected from 1, 2 and 3.

In certain embodiments of (VII), all m's are not the same integer selected from 1, 2 and 3.

In certain embodiments of (VII), each m is 1 (i.e., forming a [1,1,1]-bicyclic moiety).

In certain embodiments of (VII), each m is 2 (i.e., forming a [2,2,2]-bicyclic moiety).

In certain embodiments of (VII), R⁴ is H.

In certain embodiments of (VII), R¹ is H.

In certain embodiments of (VII), R¹ is methyl.

In certain embodiments of (VII), n is 1.

In certain embodiments of (VII), R⁴ is H and n is 1, and the compound has the structural formula (VIII):

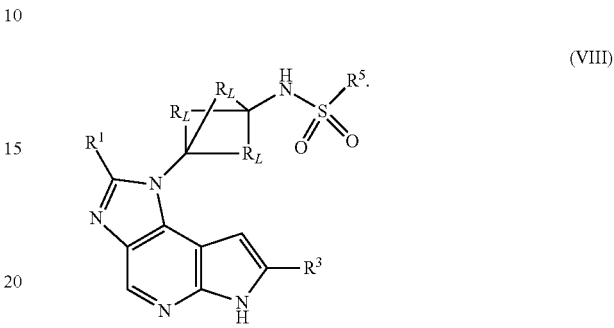

(VIII)

In certain embodiments of (VIII), R¹ is methyl and R³ is H.

In certain embodiments of (VIII), both R¹ and R³ is H, having the structural formula (IX):

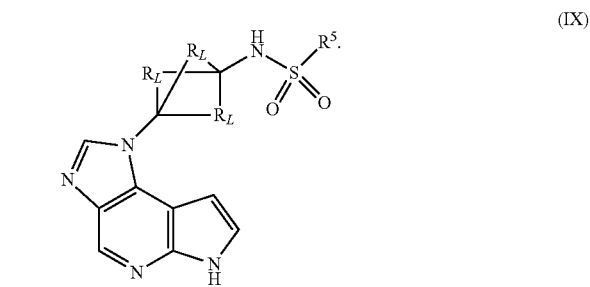

(IX)

In certain embodiments of (VIII), each $R_L$ is $CH_2$, and the compound has the structural formula (X):

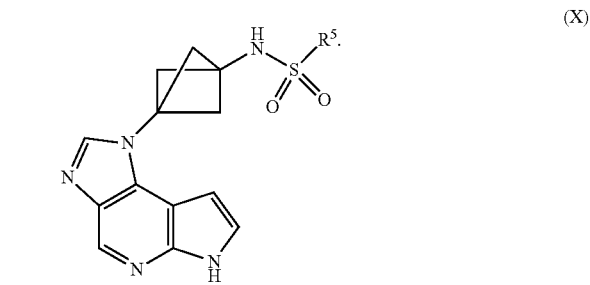

(X)

In certain embodiments of (X), R⁵ is Rˣ.

In certain embodiments of (X), Rˣ is a linear or branched $C_1$-$C_6$ (e.g., $C_1$-$C_3$) alkyl, optionally substituted with one or more halogen (e.g., F, Cl), $C_1$-$C_6$ (e.g., $C_1$-$C_3$) alkoxy, CN or amino groups.

In certain embodiments of (X), Rˣ is a linear or branched $C_2$-$C_4$ alkyl.

In certain embodiments of (X), Rˣ is n-propyl or isopropyl.

In certain embodiments of (X), $R^5$ is $NR^xR^y$.

In certain embodiments of (X), one of $R^x$ and $R^y$ is H.

In certain embodiments, the $R^x$ and $R^y$ together, along with the N in $NR^xR^Y$, form a 3- to 5-membered (e.g., 3-, 4- or 5-membered) heterocyclic group, optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl).

In certain embodiments, the heterocyclic group is a 4-membered heterocyclic group.

A list of non-limiting examples of compounds of the invention is provided in Table 1.

TABLE 1

Exemplary Compounds

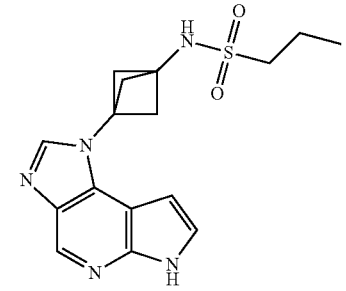 [SMILES: CCCS(=O)(=O)NC12CC(n3cnc4cnc5[nH]ccc5c43)(C1)C2]

TABLE 1-continued

Exemplary Compounds

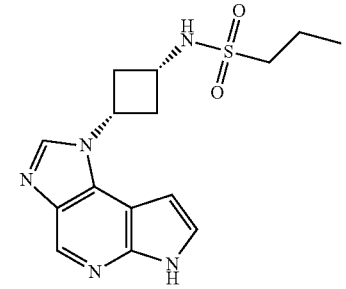 [SMILES: CCCS(=O)(=O)N[C@H]1C[C@@H](n2cnc3cnc4[nH]ccc4c32)C1]

TABLE 1-continued
Exemplary Compounds
10 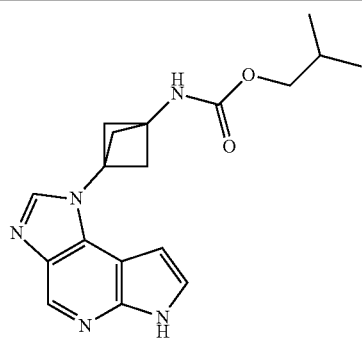 [SMILES: CC(C)COC(=O)NC12CC(n3cnc4cnc5[nH]ccc5c43)(C1)C2]
11 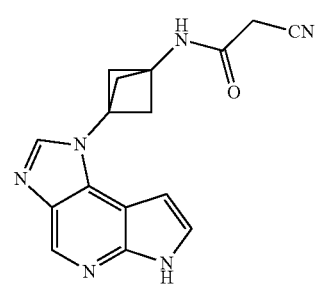 [SMILES: N#CCC(=O)NC12CC(n3cnc4cnc5[nH]ccc5c43)(C1)C2]
12 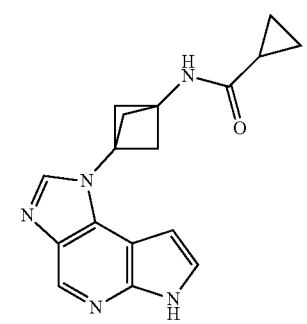 [SMILES: O=C(NC12CC(n3cnc4cnc5[nH]ccc5c43)(C1)C2)C1CC1]
13 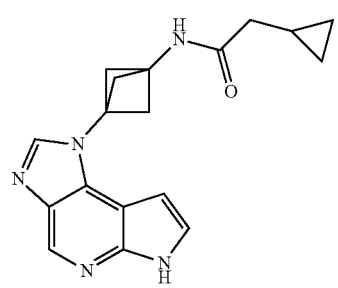 [SMILES: O=C(CC1CC1)NC12CC(n3cnc4cnc5[nH]ccc5c43)(C1)C2]
14 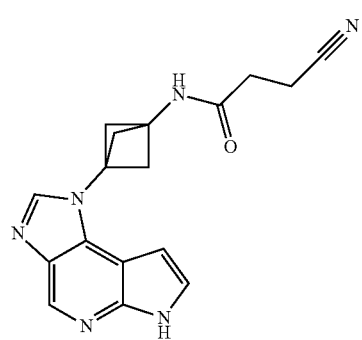 [SMILES: N#CCCC(=O)NC12CC(n3cnc4cnc5[nH]ccc5c43)(C1)C2]
TABLE 1-continued
Exemplary Compounds
15 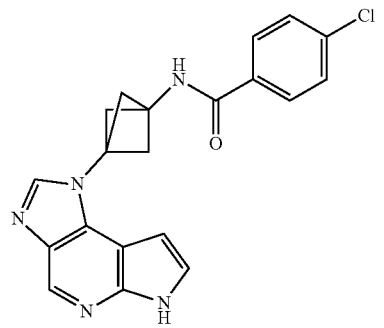 [SMILES: O=C(NC12CC(n3cnc4cnc5[nH]ccc5c43)(C1)C2)c1ccc(Cl)cc1]
16 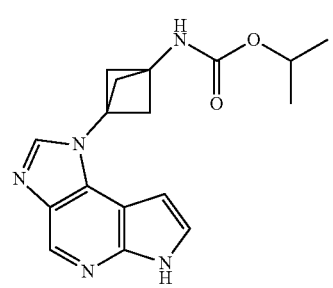 [SMILES: CC(C)OC(=O)NC12CC(n3cnc4cnc5[nH]ccc5c43)(C1)C2]
17 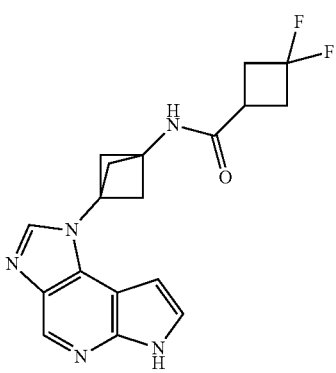 [SMILES: O=C(NC12CC(n3cnc4cnc5[nH]ccc5c43)(C1)C2)C1CC(F)(F)C1]
18 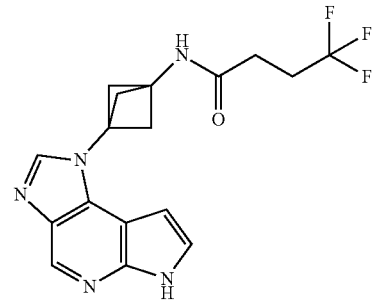 [SMILES: O=C(CCC(F)(F)F)NC12CC(n3cnc4cnc5[nH]ccc5c43)(C1)C2]

TABLE 1-continued
Exemplary Compounds
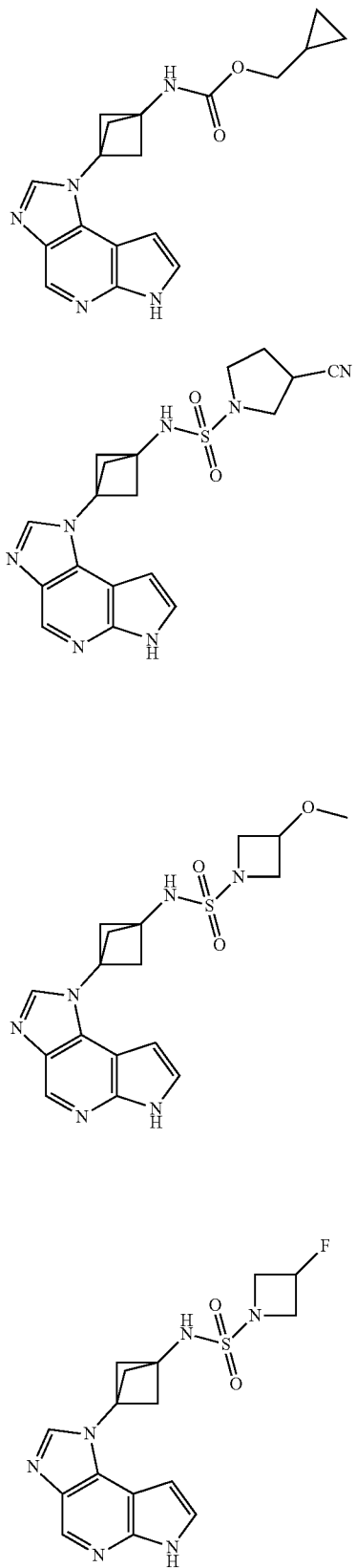
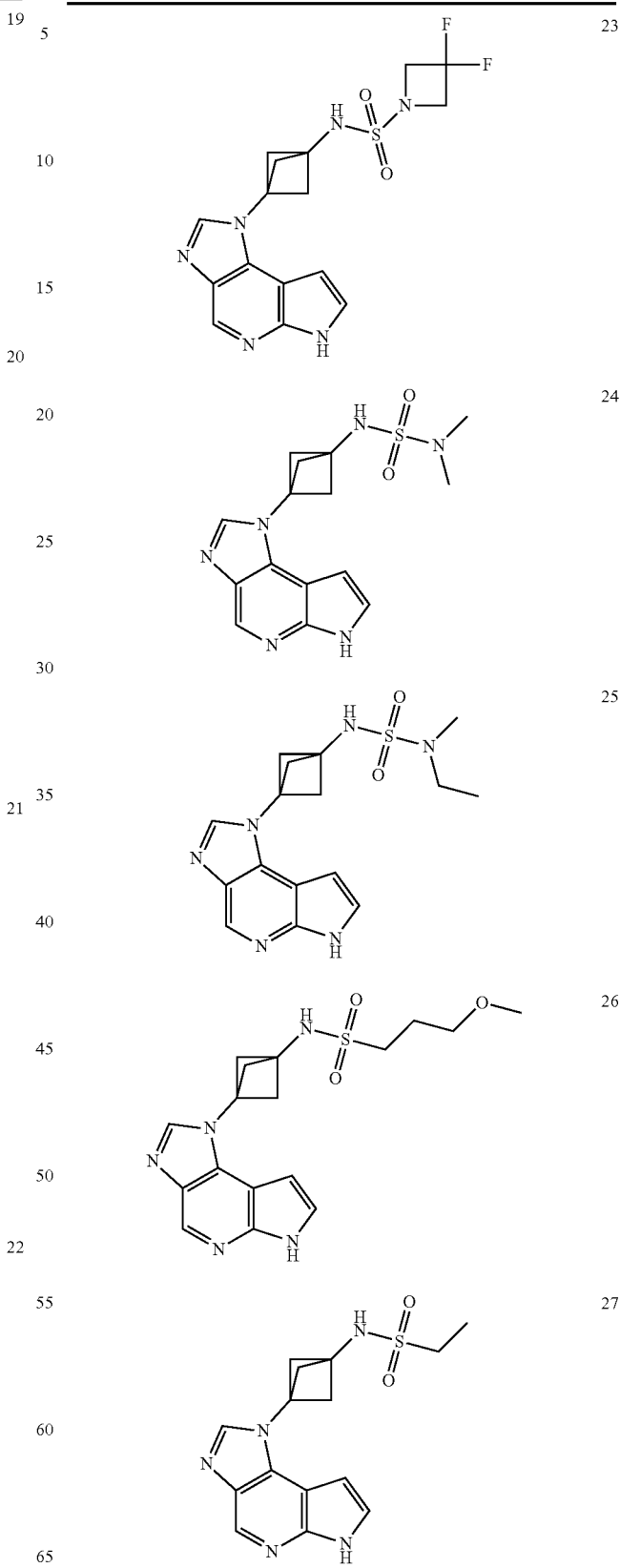

TABLE 1-continued

Exemplary Compounds

| No. | Structure |
|---|---|
| 28 | 4-chlorophenylsulfonamide-bicyclobutyl-imidazo-pyrrolopyridine |
| 29 | 1-methylpyrazole-4-sulfonamide-bicyclobutyl-imidazo-pyrrolopyridine |
| 30 | isopropylsulfonamide-bicyclobutyl-imidazo-pyrrolopyridine |
| 31 | n-butylsulfonamide-bicyclobutyl-imidazo-pyrrolopyridine |
| 32 | 3,3,3-trifluoropropylsulfonamide-bicyclobutyl-imidazo-pyrrolopyridine |
| 33 | cyanomethylsulfonamide-bicyclobutyl-imidazo-pyrrolopyridine |
| 34 | N-propylurea-bicyclobutyl-imidazo-pyrrolopyridine |
| 35 | N-cyclopropylurea-bicyclobutyl-imidazo-pyrrolopyridine |
| 36 | N-isobutylurea-bicyclobutyl-imidazo-pyrrolopyridine |
| 37 | 3,3-difluoroazetidine-carboxamide-bicyclobutyl-imidazo-pyrrolopyridine |

TABLE 1-continued
Exemplary Compounds
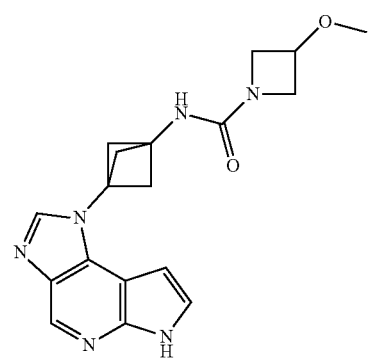 [SMILES: COC1CN(C(=O)NC23CC(n4cnc5cnc6[nH]ccc6c54)(C2)C3)C1]
38
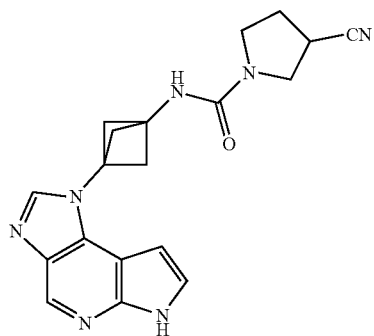 [SMILES: N#CC1CCN(C(=O)NC23CC(n4cnc5cnc6[nH]ccc6c54)(C2)C3)C1]
39
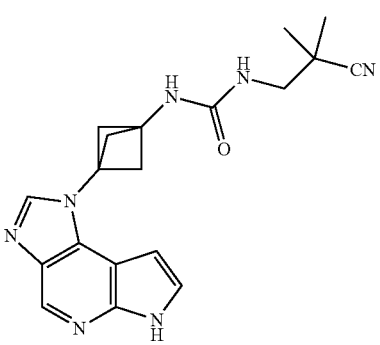 [SMILES: CC(C)(C#N)CNC(=O)NC12CC(n3cnc4cnc5[nH]ccc5c43)(C1)C2]
40
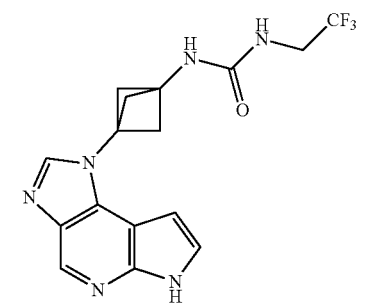 [SMILES: O=C(NCC(F)(F)F)NC12CC(n3cnc4cnc5[nH]ccc5c43)(C1)C2]
41
TABLE 1-continued
Exemplary Compounds
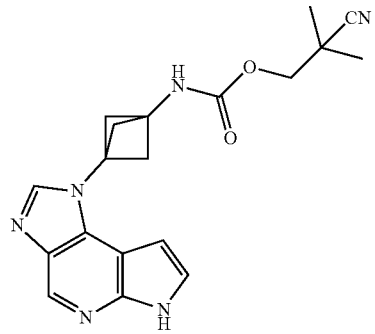 [SMILES: CC(C)(C#N)COC(=O)NC12CC(n3cnc4cnc5[nH]ccc5c43)(C1)C2]
42
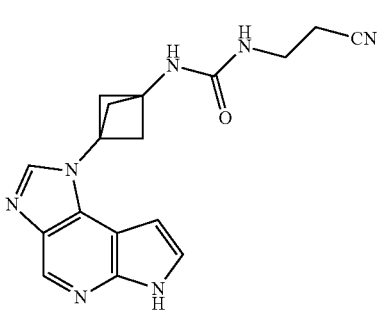 [SMILES: N#CCCNC(=O)NC12CC(n3cnc4cnc5[nH]ccc5c43)(C1)C2]
43
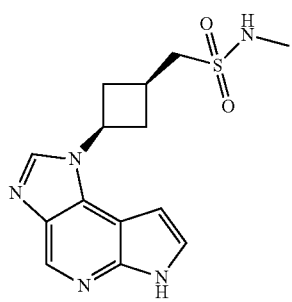 [SMILES: CNS(=O)(=O)C[C@H]1C[C@@H](n2cnc3cnc4[nH]ccc4c32)C1]
44

TABLE 1-continued

Exemplary Compounds

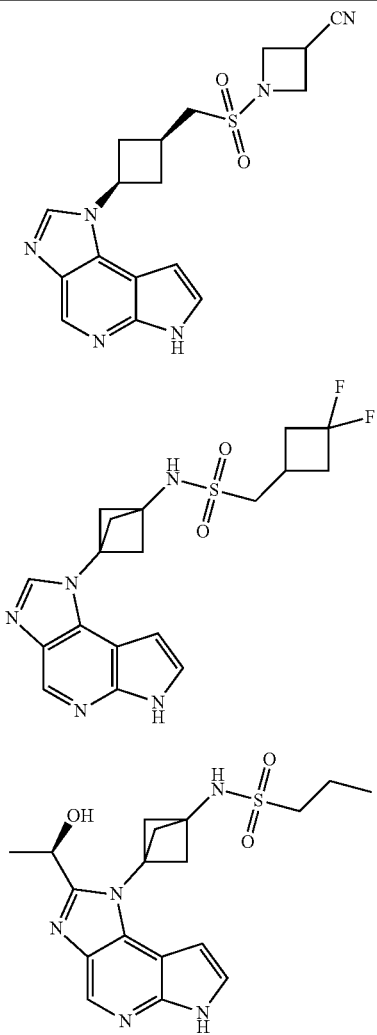

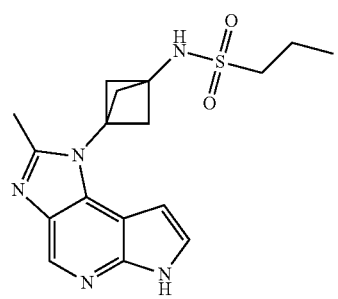 [SMILES: CCCS(=O)(=O)NC12CC(n3c(C)nc4cnc5[nH]ccc5c43)(C1)C2]

In certain embodiments, the compound has the structural formula of compound 1. In certain embodiments, the compound has the structural formula of compound 4. In certain embodiments, the compound has the structural formula of compound 5. In certain embodiments, the compound has the structural formula of compound 6. In certain embodiments, the compound has the structural formula of compound 21. In certain embodiments, the compound has the structural formula of compound 23. In certain embodiments, the compound has the structural formula of compound 31. In certain embodiments, the compound has the structural formula of compound 32. In certain embodiments, the compound has the structural formula of compound 45. In certain embodiments, the compound has the structural formula of compound 46. In certain embodiments, the compound has the structural formula of compound 48.

TABLE 1A

Exemplary Compounds

| Example/ Compound No. | Compound Name | Compound Structure |
|---|---|---|
| 1 | N-(3-(imidazo[4,5-d]pyrrolo[2,3-b]pyridin-1(6H)-yl)bicyclo[1.1.1]pentan-1-yl)propane-1-sulfonamide | 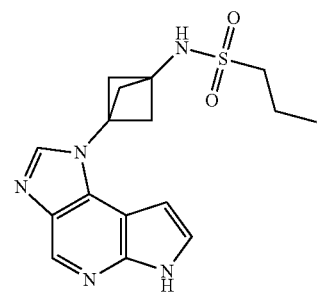 [SMILES: CCCS(=O)(=O)NC12CC(n3cnc4cnc5[nH]ccc5c43)(C1)C2] |

TABLE 1A-continued
Exemplary Compounds
| Example/ Compound No. | Compound Name | Compound Structure |
|---|---|---|
| 4 | 3-Cyano-N-(3-(imidazo[4,5-d]pyrrolo[2,3-b]pyridin-1(6H)-yl)bicyclo[1.1.1]pentan-1-yl)azetidine-1-sulfonamide | 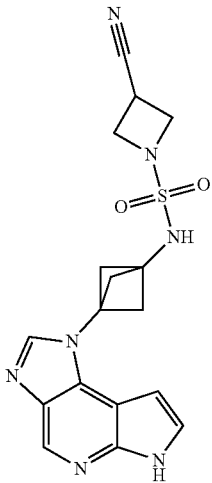 |
| 5 | N-(3-(imidazo[4,5-d]pyrrolo[2,3-b]pyridin-1(6H)-yl)bicyclo[1.1.1]pentan-1-yl)-2-methylpropane-1-sulfonamide | 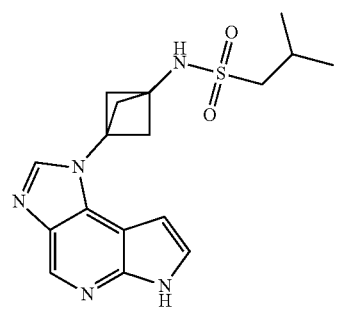 [SMILES: CC(C)CS(=O)(=O)NC12CC(n3cnc4cnc5[nH]ccc5c43)(C1)C2] |
| 6 | N-(3-(imidazo[4,5-d]pyrrolo[2,3-b]pyridin-1(6H)-yl)bicyclo[1.1.1]pentan-1-yl)-2-methoxyethanesulfonamide | 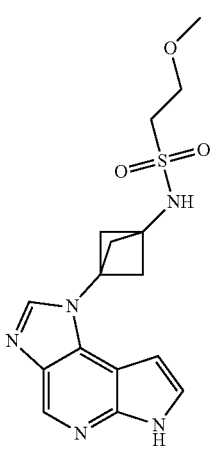 |

TABLE 1A-continued

Exemplary Compounds

| Example/ Compound No. | Compound Name | Compound Structure |
|---|---|---|
| 21 | N-(3-(imidazo[4,5-d]pyrrolo[2,3-b]pyridin-1(6H)-yl)bicyclo[1.1.1]pentan-1-yl)-3-methoxyazetidine-1-sulfonamide | 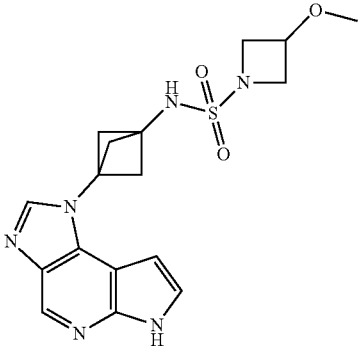 [SMILES: COC1CN(S(=O)(=O)NC23CC(n4cnc5cnc6[nH]ccc6c54)(C2)C3)C1] |
| 23 | 3,3-Difluoro-N-(3-(imidazo[4,5-d]pyrrolo[2,3-b]pyridin-1(6H)-yl)bicyclo[1.1.1]pentan-1-yl)azetidine-1-sulfonamide | 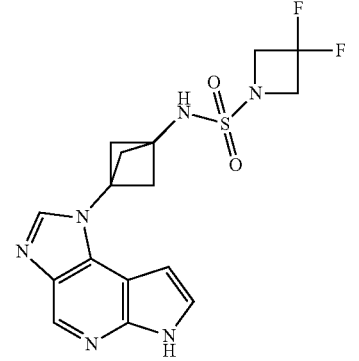 |
| 31 | N-(3-(imidazo[4,5-d]pyrrolo[2,3-b]pyridin-1(6H)-yl)bicyclo[1.1.1]pentan-1-yl)butane-1-sulfonamide | 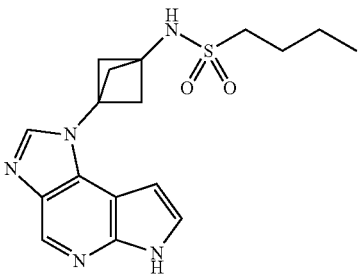 [SMILES: CCCCS(=O)(=O)NC12CC(n3cnc4cnc5[nH]ccc5c43)(C1)C2] |
| 32 | 3,3,3-Trifluoro-N-(3-(imidazo[4,5-d]pyrrolo[2,3-b]pyridin-1(6H)-yl)bicyclo[1.1.1]pentan-1-yl)propane-1-sulfonamide | 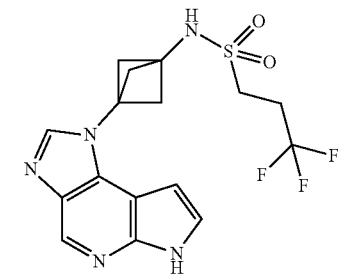 [SMILES: O=S(=O)(CCC(F)(F)F)NC12CC(n3cnc4cnc5[nH]ccc5c43)(C1)C2] |

TABLE 1A-continued

Exemplary Compounds

| Example/ Compound No. | Compound Name | Compound Structure |
|---|---|---|
| 45 | 1-(((Cis-3-(imidazo[4,5-d]pyrrolo[2,3-b]pyridin-1(6H)-yl)cyclobutyl)methyl)sulfonyl)azetidine-3-carbonitrile | 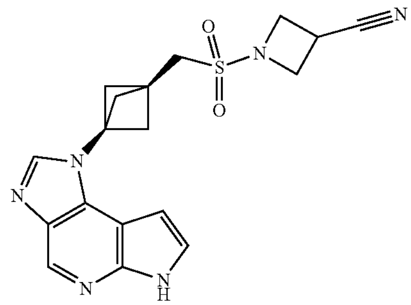 [SMILES: N#CC1CN(S(=O)(=O)C[C@]23C[C@](n4cnc5cnc6[nH]ccc6c54)(C2)C3)C1] |
| 46 | 1-(3,3-Difluorocyclobutyl)-N-(3-(imidazo[4,5-d]pyrrolo[2,3-b]pyridin-1(6H)-yl)bicyclo[1.1.1]pentan-1-yl)methanesulfonamide | 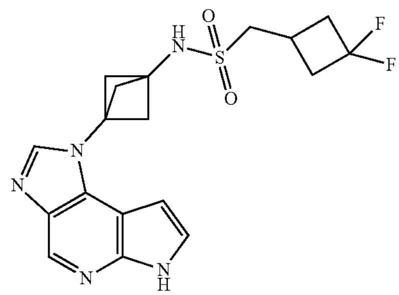 [SMILES: O=S(=O)(CC1CC(F)(F)C1)NC12CC(n3cnc4cnc5[nH]ccc5c43)(C1)C2] |
| 48 | N-(3-(2-methylimidazo[4,5-d]pyrrolo[2,3-b]pyridin-1(6H)-yl)bicyclo[1.1.1]pentan-1-yl)propane-1-sulfonamide | 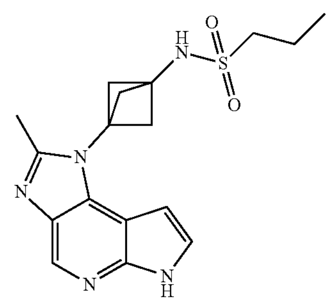 [SMILES: CCCS(=O)(=O)NC12CC(n3c(C)nc4cnc5[nH]ccc5c43)(C1)C2] |

As discussed herein, isotope derivative compounds having one or more hydrogen atoms replaced with deuterium atoms are contemplated in the presented invention. In certain embodiments, a compound of the invention has one or more hydrogen atoms replaced with a deuterium atom. In certain embodiments, a compound of the invention has one hydrogen atom replaced with a deuterium atom. In certain embodiments, a compound of the invention has more than one hydrogen atom replaced with a deuterium atom.

In yet another aspect, the invention generally relates to a pharmaceutical composition comprising a compound according to the herein disclosed invention, effective to treat or reduce one or more diseases or disorders, in a mammal, including a human, and a pharmaceutically acceptable excipient, carrier, or diluent.

In yet another aspect, the invention generally relates to a pharmaceutical composition comprising a compound having the structural formula (I):

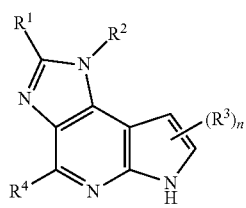

(I)

wherein
  $R^1$ is selected from hydrogen, $C_1$-$C_6$ (e.g., $C_1$-$C_3$) unsubstituted or substituted alkyl, OR', COOR' and CONR'R'';
  $R^2$ is selected from $C_3$-$C_{10}$ (e.g., $C_3$-$C_6$) cycloalkyl, bicycloalkyl, spirocyclic or bridgedcycloalkyl, substituted with NR'C(=O)$R^x$, NR'C(=O)O$R^x$, NR'C(=O)NR$^x$R$^y$, C(=O)NR$^x$R$^y$, NR'SO$_2$R$^x$, NR'SO$_2$NR$^x$R$^Y$, CR'R''SO$_2$R$^x$ or CR'R''SO$_2$NR$^x$R$^y$;
  each $R^3$ is independently selected from hydrogen, $C_1$-$C_6$ (e.g., $C_1$-$C_3$) unsubstituted or substituted alkyl, OR', COOR' and CONR'R'';

R⁴ is a group selected from hydrogen, halogen, CN, $C_1$-$C_6$ (e.g., $C_1$-$C_3$) unsubstituted or substituted alkyl, OR', and NHR';

each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and $R^x$ and $R^y$ may together form a 3- to 7-membered (e.g., 3- or 4-membered) ring, and each of $R^x$ and $R^y$ is optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl);

each of R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and n is 1 or 2, or a pharmaceutically acceptable form or an isotope derivative thereof, and a pharmaceutically acceptable excipient, carrier, or diluent.

In yet another aspect, the invention generally relates to a pharmaceutical composition comprising a compound having the structural formula (VII):

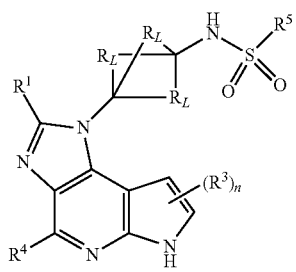

(VII)

wherein
R¹ is selected from hydrogen, $C_1$-$C_6$ (e.g., $C_1$-$C_3$) unsubstituted or substituted alkyl, OR', COOR' and CONR'R";

each R³ is independently selected from hydrogen, $C_1$-$C_6$ (e.g., $C_1$-$C_3$) unsubstituted or substituted alkyl, OR', COOR' and CONR'R";

R⁴ is a group selected from hydrogen (e.g., F, Cl), halogen, CN, $C_1$-$C_6$ (e.g., $C_1$-$C_3$) unsubstituted or substituted alkyl, OR', and NHR';

R⁵ is $R^x$ or $NR^xR^y$, wherein each of $R^x$ and $R^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and $R^x$ and $R^y$ may together form a 3- to 7-membered (e.g., 3- or 4-membered) ring, and optionally substituted with one or more of halogen (e.g., F, Cl), CN, OR', NR'R", alkyl (e.g., $C_1$-$C_6$ alkyl), haloalkyl (e.g., $CHF_2$, $CF_3$), cyanoalkyl (e.g., $CH_2CN$), hydroxyalkyl (e.g., $CH_2OH$) and alkoxyalkyl (e.g., $CH_2O$-alkyl); provided that when R⁵ is $R^x$, $R^x$ is not H (i.e., R⁵ is not H);

each $R_L$ is independently $(CH_2)_m$ and m is independently 0, 1, 2 or 3, wherein when m is 0, the respective bridge is absent;

each R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and n is 1 or 2, or a pharmaceutically acceptable form or an isotope derivative thereof, and a pharmaceutically acceptable excipient, carrier, or diluent.

In certain embodiments, a pharmaceutical composition herein disclosed is suitable for oral administration.

In certain embodiments, the pharmaceutical composition of the invention is suitable for topical administration.

In certain embodiments, a pharmaceutical composition herein disclosed is useful to treat or reduce one or more of inflammatory diseases, immune-mediated diseases and cancer, or a related disease or disorder.

In certain embodiments, a pharmaceutical composition herein disclosed is useful to treat or reduce one or more autoimmune diseases, or a related disease or disorder.

In certain embodiments of the pharmaceutical composition, the disease or disorder is selected from: asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS)), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating disease (CID), vascular diseases (e.g., autoimmune hearing loss, systemic vasculitis, and atherosclerosis), skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias), Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH), or a related disease or disorder thereof.

In yet another aspect, the invention generally relates to a unit dosage form comprising a pharmaceutical composition disclosed herein.

In certain embodiments, the unit dosage form is a solid dosage form, for example, in the forms of capsules, tablets, pills, powders or granules. In certain embodiments, the unit dosage form is a tablet. In certain embodiments, the unit dosage form is a capsule.

In certain embodiments, the unit dosage form is a liquid dosage form, for example, in the forms of emulsions, solutions, suspensions, syrups or elixirs.

In yet another aspect, the invention generally relates to a method for treating or reducing a disease or disorder, comprising: administering to a subject in need thereof a pharmaceutical composition comprising a compound having the structural formula (I):

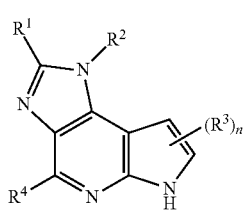

(I)

wherein
- R¹ is selected from hydrogen, $C_1$-$C_6$ (e.g., $C_1$-$C_3$) unsubstituted or substituted alkyl, OR', COOR' and CONR'R";
- R² is selected from $C_3$-$C_{10}$ (e.g., $C_3$-$C_6$) cycloalkyl, bicycloalkyl, spirocyclic or bridgedcycloalkyl, substituted with NR'C(=O)R$^x$, NR'C(=O)OR$^x$, NR'C(=O)NR$^x$R$^y$, C(=O)NR$^x$R$^y$, NR'SO$_2$R$^x$, NR'SO$_2$NR$^x$R$^y$, CR'R"SO$_2$R$^x$ or CR'R"SO$_2$NR$^x$R$^y$;
- each R³ is independently selected from hydrogen, $C_1$-$C_6$ (e.g., $C_1$-$C_3$) unsubstituted or substituted alkyl, OR', COOR' and CONR'R";
- R⁴ is a group selected from hydrogen, halogen, CN, $C_1$-$C_6$ (e.g., $C_1$-$C_3$) unsubstituted or substituted alkyl, OR', and NHR';
- each of R$^x$ and R$^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and R$^x$ and R$^y$ may together form a 3- to 7-membered (e.g., 3- or 4-membered) ring, and each of R$^x$ and R$^y$ is optionally substituted with one or more of halogen (e.g., F, Cl), CN, OR', NR'R", alkyl (e.g., $C_1$-$C_6$ alkyl), haloalkyl (e.g., CHF$_2$, CF$_3$), cyanoalkyl (e.g., CH$_2$CN), hydroxyalkyl (e.g., CH$_2$OH) and alkoxyalkyl (e.g., CH$_2$O-alkyl);
- each of R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and
- n is 1 or 2, or a pharmaceutically acceptable form or an isotope derivative thereof, effective to treat or reduce one or more of inflammatory diseases, immune-mediated diseases and cancer, or a related disease or disorder, in a mammal, including a human.

In yet another aspect, the invention generally relates to a method for treating or reducing a disease or disorder, comprising: administering to a subject in need thereof a pharmaceutical composition comprising a compound having the structural formula (VII):

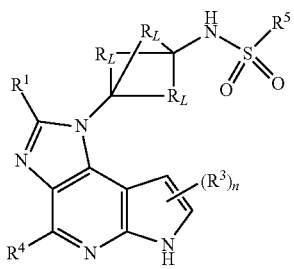

(VII)

wherein
- R¹ is selected from hydrogen, $C_1$-$C_6$ (e.g., $C_1$-$C_3$) unsubstituted or substituted alkyl, OR', COOR' and CONR'R";
- each R³ is independently selected from hydrogen, $C_1$-$C_6$ (e.g., $C_1$-$C_3$) unsubstituted or substituted alkyl, OR', COOR' and CONR'R";
- R⁴ is a group selected from hydrogen (e.g., F, Cl), halogen, CN, $C_1$-$C_6$ (e.g., $C_1$-$C_3$) unsubstituted or substituted alkyl, OR', and NHR';
- R⁵ is R$^x$ or NR$^x$R$^y$, wherein each of R$^x$ and R$^y$ is independently selected from H, alkyl (e.g., $C_1$-$C_6$ alkyl), cycloalkyl (e.g., $C_3$-$C_{10}$ cycloalkyl), heterocycloalkyl (e.g., $C_2$-$C_9$ heterocycloalkyl), aryl (e.g., $C_4$-$C_{10}$ aryl), heteroaryl (e.g., $C_3$-$C_9$ heteroaryl) and R$^x$ and R$^y$ may together form a 3- to 7-membered (e.g., 3- or 4-membered) ring, and optionally substituted with one or more of halogen (e.g., F, Cl), CN, OR', NR'R", alkyl (e.g., $C_1$-$C_6$ alkyl), haloalkyl (e.g., CHF$_2$, CF$_3$), cyanoalkyl (e.g., CH$_2$CN), hydroxyalkyl (e.g., CH$_2$OH) and alkoxyalkyl (e.g., CH$_2$O-alkyl); provided that when R⁵ is R$^x$, R$^x$ is not H (i.e., R⁵ is not H);
- each R$_L$ is independently (CH$_2$)$_m$ and m is independently 0, 1, 2 or 3, wherein when m is 0, the respective bridge is absent;
- each R' and R" is independently selected from hydrogen and $C_1$-$C_6$ (e.g., $C_1$-$C_3$) unsubstituted and substituted alkyl and R' and R" may together form a 3- to 7-membered (e.g., 3- or 4-membered) ring; and
- n is 1 or 2, or a pharmaceutically acceptable form or an isotope derivative thereof, and a pharmaceutically acceptable excipient, carrier, or diluent, effective to treat or reduce one or more of inflammatory diseases, immune-mediated diseases and cancer, or a related disease or disorder, in a mammal, including a human.

In yet another aspect, the invention generally relates to a method for treating or reducing a disease or disorder, comprising: administering to a subject in need thereof a pharmaceutical composition comprising a compound disclosed herein, wherein the disease or disorder is one or more of inflammatory diseases, immune-mediated diseases and cancer, or a related disease or disorder.

In certain embodiments, the method of the invention is useful for treating or reducing an autoimmune disease.

In certain embodiments, the disease or disorder is selected from: asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS)), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating disease (CID), vascular diseases (e.g., autoimmune hearing loss, systemic vasculitis, and atherosclerosis), skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias), Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH), or a related disease or disorder thereof.

In certain embodiments, the method of the invention is useful for treating or reducing an inflammatory disease, or a related disease or disorder.

In certain embodiments, the method of the invention is useful for treating or reducing an autoimmune disease, or a related disease or disorder.

In certain embodiments, the method of the invention is useful for treating or reducing an immune-mediated disease, or a related disease or disorder.

In certain embodiments, the method of the invention is useful for treating or reducing cancer, or a related disease or disorder.

In certain embodiments, the method of the invention is useful for treating or reducing one or more of rheumatoid arthritis, ankylosing spondylitis, psoriasis, atopic dermatitis, inflammatory bowel disease, Crohn's, ulcerative colitis, DES, vitiligo, alopecia areata, alopecia totalis.

In yet another aspect, the invention generally relates to use of a compound disclosed herein and a pharmaceutically acceptable excipient, carrier, or diluent, in preparation of a medicament for treating a disease or disorder.

In certain embodiments of such use, the disease or disorder is one or more of inflammatory diseases, immune-mediated diseases and cancer.

In certain embodiments of such use, the disease or disorder is an autoimmune disease.

In certain embodiments of such use, the disease or disorder is selected from: asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating disease (CID), vascular diseases (e.g., autoimmune hearing loss, systemic vasculitis, and atherosclerosis), skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias), Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH), or a related disease or disorder thereof.

In certain embodiments of such use, the disease or disorder is one or more of rheumatoid arthritis, ankylosing spondylitis, psoriasis, atopic dermatitis, inflammatory bowel disease, Crohn's, ulcerative colitis, DES, vitiligo, alopecia areata, alopecia totalis.

In certain embodiments of the use, the medicament is for oral administration.

In certain embodiments of the use, the medicament is for topical administration.

The term "inflammatory disease" refers to a disease or condition characterized by aberrant inflammation, e.g. an increased level of inflammation compared to a control such as a healthy person not suffering from a disease. Examples of inflammatory diseases that may be treated with a compound, pharmaceutical composition, or method described herein include autoimmune diseases, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound of the present disclosure may be particularly efficacious (due to, for example, limitations of current therapies) are described in more detail hereafter.

The term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include acne vulgaris, acute disseminated encephalomyelitis, acute necrotizing hemorrhagic leukoencephalitis, Addison's disease, agammaglobulinemia, Aicardi-Goutières syndrome (AGS), alopecia areata, alopecia totalis, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal or neuronal neuropathies, balo disease, Behcet's disease, bullous pemphigoid, cardiomyopathy, Castleman disease, celiac disease, Chagas disease, chronic atypical neutrophilic dermatosis with lipodystrophy and elevated temperature (CANDLE), chronic active hepatitis, chronic fatigue syndrome, chronic inflammatory demyelinating polyneuropathy, chronic recurrent multifocal ostomyelitis, Churg-Strauss syndrome, cicatricial pemphigoid/benign mucosal pemphigoid, Crohn's disease, Cogans syndrome, cold agglutinin disease, congenital heart block, coxsackie myocarditis, CREST disease, Cushing's disease, demyelinating neuropathies, depression, dermatitis herpetiformis, dermatomyositis, Devic's disease (neuromyelitis optica), discoid lupus, Dressler's syndrome, dry eye syndrome DES (keratoconjunctivitis sicca), endometriosis, eosinophilic esophagitis, eosinophilic fasciitis, erythema nodosum, essential mixed cryoglobulinemia, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, graft-versus-host disease (GVDH), Graves' disease, Guillain-Barre syndrome, Hashimoto's encephalitis, Hashimoto's thyroiditis, hemolytic anemia, Henoch-Schonlein purpura, herpes gestationis, hidradenitis suppurativa, hypogammaglobulinemia, idiopathic thrombocytopenic purpura, IgA nephropathy, IgG4-related sclerosing disease, inflammatory bowel disease (IBD), immunoregulatory lipoproteins, inclusion body myositis, interstitial cystitis, juvenile arthritis, juvenile diabetes (Type 1 diabetes), juvenile dermatomyositis (JDM), juvenile myositis, Kawasaki syndrome, Lambert-Eaton syndrome, leukocytoclastic vasculitis, lichen planus, lichen sclerosus, ligneous conjunctivitis, linear IgA disease, lupus, lyme disease, chronic, Meniere's disease, microscopic polyangiitis, mixed connective tissue disease, Mooren's ulcer, Mucha-Habermann disease, multiple sclerosis (MS), myasthenia gravis, myositis, narcolepsy, neuromyelitis optica, neutropenia, ocular cicatricial pemphigoid, optic neuritis, palindromic rheumatism, pediatric autoimmune neuropsychiatric disorders associated with streptococcus, paraneoplastic cerebellar degeneration, paroxysmal nocturnal hemoglobinuria p, Parry Romberg syndrome, Parsonnage-Turner syndrome, Pars planitis (peripheral uveitis), pemphigus, peripheral neuropathy, perivenous encephalomyelitis, pernicious anemia, POEMS syndrome, polyarteritis nodosa, polycystic ovary syndrome (PCOS), Type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, plaque psoriasis, idiopathic pulmonary fibrosis, pyoderma gangrenosum, pure red cell aplasia, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, stimulator of interferon genes (STING)-associated vasculopathy with onset during infancy (SAVI), subacute bacterial endocarditis, Susac's syndrome, sympathetic ophthalmia, systemic lupus erythematosus (SLE), Takayasu's arteritis, temporal arteritis/Giant cell arteritis, thrombocytopenic purpura, Tolosa-Hunt syndrome, transplant rejection (allograft transplant rejection), transverse myelitis, Type 1 diabetes, ulcerative colitis, undifferentiated connective tissue disease, uveitis, vasculitis, vesiculobullous dermatosis, vitiligo, or Wegener's granulomatosis.

The term "immune-mediated disease" refers to chronic inflammatory diseases perpetuated by antibodies and cellular immunity. Immune-mediated diseases include, for example, but not limited to, asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS)), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating disease (CID), vascular diseases (e.g., autoimmune hearing loss, systemic vasculitis, and atherosclerosis), and skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias). Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH).

The term "cancer" as used herein refers to all types of cancer, neoplasm or malignant tumors found in mammals, e.g., humans, including hematological cancers leukemia, and lymphomas, T-ALL, solid cancers such as carcinomas and sarcomas. Exemplary cancers include blood cancer, brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include myeloproliferative neoplasms, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

Isotopically-labeled compounds are also within the scope of the present disclosure. As used herein, an "isotopically-labeled compound" or "isotope derivative" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

By isotopically-labeling the presently disclosed compounds, the compounds may be useful in drug and/or substrate tissue distribution assays. Tritiated ($^3$H) and carbon-14 ($^{14}$C) labeled compounds are particularly preferred for their ease of preparation and detectability. Further, substitution with heavier isotopes such as deuterium ($^2$H) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen (H) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}$C with $^{13}$C. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to an adult human of 70 Kg may comprise about 0.001 mg to about 3,000 mg (e.g., about 0.001 mg to about 2,000 mg, about 0.001 mg to about 1,000 mg, about 0.001 mg to about 500 mg, about 0.001 mg to about 100 mg, about 0.001 mg to about 50 mg, about 0.001 mg to about 10 mg, about 0.01 mg to about 1,000 mg, about 0.1 mg to about 1,000 mg, about 1 mg to about 1,000 mg, about 10 mg to about 1,000 mg, about 100 mg to about 1,000 mg, about 1 mg to about 500 mg, about 5 μmg to about 250 mg) of a compound per unit dosage form.

In certain embodiments, a compound described herein may be administered at dosage levels sufficient to deliver from about 0.001 mg/Kg to about 1,000 mg/Kg (e.g., from about 0.01 mg/Kg to about 1,000 mg/Kg, from about 0.1 mg/Kg to about 1,000 mg/Kg, from about 1 mg/Kg to about 1,000 mg/Kg, from about 0.001 mg/Kg to about 100 mg/Kg, from about 0.001 mg/Kg to about 10 mg/Kg, from about 0.001 mg/Kg to about 1 mg/Kg, from about 0.1 mg/Kg to about 40 mg/Kg, from about 0.5 mg/Kg to about 30 mg/Kg, from about 0.01 mg/Kg to about 10 mg/Kg, from about 0.1 mg/Kg to about 10 mg/Kg, or from about 1 mg/Kg to about 25 mg/Kg) of subject body weight per day, one or more times a day, to obtain the desired therapeutic effect.

In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or pharmaceutical composition, as described herein, can be administered in combination with one or more additional therapeutically active agents. In certain embodiments, a compound or pharmaceutical composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or pharmaceutical composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will consider compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds, e.g., compounds approved by the U.S. Food and Drug Administration (FDA) as provided in the Code of Federal Regulations (CFR), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compounds or compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

The following examples are meant to be illustrative of the practice of the invention and not limiting in any way.

EXAMPLES

Abbreviations
  Certain abbreviations are listed below.
  Methanol: MeOH
  Dichloromethane: DCM
  Petroleum ether: PE
  Ethyl acetate: EtOAc
  Triethylamine: TEA
  Sodium hydroxide: NaOH
  Nitrogen: $N_2$
  Diphenyl phosphoryl azide: DPPA
  Thin-Layer Chromatography: TLC
  High Performance Liquid Chromatography: HPLC
  N,N-Diisopropylethylamine: DIPEA
  N,N-Dimethylformamide: DMF
  4-Methylbenzene-1-sulfonyl chloride: TsCl
  Room temperature: RT
  Hours: hrs
Representative Methods of Prep-HPLC: (Flow Rate and Gradient May Change)
  Exemplary methods for prep-HPLC are provided below.
  Method A: $NH_4HCO_3$:
(Column: XBrige Prep C18 5 µm OBD 19*150 mm, PN 186002979; mobile phase: $CH_3CN$ in water (0.1% $NH_4HCO_3$) from 20% to 60%, flow rate: 15 mL/min).

Method B:

(Column: XBridge Prep C18 5 μm OBD 19*150 mm, PN 186002979; mobile phase: CH₃CN in water (0.1% formic acid) from 15% to 40%, flow rate: 15 mL/min)

Representative Methods of Analytical-HPLC

Method 1: Analysis was performed on an Agilent 1260 series HPLC-6120MS. UHPLC Long Gradient Equivalent 5% to 95% acetonitrile (containing 0.02% NH₄OAc) in water run time of 6.5 minutes with a flow rate of 1.5 mL/min. A XBridge C18 column (5 μm, 4.6*50 mm; PN 186003113) was used at a temperature of 40° C.

Method 2: Analysis was performed on an Agilent 1200 series HPLC-6120MS. UHPLC Long Gradient Equivalent 5% to 95% acetonitrile (containing 0.1% trifluoroacetic acid) in water run time of 6.5 minutes with a flow rate of 1.5 mL/min. A XBridge C18 column (5 μm, 4.6*50 mm; PN 186003113) was used at a temperature of 40° C.

Method 3: Analysis was performed on an Agilent 1260 series HPLC-6120MS. UHPLC Long Gradient Equivalent 5% to 95% acetonitrile (containing 0.02% NH₄OAc) in water run time of 6.5 minutes with a flow rate of 2 mL/min. A Diamonsil Plus C18 column (5 μm, 4.6*30 mm Cat #99436) was used at a temperature of 40° C.

Example 1

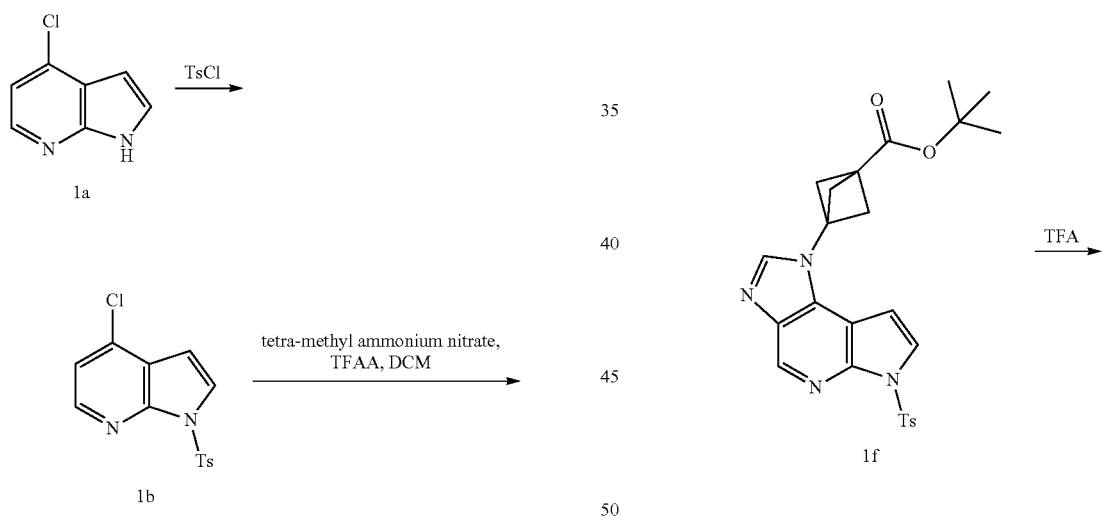

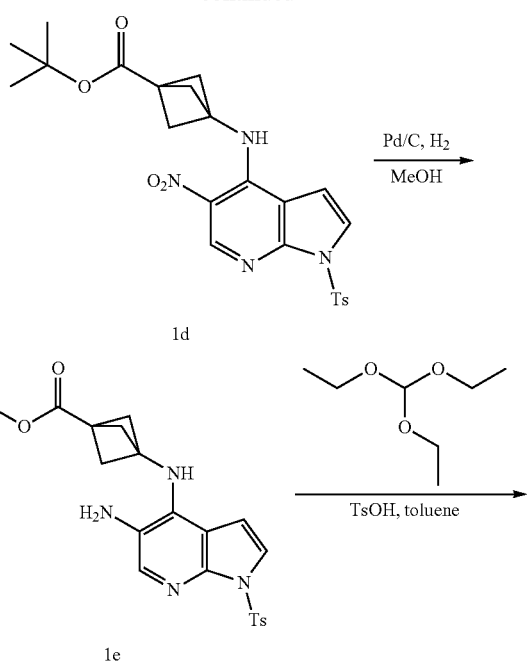

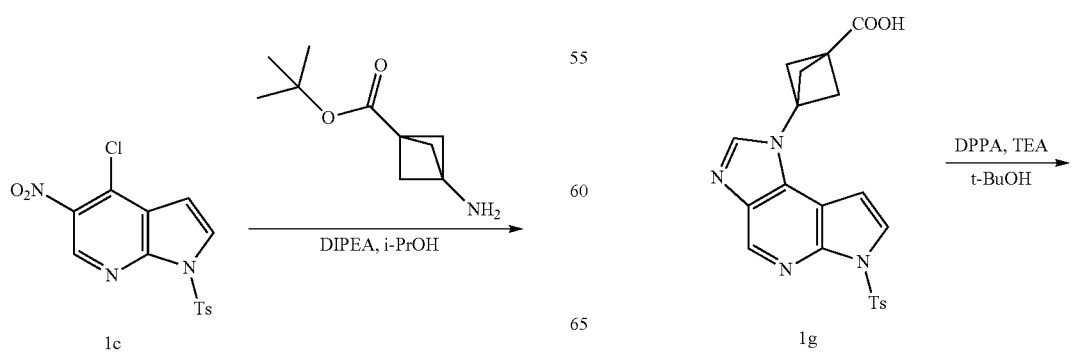

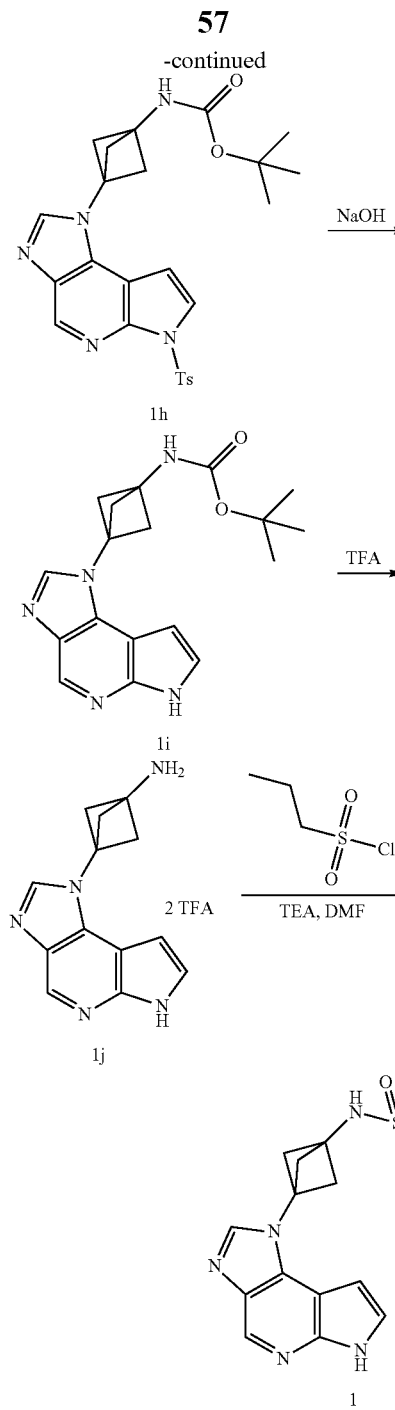

Step 1. 4-Chloro-1-tosyl-1H-pyrrolo[2,3-b]pyridine (1b)

Compound 1a (30 g, 0.2 mol) and TsCl (45 g, 0.24 mol) were dissolved in a mixture of acetone and water (600 mL, V:V=5:1) followed by the addition of NaOH (11.8 g, 0.29 mmol) at 0° C. After stirring at RT for 1 h, the mixture was concentrated to 100 mL of solvent and cooled with ice-water. The formed solid was filtered and dried to afford title product as a white solid (52 g, 86% yield). $^1$H NMR (400 MHz, CDCl$_3$) δ 8.30 (d, J=5.6 Hz, 1H), 8.05 (d, J=8.4 Hz, 2H), 7.76 (d, J=4.0 Hz, 1H), 7.27 (d, J=8.4 Hz, 2H), 7.18 (d, J=5.2 Hz, 1H), 6.69 (d, J=4.0 Hz, 1H), 2.37 (s, 3H).

Step 2. 4-Chloro-5-nitro-1-tosyl-1H-pyrrolo[2,3-b]pyridine (1c)

To a mixture of compound 1b (5.0 g, 16.3 mmol) and 75 mL of DCM was added tetrabutylammonium nitrate (2.9 g, 21.3 mmol) portion-wise at 0° C. followed by trifluoroacetic anhydride (3.14 mL, 22.2 mmol) slowly. After stirring for 16 hrs at RT, another portion of tetrabutylammonium nitrate (0.58 g, 4.23 mmol) and trifluoroacetic anhydride (0.8 mL, 5.7 mmol) were added at 0° C. After warmed up to room temperature, the reaction mixture was stirred for 4 hrs at RT. The reaction mixture was diluted with DCM (150 mL), washed with water (30 mL×2) and then concentrated to dryness. The residue was triturated in MeOH to afford title product as a white solid (3.15 g, 55% yield). LC-MS (Method 2): $t_R$=1.76 min, m/z (M+H)$^+$=351.8.

Step 3. Tert-butyl 3-((5-nitro-1-tosyl-1H-pyrrolo[2,3-b]pyridin-4-yl)amino)bicyclo[1.1.1]pentane-1-carboxylate (1d)

Compound 1c (500 mg, 1.42 mmol), tert-butyl 3-aminobicyclo[1.1.1]pentane-1-carboxylate (313 mg, 1.71 mmol) and DIPEA (276 mg, 2.13 mmol) were dissolved in isopropanol (5 μmL). The above solution was stirred at 120° C. for 2 hrs. After cooling, the formed solid was collected by filtering and dried to afford the title product as a brown solid (612 mg, 86% yield). $^1$H NMR (400 MHz, CDCl$_3$) δ 9.28 (s, 1H), 9.11 (s, 1H), 8.07 (d, J=8.0 Hz, 2H), 7.64 (d, J=5.6 Hz, 1H), 7.30 (d, J=8.0 Hz, 2H), 6.96 (d, J=5.6 Hz, 1H), 2.48 (s, 6H), 2.40 (s, 3H), 1.47 (s, 9H).

Step 4. Tert-butyl 3-((5-amino-1-tosyl-1H-pyrrolo[2,3-b]pyridin-4-yl)amino)bicyclo[1.1.1]pentane-1-carboxylate (1e)

Compound 1d (600 mg, 1.22 mmol) was dissolved in MeOH (6 mL) followed by the addition of Pd/C (48 mg, 10% wt) in one portion. The mixture was hydrogenated (1 atm) at RT for 16 hrs. The mixture was filtered and the filtrate was concentrated. The residue was purified by prep. TLC (PE:EtOAc=1:1) to afford the title product as a white solid (258 mg, 46% yield). LC-MS (Method 2): $t_R$=1.64 min, m/z (M+H)$^+$=469.0.

Step 5. Tert-butyl 3-(6-tosylimidazo[4,5-d]pyrrolo[2,3-b]pyridin-1(6H)-yl)bicyclo[1.1.1]pentane-1-carboxylate (1f)

Compound 1e (258 mg, 0.55 mmol), triethyl orthoformate (204 mg, 1.37 mmol) and p-toluenesulfonic acid (10 mg, 0.05 mmol) were dissolved in toluene (6 mL). The mixture was stirred for 16 hrs at 120° C. After cooling, the mixture was concentrated to dryness. The residue was purified by chromatography on silica gel (elute: PE:EtOAc=1:1) to afford the title product as a brown solid (191 mg, 73% yield). $^1$H NMR (400 MHz, CDCl$_3$) δ 8.91 (s, 1H), 8.10 (d, J=8.0 Hz, 2H), 7.82 (d, J=8.0 Hz, 2H), 7.27-7.25 (m, 2H), 6.83 (d, J=4.4 Hz, 1H), 2.71 (s, 6H), 2.35 (s, 3H), 1.51 (s, 9H).

Step 6. 3-(6-Tosylimidazo[4,5-d]pyrrolo[2,3-b]pyridin-1(6H)-yl)bicyclo[1.1.1]pentane-1-carboxylic acid (1g)

To a solution of compound 1f (191 mg, 0.40 mmol) in DCM (2 mL) was added TFA (1 mL). After stirring for 16 hrs at RT, the mixture was concentrated to dryness to afford crude title product as a brown solid (170 mg, 100% yield). LC-MS (Method 2): $t_R$=1.47 min, m/z (M+H)$^+$=423.0

Step 7. Tert-butyl (3-(6-tosylimidazo[4,5-d]pyrrolo [2,3-b]pyridin-1(6H)-yl)bicyclo[1.1.1]pentan-1-yl) carbamate (1h)

To a mixture of compound 1g (153 mg, 0.36 mmol) in tert-butanol (7.2 mL) was added DPPA (130 mg, 0.47 mmol) and TEA (73 mg, 0.72 mmol) under N$_2$. The mixture was stirred at RT for 30 minutes and then raised to 90° C. and stirred for another 16 hrs. After cooling, the mixture was concentrated to dryness. The residue was purified by chromatography on silica gel (elute: DCM:MeOH=50:1) to afford the title product as a brown solid (160 mg, 89% yield). LC-MS (Method 2): $t_R$=1.71 min, m/z (M+H)$^+$=494.0.

Step 8. Tert-butyl (3-(imidazo[4,5-d]pyrrolo[2,3-b] pyridin-1(6H)-yl)bicyclo[1.1.1]pentan-1-yl)carbamate (1i)

To a solution of compound 1h (160 mg, 0.32 mmol) in MeOH (3 mL) and water (3 mL) was added NaOH (300 mg, 7.5 mmol). After stirring for 4 hrs at RT, the mixture was concentrated. The residue was diluted with water (20 mL) and extracted with EtOAc (30 mL*2). The combined organic layers were concentrated to dryness and the residue was purified by chromatography on silica gel (elute: DCM: MeOH=20:1) to afford the title product as a white solid (60 mg, 55% yield). $^1$H NMR (400 MHz, CDCl$_3$) δ 9.99 (s, 1H), 9.81 (s, 1H), 7.80 (s, 1H), 7.39 (d, J=4.4 Hz, 1H), 6.36 (d, J=4.4 Hz, 1H), 5.30 (br s, 1H), 2.80 (s, 6H), 1.50 (s, 9H).

Step 9. 3-(Imidazo[4,5-d]pyrrolo[2,3-b]pyridin-1 (6H)-yl)bicyclo[1.1.1]pentan-1-amine 2,2,2-trifluoroacetate (1j)

To a solution of compound 1i (60 mg, 0.18 mmol) in DCM (2 mL) was added TFA (0.5 mL). After stirring for 1 hour at RT, the mixture was concentrated to dryness to afford crude title product as a brown solid (100 mg, 100% yield). LC-MS (Method 2): $t_R$=0.309 min, m/z (M+H)$^+$=240.0

Step 10. N-(3-(Imidazo[4,5-d]pyrrolo[2,3-b]pyridin-1(6H)-yl)bicyclo[1.1.1]pentan-1-yl)propane-1-sulfonamide (1)

To a solution of compound 1j (40 mg, 0.16 mmol) and TEA (51 mg, 50 mmol) in DMF (1 mL) was added propane-1-sulfonyl chloride (28 mg, 0.5 mmol) at 0° C. After stirring for 3 hrs at RT, the mixture was diluted with water (20 mL) and extracted with EtOAc (20 mL*3). The combined organic layers were concentrated to dryness. The residue was purified prep. HPLC (Method A) to afford the title product as a white solid (10 mg, 18% yield). LC-MS (Method 1): $t_R$=2.71 min, m/z (M+H)$^+$=346.0. $^1$H NMR (400 MHz, DMSO-d$_6$) δ 11.94 (s, 1H), 8.59 (d, J=1.6 Hz, 1H), 8.40 (s, 1H), 8.13 (s, 1H), 7.51 (s, 1H), 6.70 (d, J=1.6 Hz, 1H), 3.08 (d, J=8.8 Hz, 2H), 2.70 (s, 6H), 1.74-1.72 (m, 2H), 1.73 (d, J=6.0 Hz, 3H).

Example 2

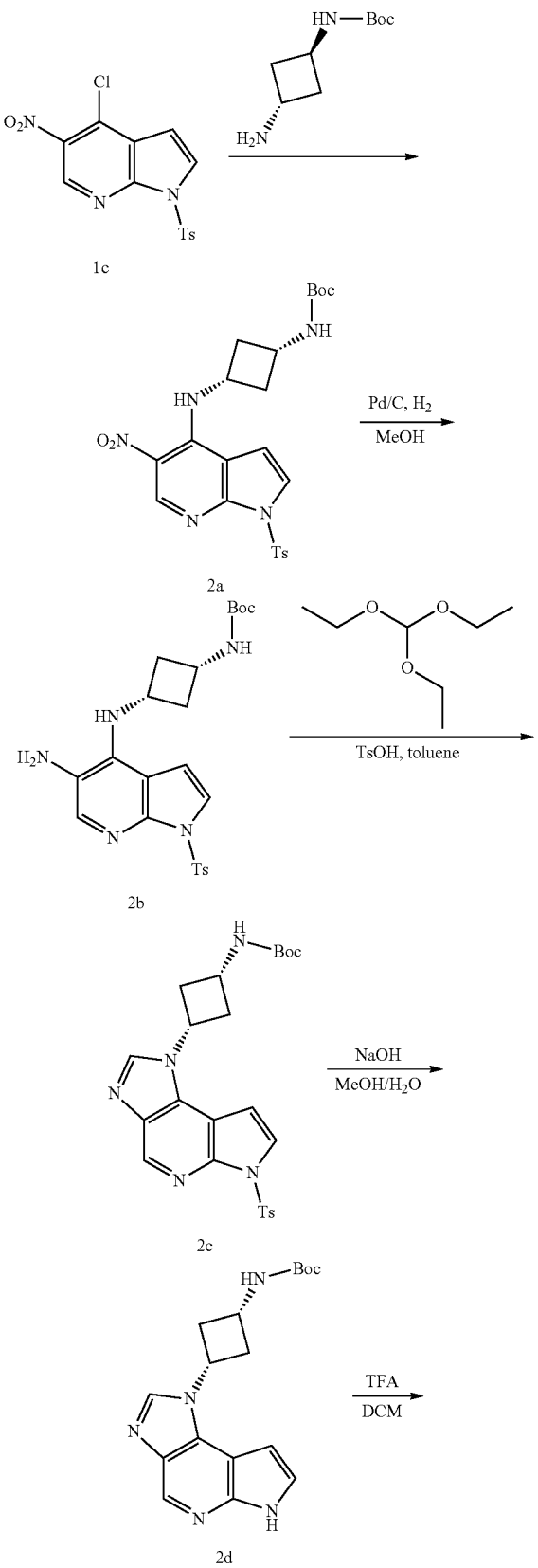

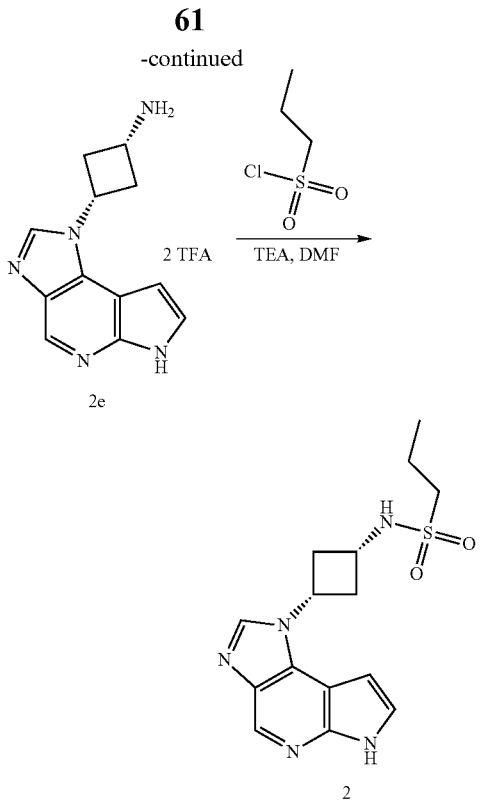

Step 1. Tert-butyl (cis-3-((5-nitro-1-tosyl-1H-pyrrolo[2,3-b]pyridin-4-yl)amino)cyclobutyl)carbamate (2a)

Compound 2a (380 mg) was synthesized in 89% yield by utilizing similar preparative procedure of the third step of example 1 with compound 1c (300 mg, 0.85 mmol) and tert-butyl (cis-3-aminocyclobutyl)carbamate (191 mg, 1.02 mmol) as starting materials. $^1$H NMR (400 MHz, CDCl$_3$) δ 9.09 (s. 1H), 9.04 (d, J=6.8 Hz, 1H), 8.06 (d, J=8.4 Hz, 2H), 7.60 (d, J=4.4 Hz, 1H), 7.30 (d, J=8.4 Hz, 2H), 6.75 (d, J=4.4 Hz, 1H), 4.73 (br s, 1H), 4.07 (br s, 1H), 3.04-2.92 (m, 2H), 2.41 (s, 3H), 2.03-1.94 (m, 2H), 1.40 (s, 9H).

Step 2. Tert-butyl (cis-3-((5-amino-1-tosyl-1H-pyrrolo[2,3-b]pyridin-4-yl)amino)cyclobutyl)carbamate (2b)

Compound 2b (300 mg) was synthesized in 84% yield by utilizing similar preparative procedure of the fourth step of example 1 with compound 2a (380 mg, 0.76 mmol) as starting materials. LC-MS (Method 1): $t_R$=1.63 min, m/z (M+H)$^+$=472.2

Step 3. Tert-butyl (cis-3-(6-tosylimidazo[4,5-d]pyrrolo[2,3-b]pyridin-1(6H)-yl)cyclobutyl)carbamate (2c)

Compound 2c (260 mg) was synthesized in 85% yield by utilizing similar preparative procedure of the fifth step of example 1 with compound 2b (300 mg, 0.64 mmol) and triethoxymethane (236 mg, 1.59 mmol) as starting materials. $^1$H NMR (400 MHz, CDCl$_3$) δ 9.90 (s, 1H), 8.10 (d, J=8.4 Hz, 2H), 8.05 (s, 1H), 7.80 (d, J=4.0 Hz, 1H), 7.25 (d, J=8.4 Hz, 2H), 6.77 (d, J=4.0 Hz, 1H), 4.73 (br s, 1H), 4.73-4.69 (m, 1H), 4.16-4.14 (m, 1H), 3.18-3.12 (m, 2H), 2.47-2.44 (m, 2H), 2.34 (s, 3H), 1.45 (s, 9H).

Step 4. Tert-butyl (cis-3-(imidazo[4,5-d]pyrrolo[2,3-b]pyridin-1(6H)-yl)cyclobutyl)carbamate (2d)

Compound 2d (165 mg) was synthesized in 93% yield by utilizing similar preparative procedure of the eighth step of example 1 with compound 2c (260 mg, 0.54 mmol) as starting materials. LC-MS (Method 1): $t_R$=1.47 min, m/z (M+H)$^+$=328.1.

Step 5. Cis-3-(imidazo[4,5-d]pyrrolo[2,3-b]pyridin-1(6H)-yl)cyclobutanamine 2,2,2-trifluoroacetate (2e)

Compound 2e (199 mg crude) was synthesized in 87% yield by utilizing similar preparative procedure of the ninth step of example 1 with compound 2d (165 mg, 0.50 mmol) as starting materials. LC-MS (Method 1): $t_R$=0.22 min, m/z (M+H)$^+$=228.0.

Step 6. N-(Cis-3-(imidazo[4,5-d]pyrrolo[2,3-b]pyridin-1(6H)-yl)cyclobutyl)propane-1-sulfonamide 2

Example 2 (28.8 mg) was synthesized in 25% yield by utilizing similar preparative procedure of the final step of example 1 with compound 2e (160 mg crude, 0.35 mmol) and propane-1-sulfonyl chloride (60 mg, 0.42 mmol) as starting materials. LC-MS (Method 1): $t_R$ 2.84 min, m/z (M+H)$^+$=334.1. $^1$H NMR (400 MHz, DMSO-d$_6$) δ 11.85 (s, 1H), 8.57 (s, 1H), 8.35 (s, 1H), 7.58 (d, J=8.8 Hz, 1H), 7.46 (t, J=2.8 Hz, 1H), 7.58 (dd, J=3.6, 2.0 Hz, 1H), 4.95-4.90 (m, 1H), 3.86-3.80 (m, 1H), 3.10-3.24 (m, 2H), 3.00-2.96 (m, 2H), 2.54-2.47 (m, 2H), 1.73-1.67 (m, 2H), 0.99 (t, J=7.2 Hz, 3H).

Example 3

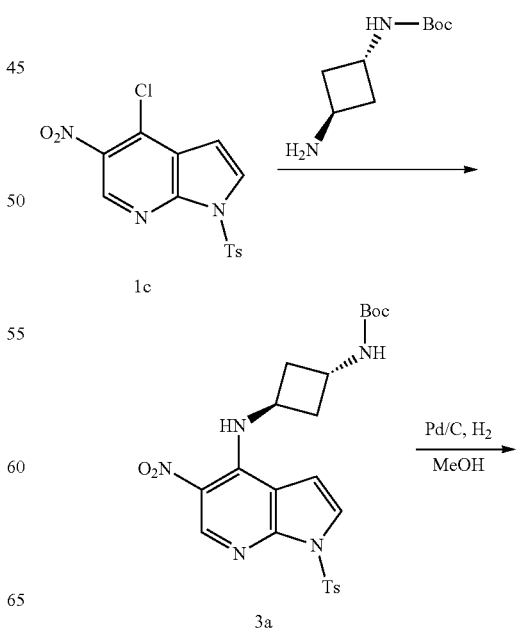

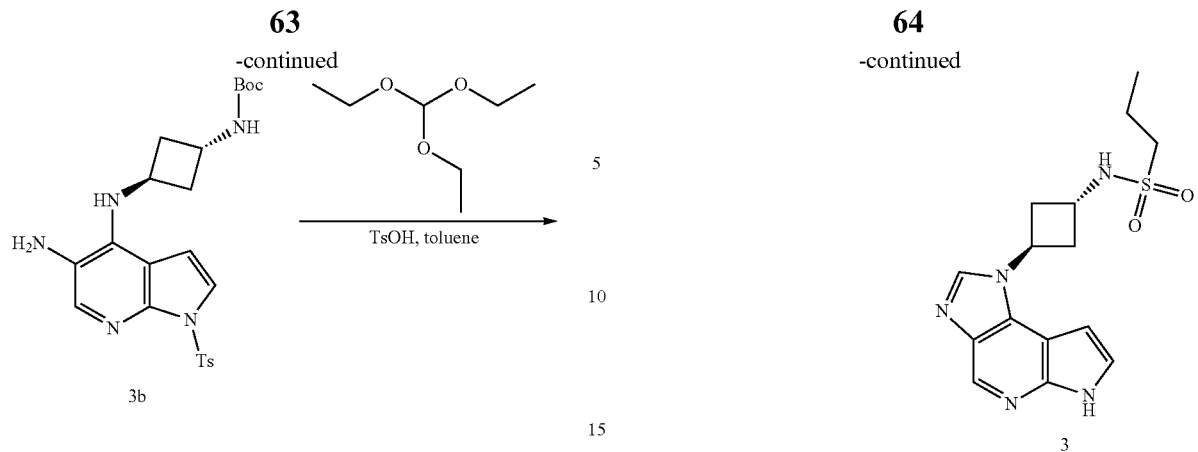

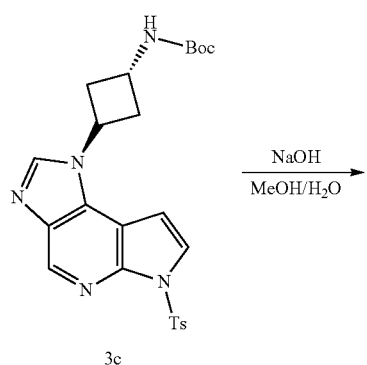

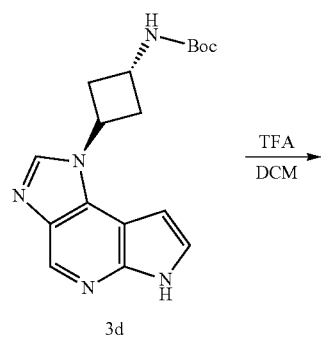

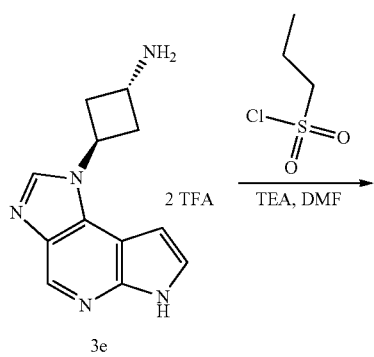

Step 1. Tert-butyl (trans-3-((5-nitro-1-tosyl-1H-pyrrolo[2,3-b]pyridin-4-yl)amino)cyclobutyl)carbamate (3a)

Compound 3a (0.64 g) was synthesized in 89% yield by utilizing similar preparative procedure of the first step of example 2 with compound 1c (500 mg, 1.42 mmol) and tert-butyl (trans-3-aminocyclobutyl)carbamate (318 mg, 1.71 mmol) as starting materials. $^1$H NMR (400 MHz, CDCl$_3$) δ 9.16 (d, J=5.2 Hz, 1H), 9.11 (s, 1H), 8.06 (d, J=8.4 Hz, 2H), 7.57 (d, J=4.0 Hz, 1H), 7.31 (d, J=8.4 Hz, 2H), 6.61 (d, J=4.0 Hz, 1H), 4.81 (br s, 1H), 4.50 (br s, 1H), 4.33 (br s, 1H), 2.57-2.46 (m, 4H), 2.40 (s, 3H), 1.45 (s, 9H).

Step 2. Tert-butyl (trans-3-((5-amino-1-tosyl-1H-pyrrolo[2,3-b]pyridin-4-yl)amino)cyclobutyl)carbamate (3b)

Compound 3b (0.45 g) was synthesized in 75% yield by utilizing similar preparative procedure of the second step of example 2 with compound 3a (0.64 g, 1.28 mmol) as starting materials. LC-MS (Method 1): $t_R$=1.61 min, m/z (M+H)$^+$=472.2.

Step 3. Tert-butyl (trans-3-(6-tosylimidazo[4,5-d]pyrrolo[2,3-b]pyridin-1(6H)-yl)cyclobutyl)carbamate (3c)

Compound 3c (160 mg) was synthesized in 35% yield by utilizing similar preparative procedure of the third step of example 2 with compound 3b (0.45 g, 0.95 mmol) and triethoxymethane (432 mg, 2.91 mmol) as starting materials. $^1$H NMR (400 MHz, CDCl$_3$) δ 9.91 (s, 1H), 8.11-8.07 (m, 3H), 7.79 (d, J=4.0 Hz, 1H), 7.26-7.22 (m, 2H), 6.70 (d, J=4.0 Hz, 1H), 5.21-5.14 (m, 1H), 4.90 (br s, 1H), 4.37 (br s, 1H), 2.93-2.86 (m, 2H), 2.79-2.73 (m, 2H), 2.35 (s, 3H), 1.46 (s, 9H).

Step 4. Tert-butyl (trans-3-(imidazo[4,5-d]pyrrolo[2,3-b]pyridin-1(6H)-yl)cyclobutyl)carbamate (3d)

Compound 3d (100 mg) was synthesized in 92% yield by utilizing similar preparative procedure of the fourth step of example 2 with compound 3c (160 mg, 0.33 mmol) as starting materials. LC-MS (Method 1): $t_R$=1.32 min, m/z (M+H)$^+$=328.2.

Step 5. Trans-3-(imidazo[4,5-d]pyrrolo[2,3-b]pyridin-1(6H)-yl)cyclobutanamine 2,2,2-trifluoroacetate 3e Compound 3e (60 mg crude) was synthesized in 43% yield by utilizing similar preparative procedure of the fifth step of example 2 with compound 3d (100 mg, 0.31 mmol) as starting materials. The crude product was used for next step directly without further purification.

Step 6. N-(trans-3-(imidazo[4,5-d]pyrrolo[2,3-b]pyridin-1(6H)-yl)cyclobutyl)propane-1-sulfonamide (3)

Example 3 (29.6 mg) was synthesized in 34% yield by utilizing similar preparative procedure of the final step of example 2 with compound 3e (60 mg, 0.26 mmol) and propane-1-sulfonyl (45 mg, 0.31 mmol) chloride as starting materials. LC-MS (Method 1): $t_R$=2.68 min, m/z (M+H)$^+$=334.0. $^1$H NMR (400 MHz, DMSO-$d_6$) δ 11.84 (s, 1H), 8.58 (s, 1H), 8.51 (s, 1H), 7.84 (d, J=8.0 Hz, 1H), 7.46 (t, J=2.8 Hz, 1H), 6.72 (dd, J=3.2, 2.0 Hz, 1H), 5.34-5.27 (m, 1H), 4.10-4.05 (m, 1H), 3.02-2.90 (m, 4H), 2.73-2.66 (m, 2H), 1.73-1.64 (m, 2H), 0.98 (t, J=7.2 Hz, 3H).

Example 4

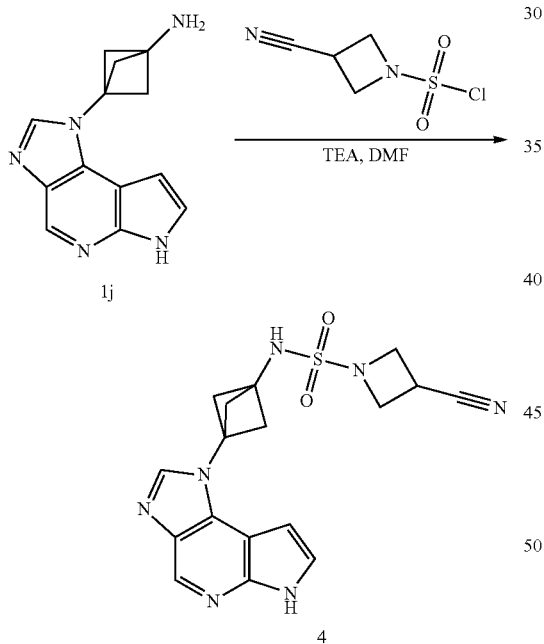

3-Cyano-N-(3-(imidazo[4,5-d]pyrrolo[2,3-b]pyridin-1(6H)-yl)bicyclo[1.1.1]pentan-1-yl)azetidine-1-sulfonamide (4)

Example 4 (22.6 mg) was synthesized in 28% yield by utilizing similar preparative procedure of the final step of example 1 with compound 1j (50 mg, 0.21 mmol) and 3-cyanoazetidine-1-sulfonyl chloride (45 mg, 0.25 mmol) as starting materials. LC-MS (Method 1): $t_R$=3.01 min, m/z (M+H)$^+$=384.1. $^1$H NMR (400 MHz, DMSO-$d_6$) δ 11.92 (s, 1H), 8.75 (s, 1H), 8.59 (s, 1H), 8.12 (s, 1H), 7.50 (t, J=2.8 Hz, 1H), 6.68 (dd, J=1.6, 3.2 Hz, 1H), 4.07 (t, J=8.4 Hz, 2H), 3.94 (t, J=6.0 Hz, 2H), 3.81-3.77 (m, 1H), 2.70 (s, 6H).

Example 5

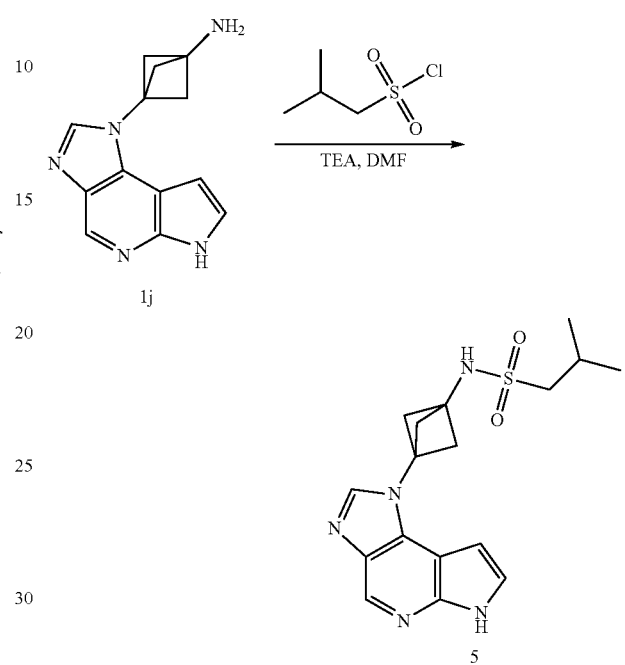

N-(3-(imidazo[4,5-d]pyrrolo[2,3-b]pyridin-1(6H)-yl)bicyclo[1.1.1]pentan-1-yl)-2-methylpropane-1-sulfonamide (5)

Example 5 (6.9 mg) was synthesized in 11% yield by utilizing similar preparative procedure of the final step of example 1 with compound 1j (43 mg, 0.18 mmol) and 2-methylpropane-1-sulfonyl chloride (34 mg, 0.22 mmol) as starting materials. LC-MS (Method 1): $t_R$=3.10 min, m/z (M+H)$^+$=360.1. $^1$H NMR (400 MHz, DMSO-$d_6$) δ 11.97 (s, 1H), 8.62 (s, 1H), 8.44 (s, 1H), 8.16 (s, 1H), 7.54 (t, J=3.6 Hz, 1H), 6.72 (d, J=1.6 Hz, 1H), 3.04 (d, J=8.4 Hz, 2H), 2.73 (s, 6H), 2.22-2.13 (m, 1H), 1.10 (d, J=8.8 Hz, 6H).

Example 6

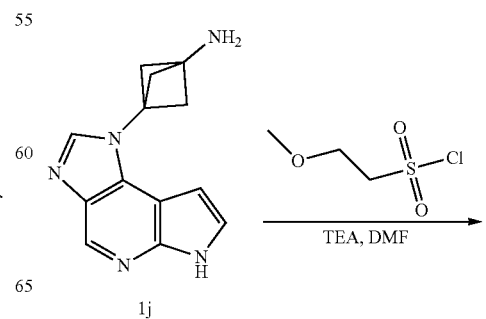

-continued

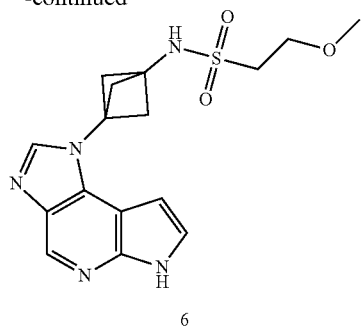

6

N-(3-(imidazo[4,5-d]pyrrolo[2,3-b]pyridin-1(6H)-yl)bicyclo[1.1.1]pentan-1-yl)-2-methoxyethanesulfonamide (6)

Example 6 (21.1 mg) was synthesized in 31% yield by utilizing similar preparative procedure of the final step of example 1 with compound 1j (45 mg, 0.19 mmol) and 2-methoxyethanesulfonyl chloride (36 mg, 0.23 mmol) as starting materials. LC-MS (Method 1): $t_R$=2.48 min, m/z (M+H)$^+$=362.1. $^1$H NMR (400 MHz, DMSO-$d_6$) δ 11.91 (s, 1H), 8.59 (s, 1H), 8.42 (s, 1H), 8.11 (s, 1H), 7.50 (t, J=2.8 Hz, 1H), 6.69 (dd, J=1.6, 3.2 Hz, 1H), 3.72 (t, J=6.4 Hz, 2H), 3.38 (t, J=6.4 Hz, 2H), 3.37 (s, 3H), 2.70 (s, 6H).

Example 7

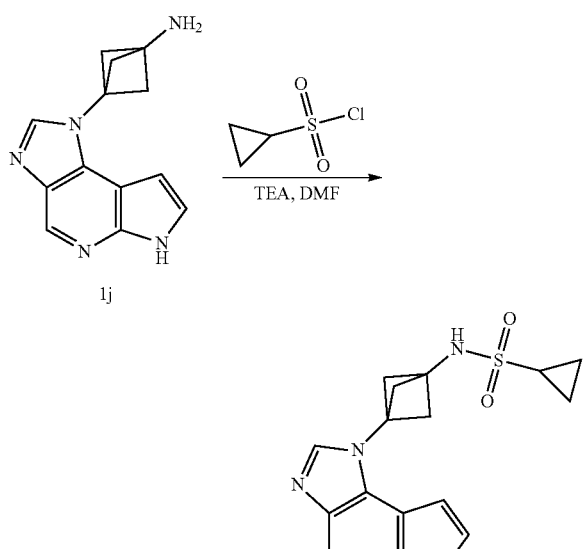

N-(3-(imidazo[4,5-d]pyrrolo[2,3-b]pyridin-1(6H)-yl)bicyclo[1.1.1]pentan-1-yl)cyclopropanesulfonamide (7)

Example 7 (15.5 mg) was synthesized in 25% yield by utilizing similar preparative procedure of the final step of example 1 with compound 1j (43 mg, 0.18 mmol) and cyclopropanesulfonyl chloride (30 mg, 0.21 mmol) as starting materials. LC-MS (Method 1): $t_R$=3.02 min, m/z (M+H)$^+$=344.1. $^1$H NMR (400 MHz, DMSO-$d_6$) δ 11.92 (s, 1H), 8.59 (s, 1H), 8.38 (s, 1H), 8.12 (s, 1H), 7.50 (t, J=2.8 Hz, 1H), 6.69 (dd, J=1.6, 3.2 Hz, 1H), 2.71 (s, 6H), 2.69-2.67 (m, 1H), 1.05-1.00 (m, 4H).

Example 8

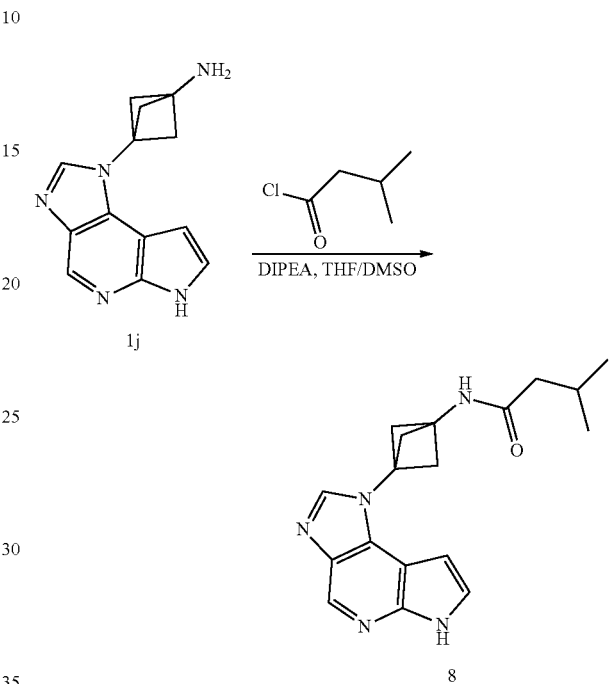

8

N-(3-(Imidazo[4,5-d]pyrrolo[2,3-b]pyridin-1(6H)-yl)bicyclo[1.1.1]pentan-1-yl)-3-methylbutanamide (8)

Example 8 (17.3 mg) was synthesized in 26% yield by utilizing similar preparative procedure of the final step of example 1 with compound 1j (50 mg, 0.21 mmol) and 3-methylbutanoyl chloride (38 mg, 0.31 mmol) as starting materials. LC-MS (Method 1): $t_R$=2.43 min, m/z (M+H)$^+$=324.2. $^1$H NMR (400 MHz, DMSO-$d_6$) δ 11.90 (s, 1H), 8.65 (s, 1H), 8.59 (s, 1H), 8.11 (s, 1H), 7.49 (t, J=3.2 Hz, 1H), 6.69 (dd, J=2.0, 3.6 Hz, 1H), 2.72 (s, 6H), 2.00-1.99 (m, 3H), 0.90 (d, J=6.4 Hz, 6H).

Example 9

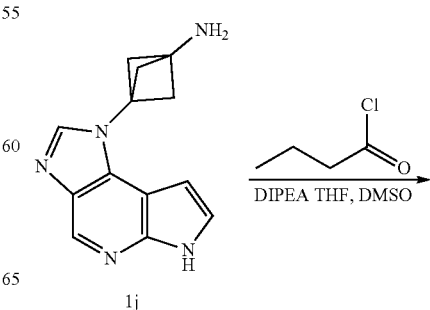

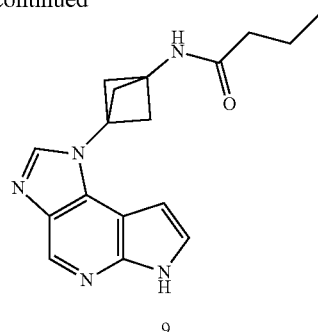

9

N-(3-(imidazo[4,5-d]pyrrolo[2,3-b]pyridin-1(6H)-yl)bicyclo[1.1.1]pentan-1-yl)butyramide (9)

Example 9 (12.4 mg) was synthesized in 14% yield by utilizing similar preparative procedure of the final step of example 1 with compound 1j (50 mg, 0.21 mmol) and butyryl chloride (53 mg, 0.32 mmol) as starting materials. The final compound was purified by prep-HPLC (Method B). LC-MS (Method 1): $t_R$=3.06 min, m/z (M+H)$^+$=310.2. $^1$H NMR (400 MHz, DMSO-d$_6$) δ 12.28 (s, 1H), 8.77 (s, 1H), 8.69 (s, 1H), 8.51 (s, 1H), 7.63 (s, 1H), 6.82 (s, 1H), 2.75 (s, 6H), 2.09 (t, J=7.6 Hz, 2H), 1.58-1.49 (m, 2H), 0.87 (t, J=7.2 Hz, 3H).

Example 10

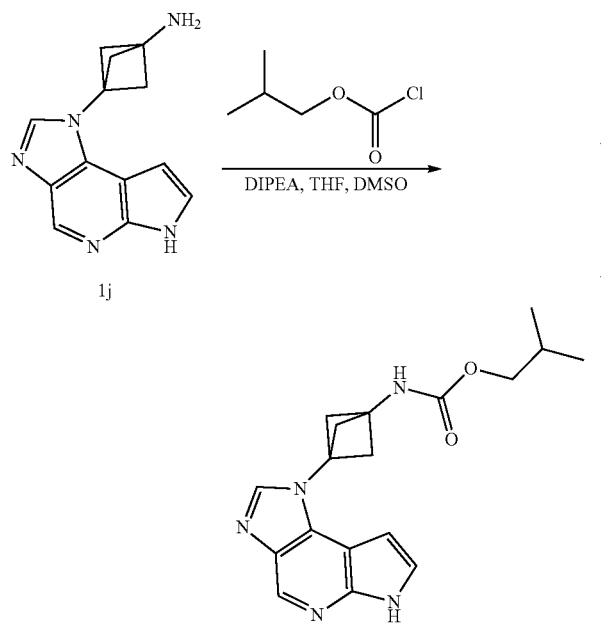

Isobutyl (3-(imidazo[4,5-d]pyrrolo[2,3-b]pyridin-1(6H)-yl)bicyclo[1.1.1]pentan-1-yl)carbamate (10)

Example 10 (2.3 mg) was synthesized in 3% yield by utilizing similar preparative procedure of the final step of example 1 with compound 1j (50 mg, 0.21 mmol) and isobutyl carbonochloridate (31 mg, 0.230 mmol) as starting materials. LC-MS (Method 1): $t_R$=3.38 min, m/z (M+H)$^+$=340.2. $^1$H NMR (400 MHz, CD$_3$OD) δ 8.49 (s, 1H), 8.03 (s, 1H), 7.38 (d, J=3.6 Hz, 1H), 6.76 (s, 1H), 3.77 (s, 2H), 2.72 (s, 6H), 1.91-1.78 (m, 1H), 0.88 (d, J=5.2 Hz, 6H).

Example 11

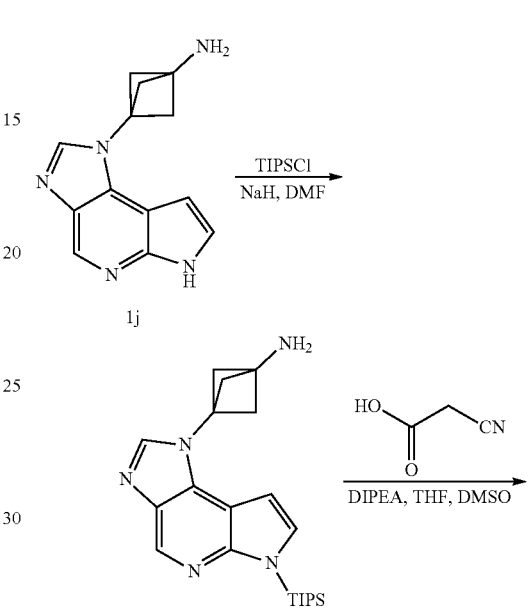

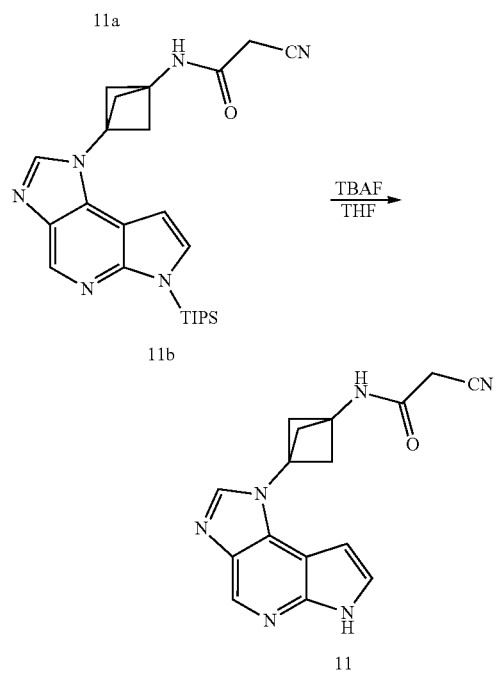

Step 1. 3-(6-(Triisopropylsilyl)imidazo[4,5-d]pyrrolo[2,3-b]pyridin-1(6H)-yl)bicyclo[1.1.1]pentan-1-amine (11a)

To a solution of compound 1j (200 mg, 0.84 mmol) in DMF (2 mL) was added NaH (100 mg, 2.56 mmol, 60% in mineral oil) at 0° C. The mixture was stirred at 0° C. for 1 h. TIPSCl (240 mg, 1.28 mmol) was added to the reaction mixture at 0° C. After stirring for 4 hrs, the mixture was diluted with H$_2$O (30 mL) and extracted with EtOAc (50 mL). The separated organic layer was concentrated and the residue was purified by prep-HPLC (Method A) to afford the title product as colorless oil (150 mg, 45% yield). LC-MS (Method 3): t$_R$=1.94 min, m/z (M+H)$^+$=396.2.

Step 2. 2-Cyano-N-(3-(6-(triisopropylsilyl)imidazo [4,5-d]pyrrolo[2,3-b]pyridin-1(6H)-yl)bicyclo[1.1.1] pentan-1-yl)acetamide (11b)

To a solution of compound 11a (150 mg, 0.39 mmol), 2-cyanoacetic acid (65 mg, 0.76 mmol) in DMF (2 mL) was added HATU (433 mg, 1.14 mmol) and DIPEA (147 mg, 1.14 mmol) at RT. The mixture was stirred at RT for 2 h. The mixture was concentrated and the residue was purified by Prep-HPLC (Method A) to afford the title compound (150 mg, 83% yield) as a white solid. LC-MS (Method 3): t$_R$=1.87 min, m/z (M+H)$^+$=463.2.

Step 3. 2-Cyano-N-(3-(imidazo[4,5-d]pyrrolo[2,3-b] pyridin-1(6H)-yl)bicyclo[1.1.1]pentan-1-yl)acet- amide (11)

To a solution of Compound 11b (150 mg, 0.32 mmol) in THF (4 mL) was added TBAF (0.49 ml, 0.49 mmol) at RT. The mixture was stirred at RT for 1 h. The mixture was concentrated and the residue was purified by prep-HPLC (Method A) to afford the title product as a white solid (33 mg, 34% yield). LC-MS (Method 1): t$_R$=2.89 min, m/z (M+H)$^+$=307.1. $^1$H NMR (400 MHz, DMSO-d$_6$) δ 11.91 (s, 1H), 9.18 (s, 1H), 8.59 (s, 1H), 8.12 (s, 1H), 7.50 (t, J=2.8 Hz, 1H), 6.69 (dd, J=2.0, 3.6 Hz, 1H), 3.70 (s, 2H), 2.75 (s, 6H).

Example 12

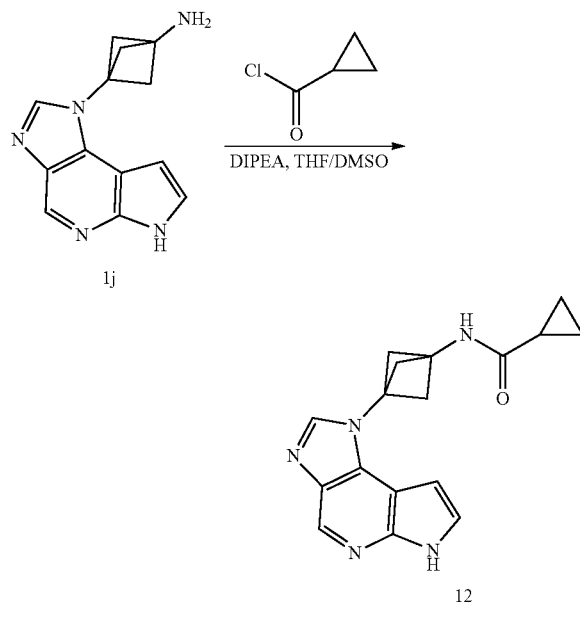

N-(3-(Imidazo[4,5-d]pyrrolo[2,3-b]pyridin-1(6H)-yl) bicyclo[1.1.1]pentan-1-yl)cyclopropanecarboxamide (12)

Example 12 (6 mg) was synthesized in 9% yield by utilizing similar preparative procedure of the final step of example 1 with compound 1j (50 mg, 0.21 mmol) and cyclopropanecarbonyl chloride (33 mg, 0.31 mmol) as starting materials. LC-MS (Method 1): t$_R$=3.23 min, m/z (M+H)$^+$=308.1. $^1$H NMR (400 MHz, DMSO-d$_6$) δ 11.90 (s, 1H), 8.97 (s, 1H), 8.59 (s, 1H), 8.12 (s, 1H), 7.49 (t, J=3.2 Hz, 1H), 6.70 (dd, J=1.6, 3.2 Hz, 1H), 2.73 (s, 6H), 1.58-1.54 (m, 1H), 0.74-0.69 (m, 4H).

Example 13

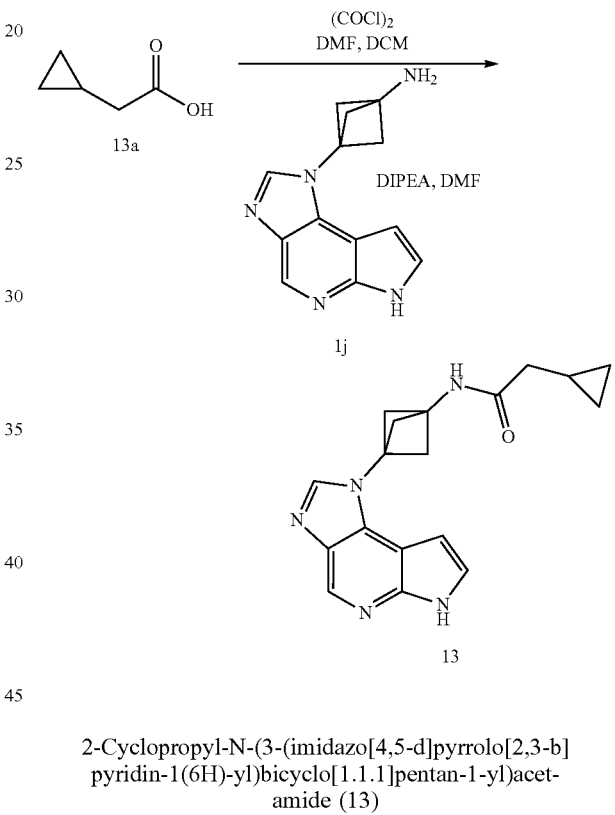

2-Cyclopropyl-N-(3-(imidazo[4,5-d]pyrrolo[2,3-b] pyridin-1(6H)-yl)bicyclo[1.1.1]pentan-1-yl)acet- amide (13)

To a solution of 2-cyclopropylacetic acid (200 mg, 2.0 mmol) in DCM (2 mL) was dropwise added DMF (1 drop) and oxalyl chloride (508 mg, 4.0 mmol) at 0° C. The mixture was stirred at RT for 1 h. The mixture was concentrated in vacuo to give 2-cyclopropylacetyl chloride (236 mg, crude) as a white solid.

To a solution of compound 1j (50 mg, 0.21 mmol) and DIPEA (270 mg, 2.1 mmol) in DMF (1 mL) was added 2-cyclopropylacetyl chloride (37.2 mg, 0.315 mmol) at 0° C. The mixture was stirred at RT for 3 hrs. The mixture was purified by prep-HPLC (Method B) to give the title compound (30 mg, 44% yield) as a white solid. LC-MS (Method 1): t$_R$=2.96 min, m/z (M+H)$^+$=322.2; $^1$H NMR (400 MHz, DMSO-d$_6$) δ 12.23 (s, 1H), 8.74 (s, 1H), 8.63 (s, 1H), 8.45 (s, 1H), 7.61 (t, J=2.8 Hz, 1H), 6.81 (s, 1H), 2.76 (s, 6H), 2.03 (d, J=7.2 Hz, 2H), 1.01-0.95 (m, 1H), 0.48-0.44 (m, 2H), 0.13 (dd, J$_1$=5.2 Hz, J$_2$=10.0 Hz, 2H).

Example 14

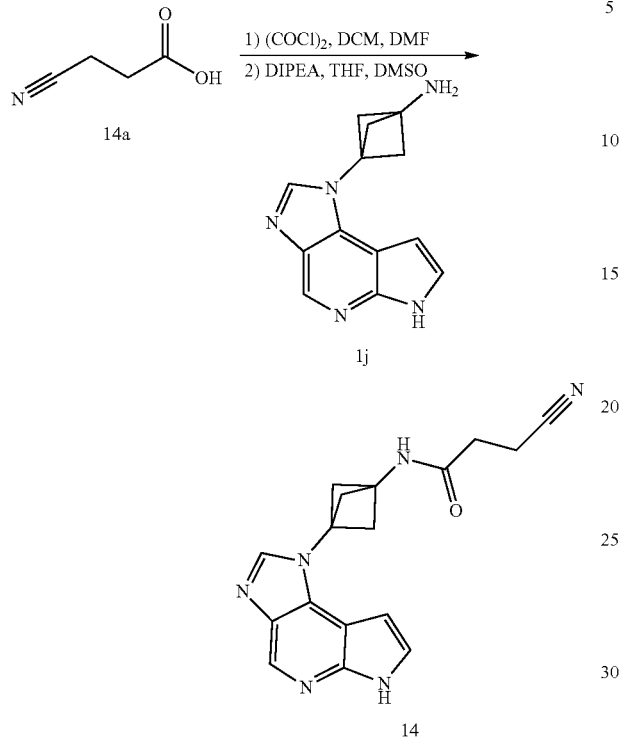

3-Cyano-N-(3-(imidazo[4,5-d]pyrrolo[2,3-b]pyridin-1(6H)-yl)bicyclo[1.1.1]pentan-1-yl)propanamide (14)

Example 14 (8.8 mg) was synthesized in 13% yield by utilizing similar preparative procedure of example 13 with compound 1j (50 mg, 0.21 mmol) and 3-cyanopropanoic acid (69 mg, 0.69 mmol) as starting materials. LC-MS (Method 1): $t_R$=2.84 min, m/z (M+H)$^+$=321.1. $^1$H NMR (400 MHz, DMSO-$d_6$) δ 11.92 (s, 1H), 8.93 (s, 1H), 8.59 (s, 1H), 8.13 (s, 1H), 7.50 (t, J=2.4 Hz, 1H), 6.70 (d, J=1.6 Hz, 1H), 2.74 (s, 6H), 2.66 (t, J=7.2 Hz, 2H), 2.44-2.39 (m, 2H).

Example 15

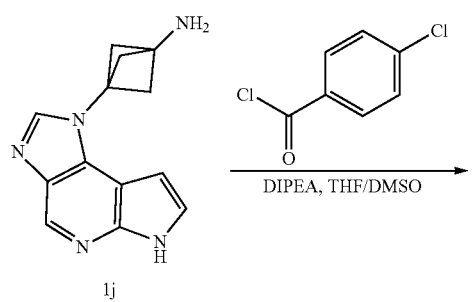

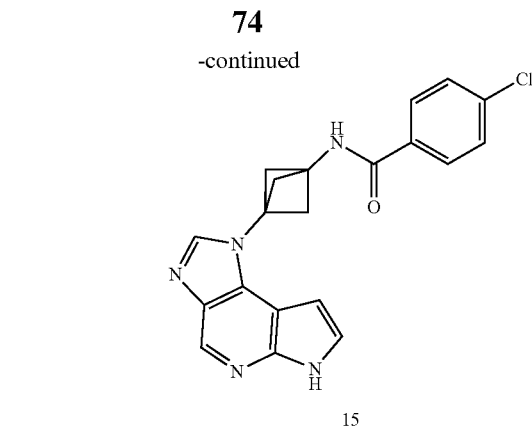

4-Chloro-N-(3-(imidazo[4,5-d]pyrrolo[2,3-b]pyridin-1(6H)-yl)bicyclo[1.1.1]pentan-1-yl)benzamide (15)

Example 15 (15 mg) was synthesized in 19% yield by utilizing similar preparative procedure of the final step of example 1 with compound 1j (50 mg, 0.21 mmol) and 4-chlorobenzoyl chloride (54 mg, 0.31 mmol) as starting materials. LC-MS (Method 1): $t_R$=3.48 min, m/z (M+H)$^+$=378.1. $^1$H NMR (400 MHz, DMSO-$d_6$) δ 11.92 (s, 1H), 9.41 (s, 1H), 8.60 (s, 1H), 8.17 (s, 1H), 7.93 (d, J=8.4 Hz, 2H), 7.58 (d, J=8.4 Hz, 2H), 7.51 (t, J=3.2 Hz, 1H), 6.73 (dd, J=1.6, 3.2 Hz, 1H), 2.84 (s, 6H).

Example 16

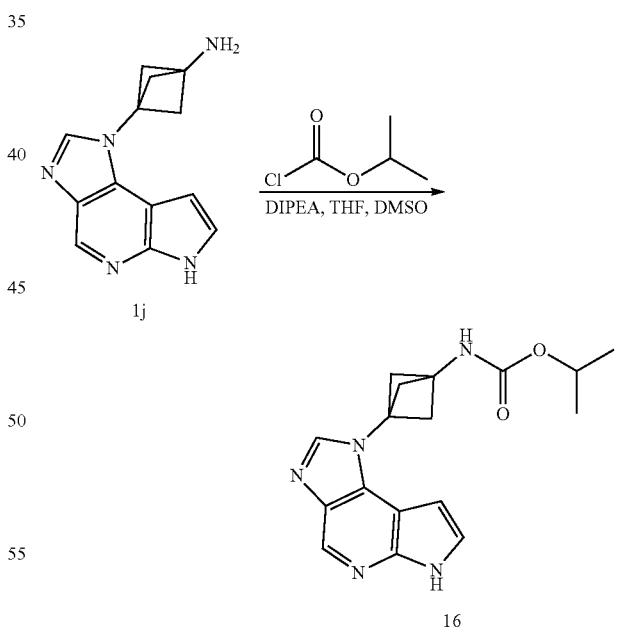

Isopropyl (3-(imidazo[4,5-d]pyrrolo[2,3-b]pyridin-1(6H)-yl)bicyclo[1.1.1]pentan-1-yl)carbamate (16)

Example 16 (15.3 mg) was synthesized in 21% yield by utilizing similar preparative procedure of the final step of example 1 with compound 1j (55 mg, 0.23 mmol) and isopropyl chloroformate (0.23 mL, 1 mol/L, 0.23 mmol) as starting materials. LC-MS (Method 1): $t_R$=2.79 min, m/z (M+H)$^+$=326.2. $^1$H NMR (400 MHz, DMSO-d$_6$) δ 11.91 (s, 1H), 8.58 (s, 1H), 8.11 (s, 1H), 8.07 (br s, 1H), 7.49 (t, J=3.2 Hz, 1H), 6.68 (dd, J=1.6, 3.2 Hz, 1H), 4.83-4.77 (m, 1H), 2.67 (s, 6H), 1.21 (d, J=5.6 Hz, 6H).

Example 17

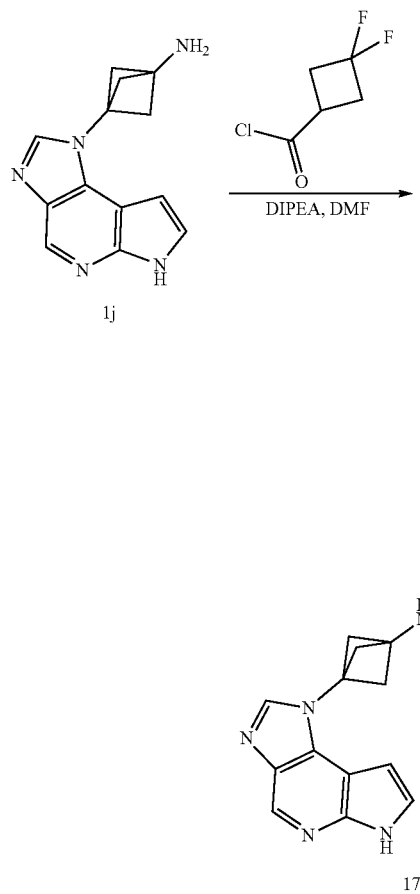

3,3-Difluoro-N-(3-(imidazo[4,5-d]pyrrolo[2,3-b]pyridin-1(6H)-yl)bicyclo[1.1.1]pentan-1-yl)cyclobutanecarboxamide (17)

Example 17 (3.7 mg) was synthesized in 4% yield by utilizing similar preparative procedure of the final step of example 1 with compound 1j (50 mg, 0.21 mmol) and 3,3-difluorocyclobutanecarbonyl chloride (49 mg, 0.32 mmol) as starting materials. The title compound was purification by Prep-HPLC (Method B). LC-MS (Method 1): $t_R$=3.11 min, m/z (M+H)$^+$=358.2. $^1$H NMR (400 MHz, DMSO-d$_6$) δ 11.91 (s, 1H), 8.95 (s, 1H), 8.59 (s, 1H), 8.12 (s, 1H), 7.49 (t, J=2.8 Hz, 1H), 6.70 (dd, J=1.6, 3.2 Hz, 1H), 2.89-2.87 (m, 1H), 2.76-2.68 (m, 10H).

Example 18

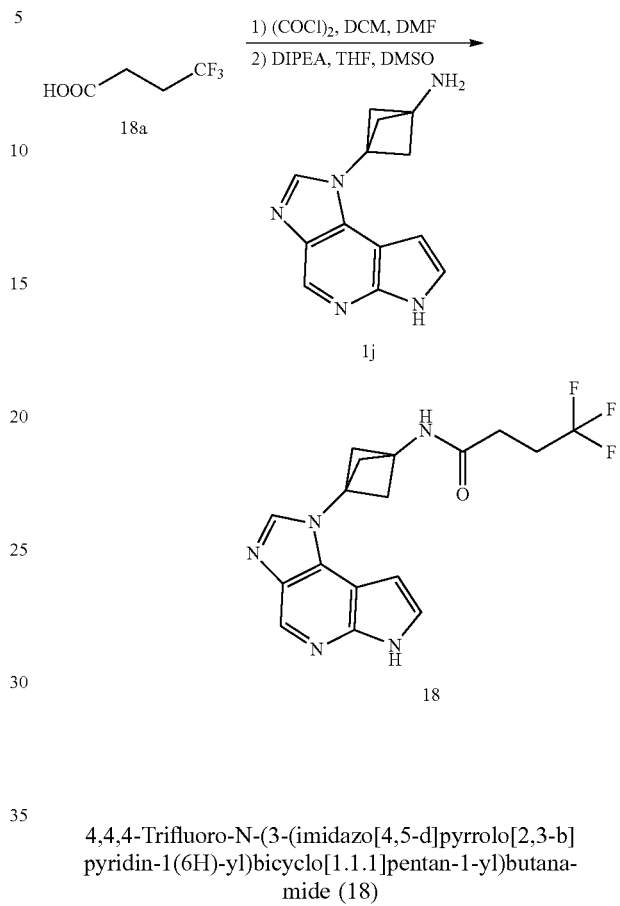

4,4,4-Trifluoro-N-(3-(imidazo[4,5-d]pyrrolo[2,3-b]pyridin-1(6H)-yl)bicyclo[1.1.1]pentan-1-yl)butanamide (18)

Example 18 (29.9 mg) was synthesized in 39% yield by utilizing similar preparative procedure of example 13 with compound 1j (50 mg, 0.21 mmol) and 4,4,4-trifluorobutanoic acid (60 mg, 0.42 mmol) as starting materials. LC-MS (Method 1): $t_R$=2.82 min, m/z (M+H)$^+$=364.1. $^1$H NMR (400 MHz, DMSO-d$_6$) δ 11.91 (s, 1H), 8.91 (s, 1H), 8.59 (s, 1H), 8.12 (s, 1H), 7.49 (t, J=2.8 Hz, 1H), 6.69 (dd, J=2.0 Hz, 3.6 Hz, 1H), 2.73 (s, 6H), 2.57-2.52 (m, 2H), 2.42-2.39 (m, 2H).

Example 19

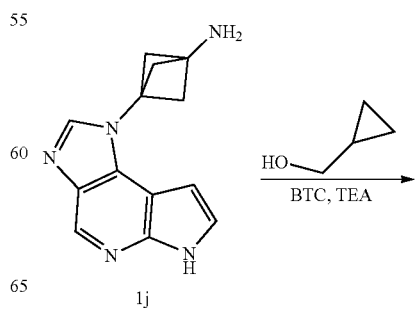

-continued

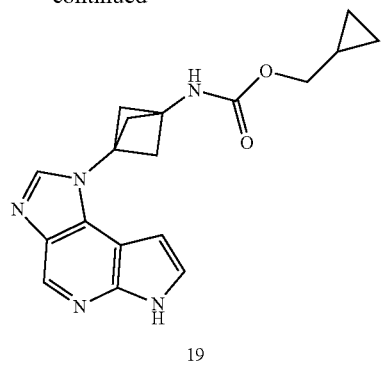

19

Cyclopropylmethyl (3-(imidazo[4,5-d]pyrrolo[2,3-b]pyridin-1(6H)-yl)bicyclo[1.1.1]pentan-1-yl)carbamate (19)

Cyclopropylmethanol (30 mg, 0.42 mmol) and TEA (63 mg, 0.63 mmol) were dissolved in THF (1 mL). The resulting solution was cooled down to −30° C. followed by dropwise added a solution of bis(trichloromethyl) carbonate (124 mg, 0.42 mmol) in THF (1 mL) at the same temperature. The reaction was warmed to RT and stirred for 30 mins. Then a solution of compound 1j (50 mg, 0.21 mmol) and TEA (63 mg, 0.63 mmol) in THF/DMSO (1 mL/0.5 mL) was added to the above reaction mixture. After stirring at RT for 1 h, the mixture was diluted with DCM (10 mL) and washed with brine (5 μmL). The organic layer was separated and concentrated to give a residue which was purified by Prep-HPLC (Method A) to afford the title product as a white solid (2.4 mg, 3% yield). LC-MS (Method 1): $t_R$=8.49 min, m/z (M+H)$^+$=338.2. $^1$H NMR (400 MHz, CD$_3$OD) δ 8.58 (s, 1H), 8.12 (s, 1H), 7.47 (d, J=3.6 Hz, 1H), 6.86 (d, J=3.2 Hz, 1H), 3.92 (s, 2H), 2.81 (s, 6H), 1.17-1.15 (m, 1H), 0.59-0.57 (m, 2H), 0.32-0.30 (m, 2H).

Example 20

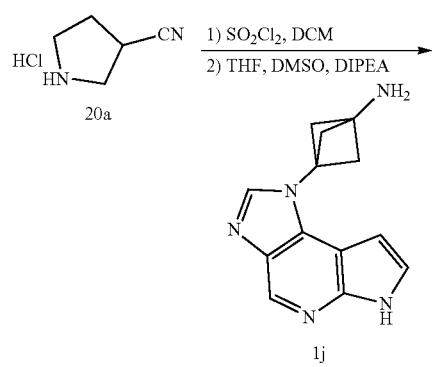

-continued

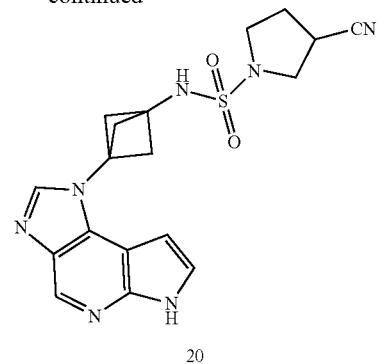

20

3-Cyano-N-(3-(imidazo[4,5-d]pyrrolo[2,3-b]pyridin-1(6H)-yl)bicyclo[1.1.1]pentan-1-yl)pyrrolidine-1-sulfonamide (20)

Compound 20a (100 mg, 0.76 mmol) and TEA (267 mg, 2.64 mmol) were dissolved in DCM (2 mL) followed by dropwise added a solution of SO$_2$Cl$_2$ (122 mg, 0.91 mmol) in 6.0 mL DCM at −78° C. The mixture was stirred at −78° C. for 30 mins and warmed to RT. Aq. HCl (1 N, 10 mL) and brine (10 mL) were added to the above solution. The separated organic layer was dried over Na$_2$SO$_4$ and filtered. The filtrate was concentrated to dryness to afford a brown oil. Then it was dissolved in DCM (0.5 ml). The resulting solution was added to a mixture of compound 1j (80 mg, 0.335 mmol) and DIPEA (130 mg, 1.005 mmol) in THF (2 mL) and DMSO (0.4 mL) at RT. The reaction was stirred at room temperature for 18 hrs. The mixture was diluted with water (20 mL) and extracted with EtOAc (30 mL*3). The combined organic layers were dried over Na$_2$SO$_4$ and filtered. The filtrate was concentrated to dryness to give a residue which was purified by prep-HPLC (Method A) to afford the title product as a yellow solid (12 mg, 9% yield). LC-MS (Method 1): $t_R$=2.96 min, m/z (M+H)$^+$=398.1. $^1$H NMR (400 MHz, DMSO-d$_6$) δ 11.94 (s, 1H), 8.63 (s, 1H), 8.59 (s, 1H), 8.12 (s, 1H), 7.51-7.49 (m, 1H), 6.68-6.67 (m, 1H), 3.52-3.49 (m, 2H), 3.44-3.41 (m, 1H), 3.29-3.27 (m, 2H), 2.71-2.68 (m, 6H), 2.34-2.29 (m, 1H), 2.22-2.16 (m, 1H).

Example 21

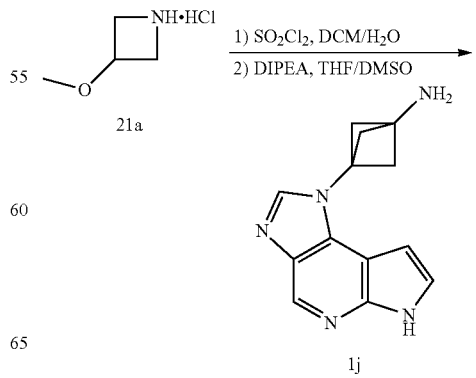

-continued

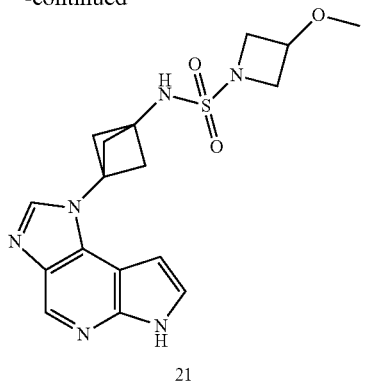

21

N-(3-(imidazo[4,5-d]pyrrolo[2,3-b]pyridin-1(6H)-yl)
bicyclo[1.1.1]pentan-1-yl)-3-methoxyazetidine-1-
sulfonamide (21)

Example 21 (13 mg) was synthesized in 16% yield by utilizing similar preparative procedure of example 20 with compound 1j (50 mg, 0.21 mmol) and compound 21a (150 mg, 1.21 mmol) as starting materials. LC-MS (Method 1): $t_R$=2.87 min, m/z (M+H)$^+$=389.2. $^1$H NMR (400 MHz, DMSO-d$_6$) δ 11.93 (s, 1H), 8.60 (s, 1H), 8.52 (s, 1H), 8.13 (s, 1H), 7.51 (s, 1H), 6.67 (s, 1H), 4.18 (s, 1H), 3.95 (d, J=6.4 Hz, 2H), 3.66-2.65 (m, 2H), 3.23 (s, 3H), 2.69 (s, 6H).

Example 22

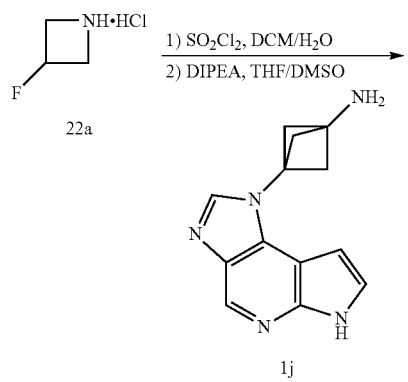

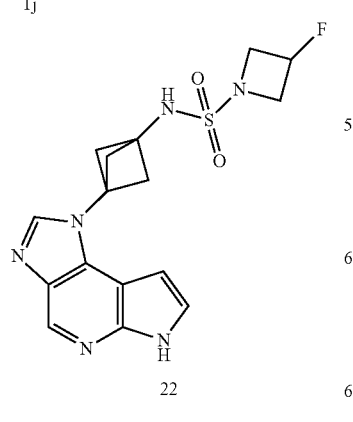

22

3-Fluoro-N-(3-(imidazo[4,5-d]pyrrolo[2,3-b]pyridin-
1(6H)-yl)bicyclo[1.1.1]pentan-1-yl)azetidine-1-
sulfonamide (22)

Example 22 (13 mg) was synthesized in 16% yield by utilizing similar preparative procedure of example 20 with compound 1j (50 mg, 0.21 mmol) and compound 22a (200 mg, 1.79 mmol) as starting materials. LC-MS (Method 1): $t_R$=2.88 min, m/z (M+H)$^+$=377.1. $^1$H NMR (400 MHz, DMSO-d$_6$) δ 11.94 (s, 1H), 8.69 (s, 1H), 8.59 (s, 1H), 8.13 (s, 1H), 7.51 (t, J=3.2 Hz, 1H), 6.67 (d, J=0.8 Hz, 1H), 5.47-5.44 (m, 0.5H), 5.32-5.30 (m, 0.5H), 4.15-4.06 (m, 2H), 3.93-3.84 (m, 2H), 2.69 (s, 6H).

Example 23

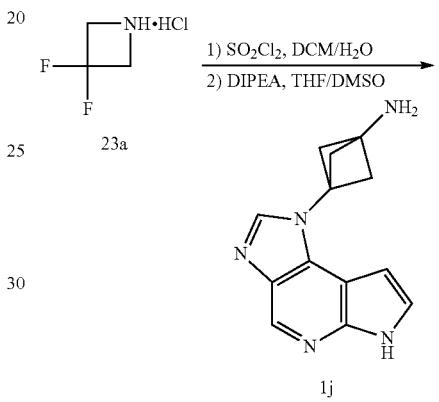

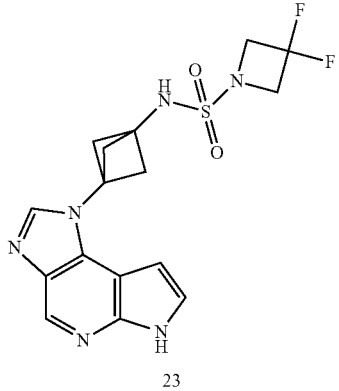

23

3,3-difluoro-N-(3-(imidazo[4,5-d]pyrrolo[2,3-b]
pyridin-1(6H)-yl)bicyclo[1.1.1]pentan-1-yl)azeti-
dine-1-sulfonamide (23)

Example 23 (8.0 mg) was synthesized in 10% yield by utilizing similar preparative procedure of example 20 with compound 1j (50 mg, 0.21 mmol) and compound 23a (200 mg, 1.54 mmol) as starting materials. LC-MS (Method 1): $t_R$=3.15 min, m/z (M+H)$^+$=395.1. $^1$H NMR (400 MHz, DMSO-d$_6$) δ 11.93 (s, 1H), 8.93 (s, 1H), 8.60 (s, 1H), 8.13 (s, 1H), 7.51 (t, J=2.8 Hz, 1H), 6.67 (dd, J=1.6, 3.2 Hz, 1H), 4.29 (t, J=12.8 Hz, 4H), 2.68 (s, 6H).

Example 24

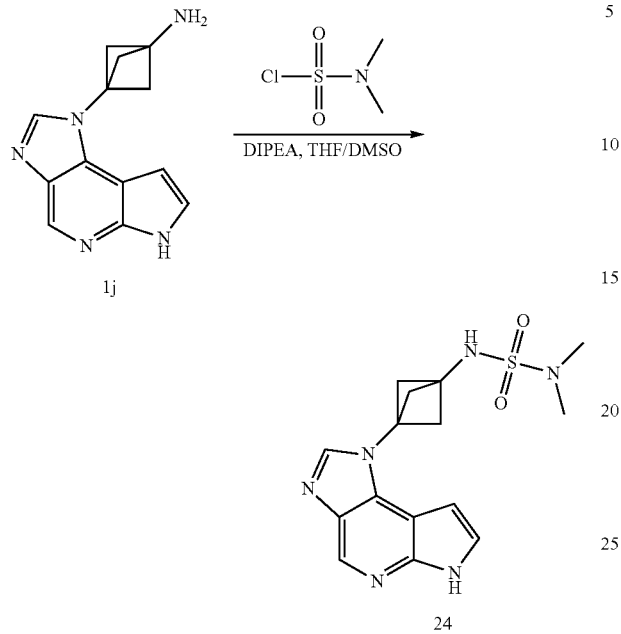

1j

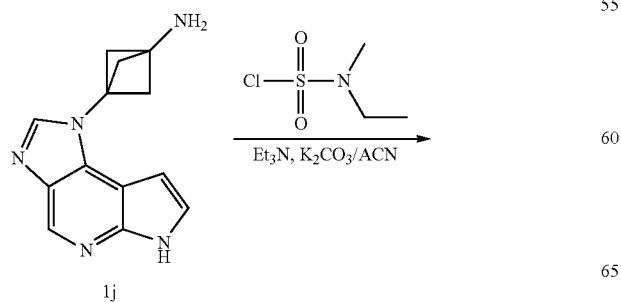

24

N-(3-(imidazo[4,5-d]pyrrolo[2,3-b]pyridin-1(6H)-yl)
bicyclo[1.1.1]pentan-1-yl)-N'-dimethyl-1-sulfona-
mide (24)

To a solution of compound 1j (60 mg, 0.25 mmol) and DIPEA (130 mg, 1.00 mmol) in THF (1.5 mL) and DMSO (0.5 mL) was dropwise added a solution of dimethylsulfamoyl chloride (36 mg, 0.25 mmol) in 0.5 mL THF at 0° C. The mixture was stirred at 25° C. for 14 hrs. The mixture was diluted with $H_2O$ (15 mL) and extracted with DCM (20 mL*2). The combined organic layers were concentrated and the residue was purified by prep-HPLC (Method A) to afford the title product as a white solid (15 mg, 17% yield). LC-MS (Method 1): $t_R$=2.59 min, m/z (M+H)$^+$=347.1. $^1$H NMR (400 MHz, $CD_3OD$) δ 8.48 (s, 1H), 8.02 (s, 1H), 7.38 (d, J=3.6 Hz, 1H), 6.71 (d, J=3.2 Hz, 1H), 2.73 (s, 6H), 2.68 (s, 6H).

Example 25

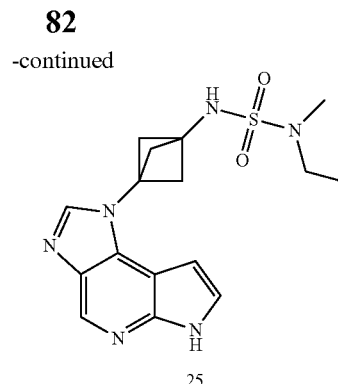

1j

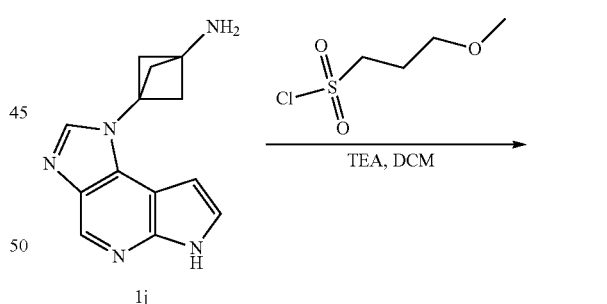

25

N-(3-(imidazo[4,5-d]pyrrolo[2,3-b]pyridin-1(6H)-yl)
bicyclo[1.1.1]pentan-1-yl)-N'-methyl-N'-ethyl-1-
sulfonamide (25)

To a mixture consisting of compound 1j (70 mg, 0.29 mmol), $Et_3N$ (148 mg, 1.46 mmol), $K_2CO_3$ (404 mg, 2.93 mmol) and ACN (3 mL) was dropwise added a solution of ethyl(methyl)sulfamoyl chloride (46.0 mg, 0.29 mmol) in 0.5 mL ACN at 0° C. The mixture was stirred at 30° C. for 14 hrs. The mixture was diluted with $H_2O$ (20 mL) and extracted with DCM (40 mL*2). The combined organic layers were concentrated to dryness and the residue was purified by prep-HPLC (Method A) to afford the title product as a white solid (8.0 mg, 9% yield). LC-MS (Method 1): $t_R$=2.96 min, m/z (M+H)$^+$=361.1. $^1$H NMR (400 MHz, $CD_3OD$) δ 8.48 (s, 1H), 8.02 (s, 1H), 7.38 (d, J=3.6 Hz, 1H), 6.71 (d, J=3.6 Hz, 1H), 3.17 (q, J=7.2 Hz, 2H), 2.75 (s, 3H), 2.68 (s, 6H), 1.14 (t, J=7.2 Hz, 3H).

Example 26

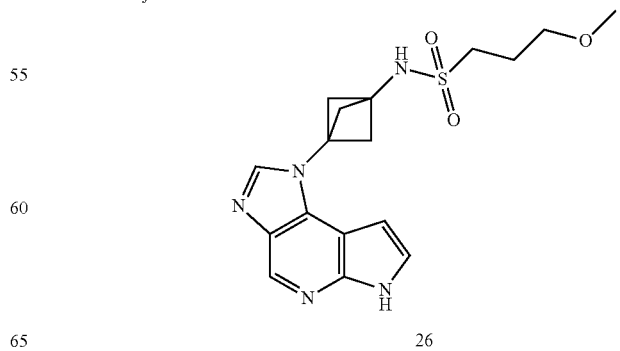

26

N-(3-(Imidazo[4,5-d]pyrrolo[2,3-b]pyridin-1(6H)-yl) bicyclo[1.1.1]pentan-1-yl)-3-methoxypropane-1-sulfonamide (26)

Example 26 (15 mg) was synthesized in 12% yield by utilizing similar preparative procedure of the final step of example 1 with compound 1j (80 mg, 0.33 mmol) and 3-methoxypropane-1-sulfonyl chloride (58 mg, 0.33 mmol) as starting materials. LC-MS (Method 1): $t_R$=3.11 min, m/z (M+H)$^+$=376.1. $^1$H NMR (400 MHz, DMSO-d$_6$) δ 11.92 (s, 1H), 8.59 (s, 1H), 8.11 (s, 1H), 7.50 (s, 1H), 6.69 (s, 1H), 3.45 (s, 4H), 3.09 (s, 3H), 2.68 (s, 6H), 1.93 (s, 2H).

Example 27

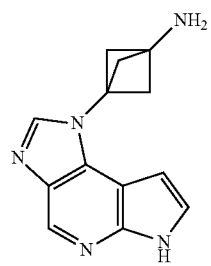
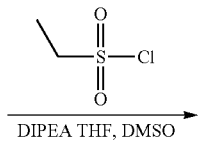

1j

N-(3-(imidazo[4,5-d]pyrrolo[2,3-b]pyridin-1(6H)-yl) bicyclo[1.1.1]pentan-1-yl)ethanesulfonamide (27)

Example 27 (11 mg) was synthesized in 16% yield by utilizing similar preparative procedure of the final step of example 1 with compound 1j (50 mg, 0.21 mmol) and ethanesulfonyl chloride (35 mg, 0.27 mmol) as starting materials. LC-MS (Method 1): $t_R$=3.36 min, m/z (M+H)$^+$=332.1. $^1$H NMR (400 MHz, CD$_3$OD) δ 8.87 (s, 1H), 8.68 (s, 1H), 7.73 (d, J=3.6 Hz, 1H), 7.10 (d, J=3.6 Hz, 1H), 3.16 (q, J=7.2 Hz, 2H), 2.90 (s, 6H), 1.41 (t, J=7.2 Hz, 3H).

Example 28

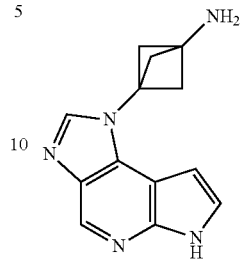
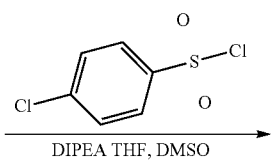

1j

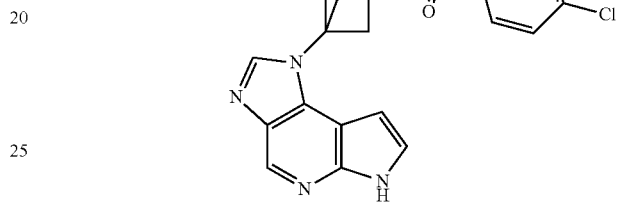

28

4-Chloro-N-(3-(imidazo[4,5-d]pyrrolo[2,3-b]pyridin-1(6H)-yl)bicyclo[1.1.1]pentan-1-yl)benzenesulfonamide (28)

Example 28 (12.4 mg) was synthesized in 14% yield by utilizing similar preparative procedure of the final step of example 1 with compound 1j (50 mg, 0.21 mmol) and 4-chlorobenzene-1-sulfonyl chloride (58 mg, 0.27 mmol) as starting materials. LC-MS (Method 1): $t_R$=2.94 min, m/z (M+H)$^+$=414.0. $^1$H NMR (400 MHz, CD$_3$OD) δ 8.45 (s, 1H), 7.94 (s, 1H), 7.85 (d, J=8.4 Hz, 2H), 7.54 (d, J=8.4 Hz, 2H), 7.36 (d, J=3.6 Hz, 1H), 6.57 (d, J=3.6 Hz, 1H), 2.52 (s, 6H).

Example 29

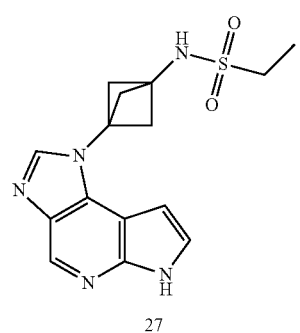

27

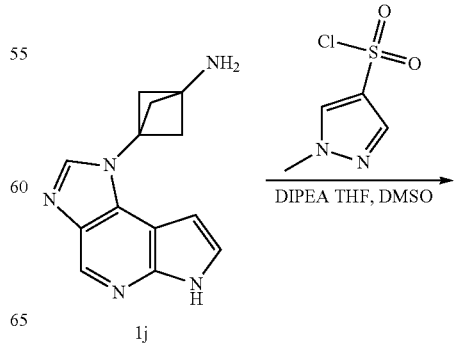

1j

-continued

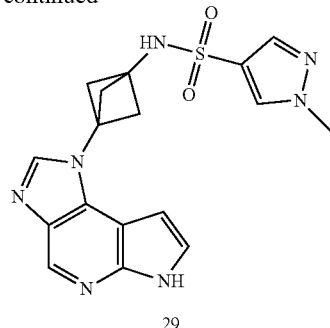

29

N-(3-(imidazo[4,5-d]pyrrolo[2,3-b]pyridin-1(6H)-yl)bicyclo[1.1.1]pentan-1-yl)-1-methyl-1H-pyrazole-4-sulfonamide (29)

Example 29 (5.5 mg) was synthesized in 7% yield by utilizing similar preparative procedure of the final step of example 1 with compound 1j (50 mg, 0.21 mmol) and 1-methyl-1H-pyrazole-4-sulfonyl chloride (49 mg, 0.27 mmol) as starting materials. LC-MS (Method 1): $t_R$=3.41 min, m/z (M+H)$^+$=384.1. $^1$H NMR (400 MHz, DMSO-d$_6$) δ 11.91 (s, 1H), 8.72 (s, 1H), 8.57 (s, 1H), 8.34 (s, 1H), 8.07 (s, 1H), 7.81 (s, 1H), 7.49 (t, J=3.2 Hz, 1H), 6.59-6.58 (m, 1H), 3.91 (s, 3H), 2.56 (s, 6H).

Example 30

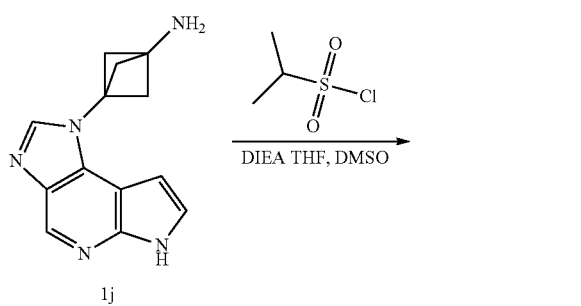

30

N-(3-(imidazo[4,5-d]pyrrolo[2,3-b]pyridin-1(6H)-yl)bicyclo[1.1.1]pentan-1-yl)propane-2-sulfonamide (30)

Example 30 (3.4 mg) was synthesized in 5% yield by utilizing similar preparative procedure of the final step of example 1 with compound 1j (50 mg, 0.21 mmol) and propane-2-sulfonyl chloride (39 mg, 0.27 mmol) as starting materials. LC-MS (Method 1): $t_R$=2.50 min, m/z (M+H)$^+$=346.1. $^1$H NMR (300 MHz, DMSO-d$_6$) δ 11.96 (s, 1H), 8.62 (s, 1H), 8.37 (s, 1H), 8.14 (s, 1H), 7.53 (t, J=2.7 Hz, 1H), 6.72 (d, J=1.2 Hz, 1H), 3.30-3.21 (m, 1H), 2.72 (s, 6H), 1.32 (d, J=6.9 Hz, 6H).

Example 31

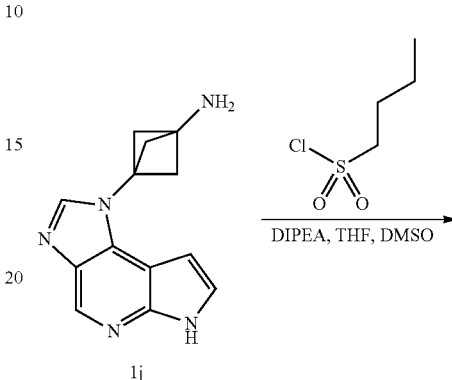

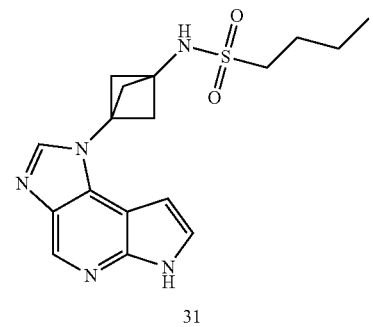

31

N-(3-(imidazo[4,5-d]pyrrolo[2,3-b]pyridin-1(6H)-yl)bicyclo[1.1.1]pentan-1-yl)butane-1-sulfonamide (31)

Example 31 (10 mg) was synthesized in 13% yield by utilizing similar preparative procedure of the final step of example 1 with compound 1j (50 mg, 0.21 mmol) and butane-1-sulfonyl chloride (66 mg, 0.42 mmol) as starting materials. LC-MS (Method 1): $t_R$=3.13 min, m/z (M+H)$^+$=360.1. $^1$H NMR (400 MHz, CD$_3$OD) δ 8.60 (s, 1H), 8.15 (s, 1H), 7.50 (d, J=3.6 Hz, 1H), 6.85 (d, J=3.2 Hz, 1H), 3.18-3.14 (m, 2H), 2.84 (s, 6H), 1.86-1.80 (m, 2H), 1.58-1.52 (m, 2H), 1.02 (t, J=7.2 Hz, 3H).

Example 32

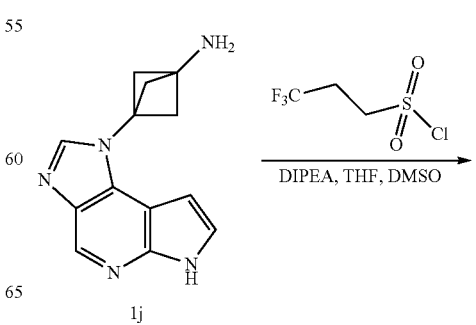

-continued

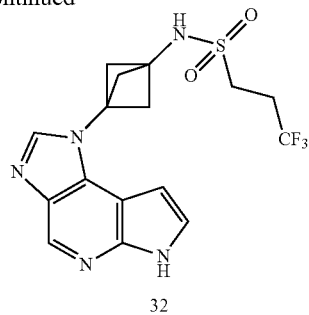

32

3,3,3-Trifluoro-N-(3-(imidazo[4,5-d]pyrrolo[2,3-b]pyridin-1(6H)-yl)bicyclo[1.1.1]pentan-1-yl)propane-1-sulfonamide (32)

Example 32 (4.7 mg) was synthesized in 6% yield by utilizing similar preparative procedure of the final step of example 1 with compound 1j (50 mg, 0.21 mmol) and 3,3,3-trifluoropropane-1-sulfonyl chloride (62 mg, 0.32 mmol) as starting materials. The final compound was purified by prep-HPLC (Method B) to afford the title compound. LC-MS (Method 1): $t_R$=3.17 min, m/z (M+H)$^+$=400.1. $^1$H NMR (400 MHz, CD$_3$OD) δ 8.67 (s, 1H), 8.41 (s, 1H), 7.55 (d, J=3.6 Hz, 1H), 6.92 (d, J=3.6 Hz, 1H), 3.31-3.27 (m, 2H), 2.79 (s, 6H), 2.67-2.61 (m, 2H). $^{19}$F NMR (376 MHz, CD$_3$OD) δ−67.55.

Example 33

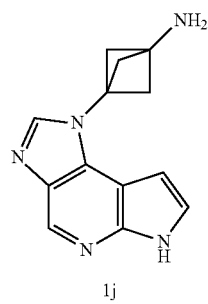

1j

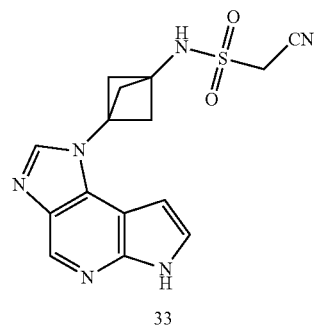

33

1-Cyano-N-(3-(imidazo[4,5-d]pyrrolo[2,3-b]pyridin-1(6H)-yl)bicyclo[1.1.1]pentan-1-yl)methanesulfonamide (33)

Example 33 (4.5 mg) was synthesized in 6% yield by utilizing similar preparative procedure of the final step of example 1 with compound 1j (50 mg, 0.21 mmol) and cyanomethanesulfonyl chloride (45 mg, 0.32 mmol) as starting materials. LC-MS (Method 1): $t_R$=3.32 min, m/z (M+H)$^+$=343.1. $^1$H NMR (400 MHz, DMSO-d$_6$) δ 11.94 (s, 1H), 8.59 (s, 1H), 8.12 (s, 1H), 7.50 (t, J=2.8 Hz, 1H), 6.75-6.74 (m, 1H), 4.87 (s, 2H), 2.75 (s, 6H).

Example 34

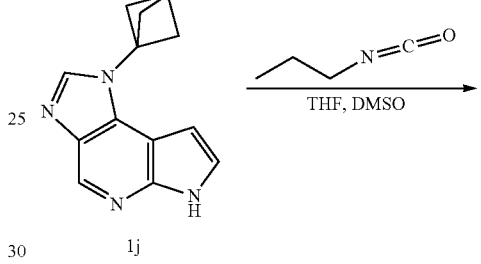

1j

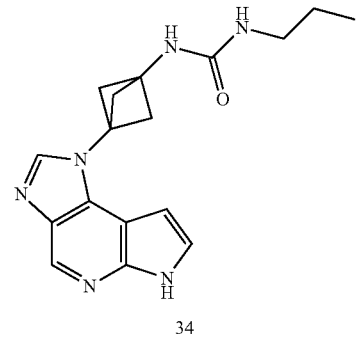

34

1-(3-(Imidazo[4,5-d]pyrrolo[2,3-b]pyridin-1(6H)-yl)bicyclo[1.1.1]pentan-1-yl)-3-propylurea (34)

To a well stirred solution consisting of compound 1j (50 mg, 0.21 mmol), THF (0.6 mL) and DMSO (0.2 mL) was added 1-isocyanatopropane (36 mg, 0.42 mmol). The mixture was stirred at 30° C. for 3 hrs. The mixture was concentrated to dryness to give a residue which was purified by prep-HPLC (Method A) to give the title product (27.3 mg, 40% yield) as a light yellow solid. LC-MS (Method 1): $t_R$=2.80 min, m/z (M+H)$^+$=325.2. $^1$H NMR (400 MHz, DMSO-d$_6$) δ 11.89 (s, 1H), 8.58 (s, 1H), 8.10 (s, 1H), 7.48 (t, J=2.8 Hz, 1H), 6.75-6.70 (m, 2H), 5.91 (t, J=5.6 Hz, 1H), 2.99-2.94 (m, 2H), 2.66 (s, 6H), 1.42-1.37 (m, 2H), 0.85 (t, J=7.2 Hz, 3H).

Example 35

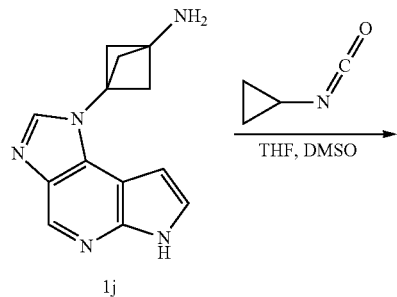

1j

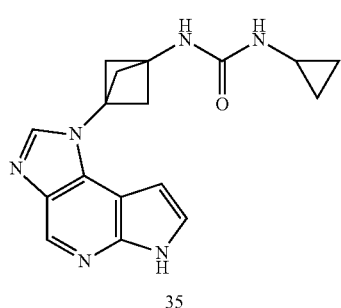

35

1-Cyclopropyl-3-(3-(imidazo[4,5-d]pyrrolo[2,3-b] pyridin-1(6H)-yl)bicyclo[1.1.1]pentan-1-yl)urea (35)

Example 35 (29.6 mg) was synthesized in 44% yield by utilizing similar preparative procedure of example 34 with compound 1j (50 mg, 0.21 mmol) and isocyanatocyclopropane (35 mg, 0.42 mmol) as starting materials. LC-MS (Method 1): $t_R$=2.83 min, m/z (M+H)$^+$=323.1. $^1$H NMR (400 MHz, DMSO-d$_6$) δ 11.89 (s, 1H), 8.58 (s, 1H), 8.10 (s, 1H), 7.49 (t, J=3.2 Hz, 1H), 6.77 (s, 1H), 6.71 (dd, J=2.0 Hz, 3.6 Hz, 1H), 6.21 (d, J=2.4 Hz, 1H), 2.67 (s, 6H), 2.45-2.41 (m, 1H), 0.60-0.56 (m, 2H), 0.38-0.34 (m, 2H).

Example 36

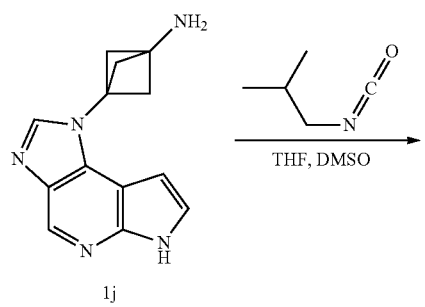

1j

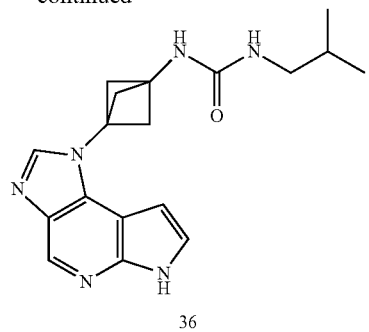

36

1-(3-(Imidazo[4,5-d]pyrrolo[2,3-b]pyridin-1(6H)-yl)bicyclo[1.1.1]pentan-1-yl)-3-isobutylurea (36)

Example 36 (17.4 mg) was synthesized in 25% yield by utilizing similar preparative procedure example 34 with compound 1j (50 mg, 0.21 mmol) and 1-isocyanato-2-methylpropane (41 mg, 0.42 mmol) as starting materials. LC-MS (Method 1): $t_R$=3.23 min, m/z (M+H)$^+$=339.2. $^1$H NMR (400 MHz, DMSO-d$_6$) δ 11.89 (s, 1H), 8.58 (s, 1H), 8.10 (s, 1H), 7.48 (t, J=3.2 Hz, 1H), 6.73 (s, 1H), 6.72 (dd, J=1.6, 3.2 Hz, 1H), 5.95 (t, J=5.6 Hz, 1H), 2.84 (t, J=6.4 Hz, 2H), 2.66 (s, 6H), 1.67-1.61 (m, 1H), 0.84 (d, J=6.8 Hz, 6H).

Example 37

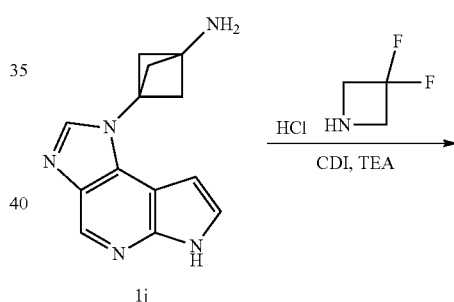

1j

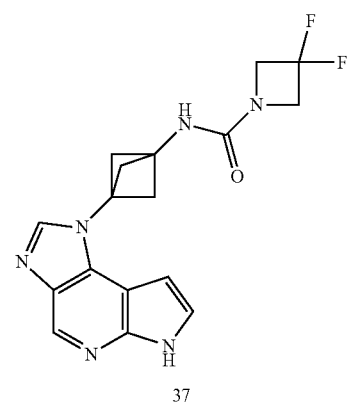

37

3,3-Difluoro-N-(3-(imidazo[4,5-d]pyrrolo[2,3-b]pyridin-1(6H)-yl)bicyclo[1.1.1]pentan-1-yl)azetidine-1-carboxamide (37)

To a well stirred solution consisting of compound 1j (50 mg, 0.21 mmol), TEA (74 mg, 0.73 mmol), DCM (1.0 mL)

and DMSO (0.5 mL) was added CDI (68 mg, 0.42 mmol) in one portion. The mixture was stirred at RT for 2 hrs. The resulting reaction solution was added to a solution of 3,3-difluoroazetidine hydrochloride (95 mg, 0.73 mmol) and TEA (84 mg, 0.84 mmol) in DCM (1 mL). The mixture was stirred at RT overnight. The mixture was concentrated and the residue was purified by prep-HPLC (Method A) to afford the title product as a white solid (11.1 mg, 15% yield). LC-MS (Method 1): $t_R$=2.79 min, m/z (M+H)$^+$=359.2. $^1$H NMR (400 MHz, DMSO-d$_6$) δ 11.91 (s, 1H), 8.59 (s, 1H), 8.12 (s, 1H), 7.75 (s, 1H), 7.49 (s, 1H), 6.67 (s, 1H), 4.25 (t, J=12.8 Hz, 4H), 2.69 (s, 6H). $^{19}$F NMR (376 MHz, DMSO-d$_6$) δ-99.31.

Example 38

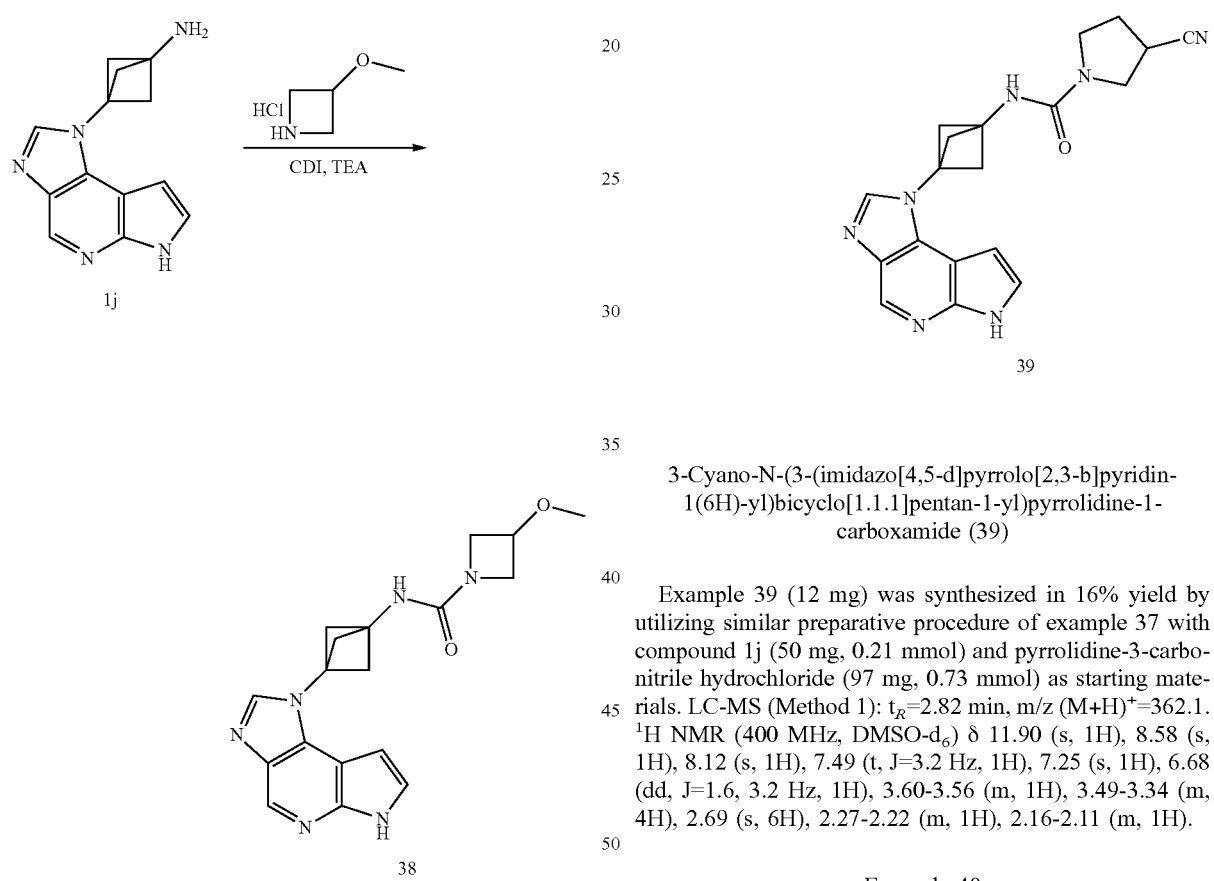

N-(3-(Imidazo[4,5-d]pyrrolo[2,3-b]pyridin-1(6H)-yl)bicyclo[1.1.1]pentan-1-yl)-3-methoxyazetidine-1-carboxamide (38)

Example 38 (26.6 mg) was synthesized in 36% yield by utilizing similar preparative procedure of example 37 with compound 1j (50 mg, 0.21 mmol) and 3-methoxyazetidine hydrochloride (90 mg, 0.73 mmol) as starting materials. LC-MS (Method 1): $t_R$=2.77 min, m/z (M+H)$^+$=353.2. $^1$H NMR (400 MHz, DMSO-d$_6$) δ 11.91 (s, 1H), 8.58 (s, 1H), 8.11 (s, 1H), 7.49 (s, 1H), 7.31 (s, 1H), 6.67 (d, J=2.0 Hz, 1H), 4.14 (br s, 1H), 4.01-3.98 (m, 2H), 3.65-3.61 (m, 2H), 3.20 (s, 3H), 2.66 (s, 6H).

Example 39

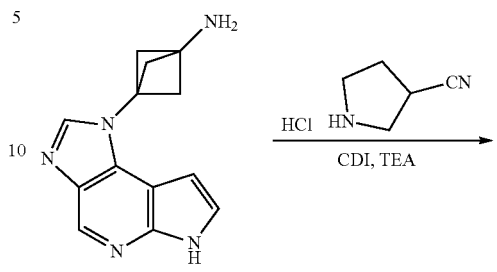

3-Cyano-N-(3-(imidazo[4,5-d]pyrrolo[2,3-b]pyridin-1(6H)-yl)bicyclo[1.1.1]pentan-1-yl)pyrrolidine-1-carboxamide (39)

Example 39 (12 mg) was synthesized in 16% yield by utilizing similar preparative procedure of example 37 with compound 1j (50 mg, 0.21 mmol) and pyrrolidine-3-carbonitrile hydrochloride (97 mg, 0.73 mmol) as starting materials. LC-MS (Method 1): $t_R$=2.82 min, m/z (M+H)$^+$=362.1. $^1$H NMR (400 MHz, DMSO-d$_6$) δ 11.90 (s, 1H), 8.58 (s, 1H), 8.12 (s, 1H), 7.49 (t, J=3.2 Hz, 1H), 7.25 (s, 1H), 6.68 (dd, J=1.6, 3.2 Hz, 1H), 3.60-3.56 (m, 1H), 3.49-3.34 (m, 4H), 2.69 (s, 6H), 2.27-2.22 (m, 1H), 2.16-2.11 (m, 1H).

Example 40

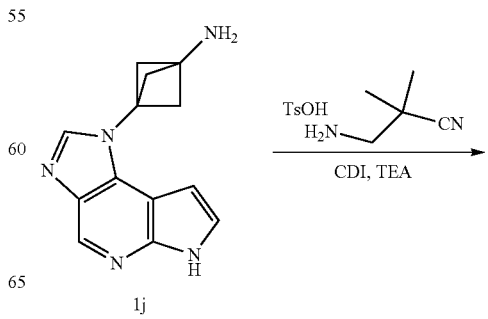

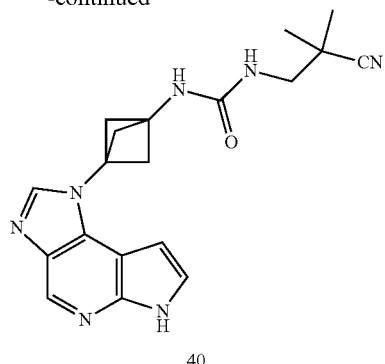

40

1-(2-Cyano-2-methylpropyl)-3-(3-(imidazo[4,5-d]pyrrolo[2,3-b]pyridin-1(6H)-yl)bicyclo[1.1.1]pentan-1-yl)urea (40)

Example 40 (21.4 mg) was synthesized in 28% yield by utilizing similar preparative procedure of example 37 with compound 1j (50 mg, 0.21 mmol) and 3-amino-2,2-dimethylpropanenitrile 4-methylbenzenesulfonate (198 mg, 0.73 mmol) as starting materials. LC-MS (Method 1): $t_R$=3.26 min, m/z (M+H)$^+$=364.2. $^1$H NMR (400 MHz, DMSO-d$_6$) δ 11.90 (s, 1H), 8.58 (s, 1H), 8.11 (s, 1H), 7.49 (s, 1H), 6.96 (s, 1H), 6.72 (s, 1H), 6.38-6.35 (m, 1H), 3.22 (d, J=6.4 Hz, 2H), 2.68 (s, 6H), 1.26 (s, 6H).

Example 41

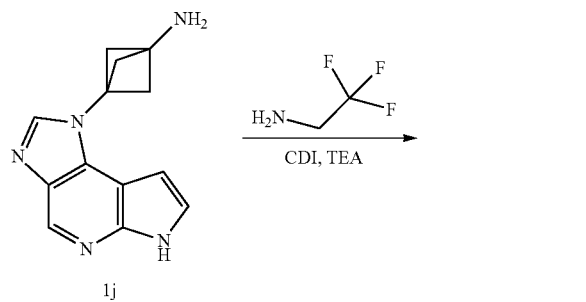

41

1-(3-(Imidazo[4,5-d]pyrrolo[2,3-b]pyridin-1(6H)-yl)bicyclo[1.1.1]pentan-1-yl)-3-(2,2,2-trifluoroethyl)urea (41)

Example 41 (19.6 mg) was synthesized in 21% yield by utilizing similar preparative procedure of example 37 with compound 1j (60 mg, 0.25 mmol) and 2,2,2-trifluoroethanamine (87 mg, 0.88 mmol) as starting materials. LC-MS (Method 1): $t_R$=3.09 min, m/z (M+H)$^+$=365.1. $^1$H NMR (400 MHz, DMSO-d$_6$) δ 11.90 (s, 1H), 8.58 (s, 1H), 8.10 (s, 1H), 7.49 (t, J=2.8 Hz, 1H), 7.17 (s, 1H), 6.71 (dd, J=1.6, 3.2 Hz, 1H), 6.58 (t, J=6.4 Hz, 1H), 3.88-3.79 (m, 2H), 2.68 (t, J=8.0 Hz, 6H). $^{19}$F NMR (376 MHz, DMSO-d$_6$) δ−71.54.

Example 42

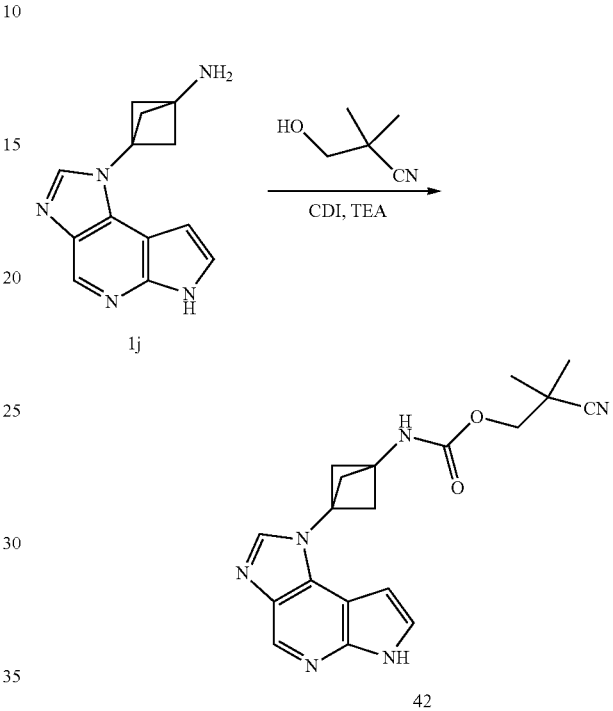

42

2-Cyano-2-methylpropyl (3-(imidazo[4,5-d]pyrrolo[2,3-b]pyridin-1(6H)-yl)bicyclo[1.1.1]pentan-1-yl)carbamate (42)

Example 42 (2.2 mg) was synthesized in 3% yield by utilizing similar preparative procedure of example 19 with compound 1j (50 mg, 0.21 mmol) and 3-hydroxy-2,2-dimethylpropanenitrile (50 mg, 0.73 mmol) as starting materials. LC-MS (Method 1): $t_R$=3.23 min, m/z (M+H)$^+$=365.2. $^1$H NMR (400 MHz, DMSO-d$_6$) δ 11.91 (s, 1H), 8.59 (s, 1H), 8.47 (s, 1H), 8.12 (s, 1H), 7.49 (s, 1H), 6.69 (s, 1H), 4.04 (s, 2H), 2.71 (s, 6H), 1.35 (s, 6H).

Example 43

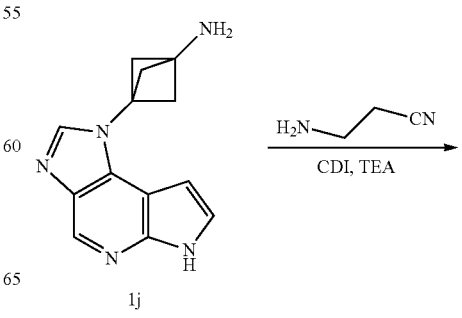

1j

95

-continued

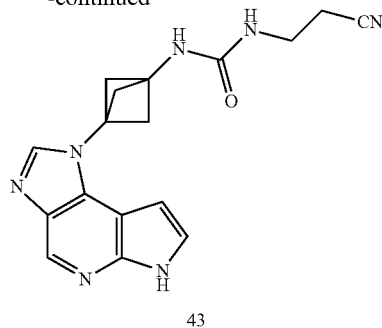

43

1-(2-Cyanoethyl)-3-(3-(imidazo[4,5-d]pyrrolo[2,3-b]pyridin-1(6H)-yl)bicyclo[1.1.1]pentan-1-yl)urea (43)

Example 43 (12.8 mg) was synthesized in 18% yield by utilizing similar preparative procedure example 37 with compound 1j (50 mg, 0.21 mmol) and 3-aminopropanenitrile (51 mg, 0.73 mmol) as starting materials. LC-MS (Method 1): $t_R$=2.60 min, m/z (M+H)$^+$=336.2. H NMR (400 MHz, CD$_3$OD) δ 8.60 (s, 1H), 8.13 (s, 1H), 7.49 (d, J=3.6 Hz, 1H), 6.91 (d, J=3.6 Hz, 1H), 3.43 (t, J=6.4 Hz, 2H), 2.84 (s, 6H), 2.68 (t, J=6.8 Hz, 2H).

Example 44

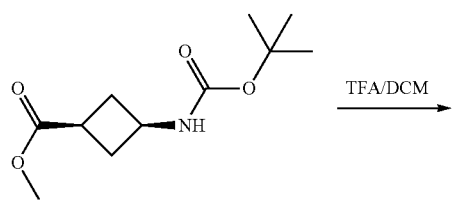

44a

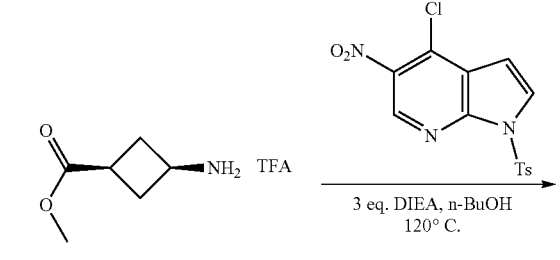

44b

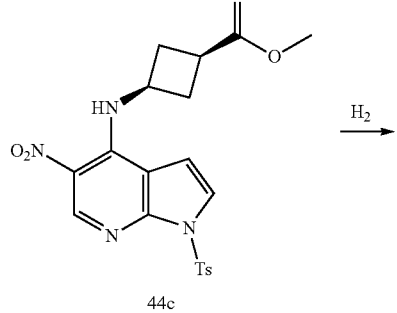

44c

96

-continued

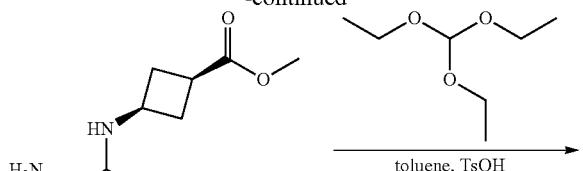

44d

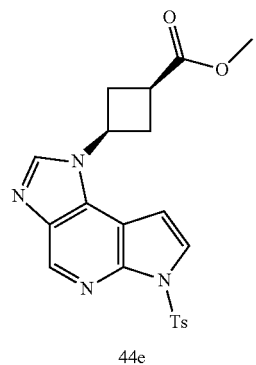

44e

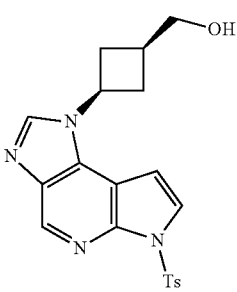

44f

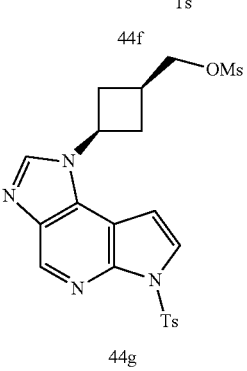

44g

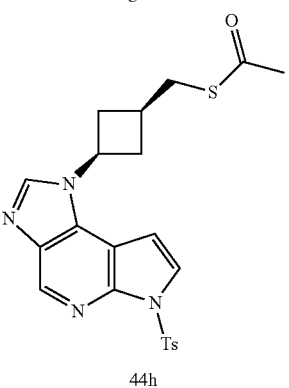

44h

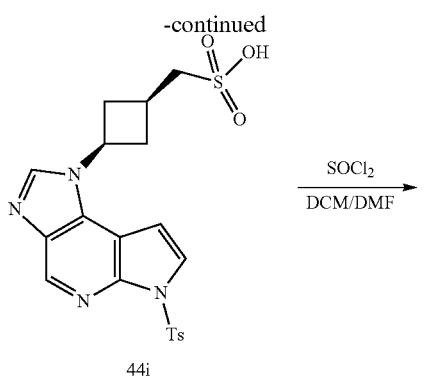

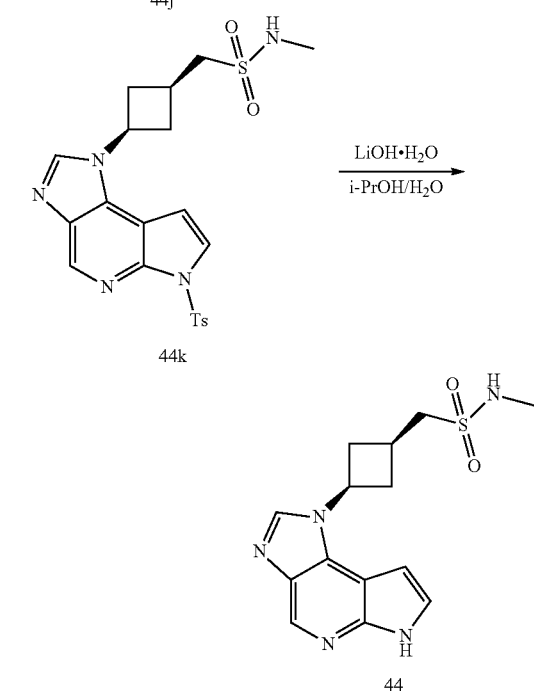

Step 1. Methyl cis-3-aminocyclobutane-1-carboxylate TFA (44b)

To a solution of compound 44a (500 mg, 2.18 mmol) in 5 μmL of DCM was added TFA (2.5 mL) at 0° C. The solution was stirred at 0° C. to 5° C. for 1.5 hrs. The solution was concentrated to afford the title product as colorless oil (530 mg, 100% yield). $^1$H NMR (400 MHz, DMSO-$d_6$) δ 8.05 (br s, 2H), 3.62-3.59 (m, 4H), 3.02-2.93 (m, 1H), 2.46-2.39 (m, 2H), 2.29-2.21 (m, 2H).

Step 2. Methyl cis-3-((5-nitro-1-tosyl-1H-pyrrolo[2,3-b]pyridin-4-yl)amino) cyclobutanecarboxylate (44c)

Compound 44c (760 mg) was synthesized in 78% yield by utilizing similar preparative procedure of the third step of example 1 with 4-chloro-5-nitro-1-tosyl-1H-pyrrolo[2,3-b]pyridine (765 mg, 2.18 mmol) and compound 44b (530 mg, 2.18 mmol) as starting materials. $^1$H NMR (400 MHz, DMSO-$d_6$) δ 8.90-8.87 (m, 2H), 8.00 (d, J=8.4 Hz, 2H), 7.79 (d, J=4.4 Hz, 1H), 7.44 (d, J=8.4 Hz, 2H), 7.13 (d, J=4.0 Hz, 1H), 4.59-4.53 (m, 1H), 3.61 (s, 3H), 3.04-2.97 (m, 1H), 2.75-2.68 (m, 2H), 2.36 (s, 3H), 2.33-2.26 (m, 2H).

Step 3. Methyl cis-3-((5-amino-1-tosyl-1H-pyrrolo[2,3-b]pyridin-4-yl)amino) cyclobutanecarboxylate (44d)

Compound 44d (640 mg) was synthesized in 92% yield by utilizing similar preparative procedure of the fourth step of example 1 with compound 44c (750 mg, 1.69 mmol) as starting materials. LC-MS (Method 3): $t_R$=1.55 min, m/z (M+H)$^+$=415.1.

Step 4. Methyl cis-3-(6-tosylimidazo[4,5-d]pyrrolo[2,3-b]pyridin-1(6H)-yl) cyclobutanecarboxylate (44e)

Compound 44e (550 mg) was synthesized in 84% yield by utilizing similar preparative procedure of the fifth step of example 1 with compound 44d (640 mg, 1.54 mmol) and triethoxymethane (571 mg, 3.86 mmol) as starting materials. $^1$H NMR (400 MHz, DMSO-$d_6$) δ 8.73 (s, 1H), 8.58 (s, 1H), 8.01 (d, J=8.4 Hz, 2H), 7.97 (d, J=4.4 Hz, 1H), 7.40 (d, J=8.0 Hz, 2H), 7.29 (d, J=3.6 Hz, 1H), 5.22-5.17 (m, 1H), 3.34 (s, 3H), 3.19-3.12 (m, 1H), 2.89-2.82 (m, 2H), 2.74-2.66 (m, 2H), 2.32 (m, 3H).

Step 5. (Cis-3-(6-tosylimidazo[4,5-d]pyrrolo[2,3-b]pyridin-1(6H)-yl)cyclobutyl)methanol (44f)

To a solution of compound 44e (550 mg, 1.30 mmol) in 5 μmL dry THF was added LiAlH$_4$ (73.9 mg, 1.94 mmol) at 0° C. The mixture was stirred for 1.5 hrs at RT. After cooling down to 0° C., the reaction mixture was quenched with 0.1 mL of water, 0.2 mL of 10% aq. NaOH, followed by 0.3 mL of water. The mixture was dried over Na$_2$SO$_4$ and filtered. The filtrate was concentrated to afford the crude title product as a white solid (450 mg, 88% yield). LC-MS (Method 3): $t_R$=1.43 min, m/z (M+H)$^+$=397.1.

Step 6. (Cis-3-(6-tosylimidazo[4,5-d]pyrrolo[2,3-b]pyridin-1(6H)-yl)cyclobutyl)methyl methanesulfonate (44g)

Compound 44f (450 mg, 1.13 mmol) and Et$_3$N (344 mg, 3.40 mmol) were dissolved in DCM (15 mL) followed by the addition of MsCl (196 mg, 1.70 mmol) at 0° C. After stirring for 1 hour at RT, the reaction mixture was diluted with water (100 mL) and extracted with EtOAc (150 mL). The organic layer was separated, washed with brine (40 mL), dried over Na$_2$SO$_4$ and filtered. The filtrate was concentrated to dryness to afford the crude title compound (539 mg, 100% yield) as a yellow solid. LC-MS (Method 3): $t_R$=1.35 min, m/z (M+H)$^+$=475.1.

Step 7. S-((cis-3-(6-tosylimidazo[4,5-d]pyrrolo[2,3-b]pyridin-1(6H)-yl)cyclobutyl)methyl) ethanethioate (44h)

Compound 44g (535 mg, 1.13 mmol) and potassium thioacetate (386 mg, 3.38 mmol) were mixed in DMF (16 mL) and then heated at 50° C. for 5 hrs. The reaction mixture was diluted with water (100 mL) and extracted with EtOAc (150 mL). The separated organic layer was concentrated. The residue was purified by reverse chromatography (ACN in water from 5-95%) to afford the crude title compound (338 mg, 66% yield) as a yellow solid. LC-MS (Method 3): $t_R$=1.53 min, m/z (M+H)$^+$=455.1.

Step 8. (Cis-3-(6-tosylimidazo[4,5-d]pyrrolo[2,3-b]pyridin-1(6H)-yl)cyclobutyl) methanesulfonic acid (44i)

An aqueous hydrogen peroxide (0.55 mL, 30%) was added dropwise to a stirred suspension of compound 44h (330 mg, 0.73 mmol) in formic acid (4 mL). The resulting mixture was stirred at room temperature for 1 hour. Then the reaction mixture was concentrated to afford the title compound (334 mg, 100% yield) as a white solid. LC-MS (Method 3): $t_R$=0.81 min, m/z (M+H)$^+$=461.1.

Step 9. (Cis-3-(6-tosylimidazo[4,5-d]pyrrolo[2,3-b]pyridin-1(6H)-yl)cyclobutyl) methanesulfonyl chloride (44j)

To a mixture of compound 44i (330 mg, 0.73 mmol) in DCM (50 mL) and DMF (1.0 mL) was added thionyl chloride (930 mg, 7.82 mmol). Then the reaction mixture was heated at 50° C. for 3 hours. The mixture was concentrated to afford title compound (334 mg, 100%) as a yellow solid. A small amount of the reaction solution was mixed with MeOH for analysis. LC-MS (Method 3): $t_R$=1.60 min, m/z (M+H)$^+$=475.1.

Step 10. N-methyl-1-(cis-3-(6-tosylimidazo[4,5-d]pyrrolo[2,3-b]pyridin-1(6H)-yl)cyclobutyl)methanesulfonamide (44k)

To a solution consisting of CH$_3$NH$_2$·HCl (34 mg, 0.50 mmol), TEA (127 mg, 1.25 mmol) and DCM (2 mL) was added compound 44j (200 mg, 0.42 mmol) at 0° C. The mixture was stirred at RT for 1.5 hrs. The mixture was diluted with water (30 mL) and extracted with DCM (40 mL). The separated organic layer was washed with water (30 mL*2) and concentrated to afford the crude title product as a white solid (25 mg, 13% yield). LC-MS (Method 3): $t_R$=1.43 min, m/z (M+H)$^+$=474.1.

Step 11. 1-(Cis-3-(imidazo[4,5-d]pyrrolo[2,3-b]pyridin-1(6H)-yl)cyclobutyl)-N-methylmethanesulfonamide (44)

Compound 44k (22 mg, 0.05 mmol) and LiOH H$_2$O (10 mg, 0.05 mmol) were dissolved in a mixture of i-PrOH and H$_2$O (2.5 ml, V:V=4:1). The above solution was stirred at 60° C. for 24 hrs. The reaction mixture was diluted with water (10 mL) and extracted with EtOAc (20 mL). The separated organic layer was concentrated and the residue was purified by prep-HPLC (Method A) to afford the title compound (3.7 mg, 25% yield) as a white solid. LC-MS (Method 1): $t_R$=2.37 min, m/z (M+H)$^+$=320.1. $^1$H NMR (400 MHz, DMSO-d$_6$) δ 8.59 (s, 1H), 8.42 (s, 1H), 7.46 (d, J=3.6 Hz, 1H), 6.88 (d, J=3.6 Hz, 1H), 5.26-4.86 (m, 1H), 3.38-3.33 (m, 2H), 3.09-3.02 (m, 2H), 2.86-2.80 (m, 1H), 2.76 (s, 3H), 2.54-2.47 (m, 2H).

Example 45

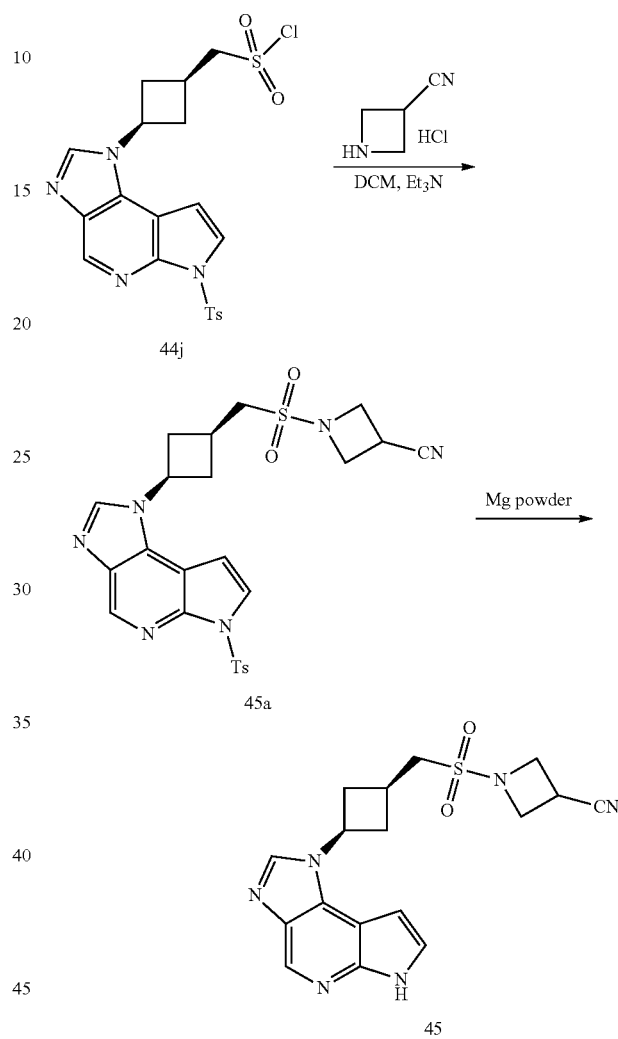

Step 1. 1-(((Cis-3-(6-tosylimidazo[4,5-d]pyrrolo[2,3-b]pyridin-1(6H)-yl)cyclobutyl)methyl) sulfonyl) azetidine-3-carbonitrile (45a)

Compound 45a (80 mg) was synthesized in 64% yield by utilizing similar preparative procedure of the tenth step of example 44 with compound 44j (120 mg, 0.25 mmol) and azetidine-3-carbonitrile hydrochloride (32 mg, 0.26 mmol) as starting materials. LC-MS (Method 3): $t_R$=1.50 min, m/z (M+H)$^+$=525.1.

Step 2. 1-(((Cis-3-(imidazo[4,5-d]pyrrolo[2,3-b]pyridin-1(6H)-yl)cyclobutyl)methyl) sulfonyl) azetidine-3-carbonitrile (45)

A mixture of compound 45a (40 mg, 0.08 mmol) and Mg powder (73 mg, 3.05 mmol) in MeOH (2 mL) was placed in an ultrasonic bath for 1.5 hours. The mixture was filtered and the filtrate was concentrated. The residue was purified by prep-HPLC (Method A) to afford the title product as an off-white solid (1.4 mg, 5% yield). LC-MS (Method 1): $t_R$=3.04 min, m/z (M+H)$^+$=371.1. $^1$H NMR (400 MHz, CD$_3$OD) δ 8.59 (s, 1H), 8.42 (s, 1H), 7.46 (d, J=3.6 Hz, 1H), 6.90 (d, J=3.6 Hz, 1H), 5.28-4.86 (m, 1H), 4.29-4.24 (m, 2H), 4.16-4.13 (m, 2H), 3.75-3.69 (m, 1H), 3.50-3.43 (m, 2H), 3.07-3.01 (m, 2H), 2.89-2.85 (m, 1H), 2.56-2.48 (m, 2H).

Example 46

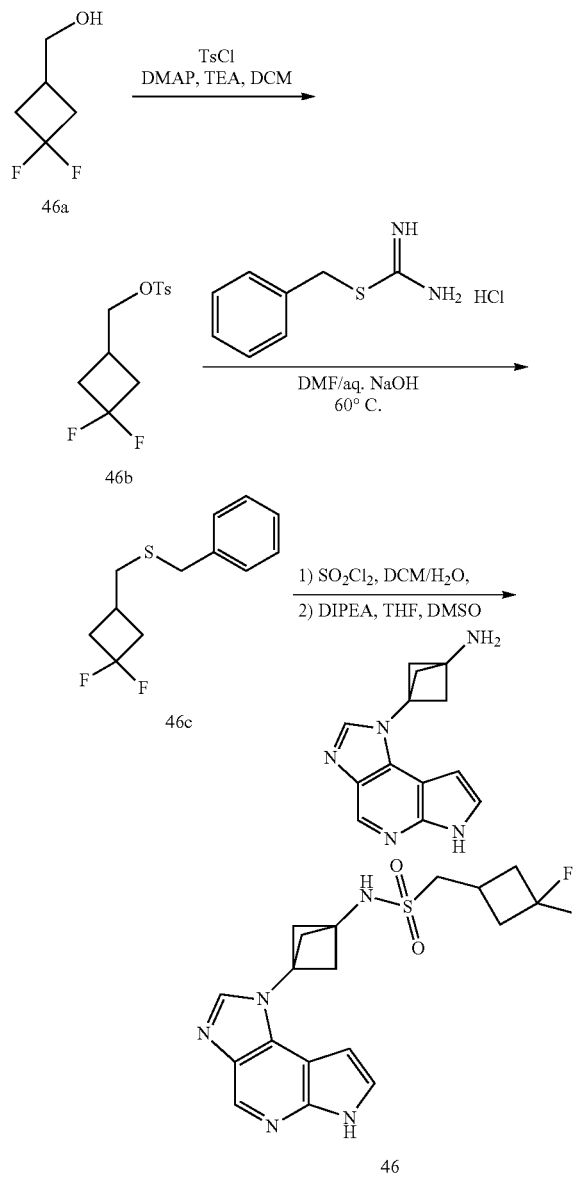

Step 1. (3,3-Difluorocyclobutyl)methyl 4-methylbenzenesulfonate (46b)

To a mixture of (3,3-difluorocyclobutyl)methanol (1 g, 8.19 mmol), DMAP (100 mg, 0.82 mmol) and TEA (1.24 g, 12.29 mmol) in DCM (10 mL) was added TsCl (889 mg, 9.83 mmol) at 0° C. and allowed to warm to RT. After stirring overnight at RT, the mixture was diluted with 20 mL of DCM and washed with water (10 mL), brine (10 mL) and dried over Na$_2$SO$_4$. The mixture was filtered and filtrate was concentrated to afford crude title compound (1.89 g crude, 79% yield) as yellow oil.

Step 2. Benzyl ((3,3-difluorocyclobutyl)methyl)sulfane (46c)

To a mixture of compound 46b (100 mg, 0.36 mmol) and benzyl carbamimidothioate hydrochloride (88 mg, 0.43 mmol) in DMF (0.5 mL) was added NaOH (36 mg, 0.90 mmol) in H$_2$O (0.5 mL). The mixture was stirred at 60° C. overnight. The mixture was diluted with H$_2$O (10 mL) and extracted with EtOAc (30 mL*3). The combined organic layers were dried Na$_2$SO$_4$, filtered and concentrated. The residue was purified by column chromatography on silica gel (PE:EA=80:1) to give the crude title product as yellow oil (82 mg, 99% yield). $^1$H NMR (400 MHz, CDCl$_3$) δ 7.34-7.28 (m, 5H), 3.70 (s, 2H), 2.71-2.60 (m, 2H), 2.55 (d, J=7.2 Hz, 2H), 2.32-2.14 (m, 3H).

Step 3. 1-(3,3-Difluorocyclobutyl)-N-(3-(imidazo[4,5-d]pyrrolo[2,3-b]pyridin-1(6H)-yl)bicyclo[1.1.1]pentan-1-yl)methanesulfonamide (46)

To a mixture consisting of compound 46c (82 mg, 0.36 mmol), DCM (1.5 mL) and H$_2$O (0.4 mL) was added SO$_2$Cl$_2$ (418 mg, 3.09 mmol) at −5° C. The mixture was stirred at 0° C. for 30 minutes. Then ice-water (15 mL) was added and the mixture was extracted with DCM (20 mL*2). The combined organic layers were dried over Na$_2$SO$_4$, filtered and concentrated. The residue was dissolved into THF (0.5 mL) and the solution was added to a mixture of 1j (100 mg, 0.44 mmol) and DIPEA (170 mg, 1.31 mmol) in THF (1.5 mL) and DMSO (1 mL) at 0° C. The mixture was stirred at room temperature for 2 hours. The mixture was diluted with H$_2$O (15 mL) and extracted with EtOAc (20 mL*2). The combined organic layers were concentrated. The residue was purified by prep-TLC (DCM:MeOH=25:1) and prep-HPLC (Method A) to afford the title product as a yellow solid (14 mg, 8% yield). LC-MS (Method 1): $t_R$=2.98 min, m/z (M+H)$^+$=408.1. $^1$H NMR (400 MHz, DMSO-d$_6$) δ 11.93 (s, 1H), 8.60 (s, 1H), 8.50 (s, 1H), 8.12 (s, 1H), 7.51 (t, J=2.8 Hz, 1H), 6.71 (t, J=1.6 Hz, 1H), 3.39-3.38 (m, 2H), 2.82-2.75 (m, 2H), 2.72 (s, 6H), 2.62-2.53 (m, 3H).

Example 47

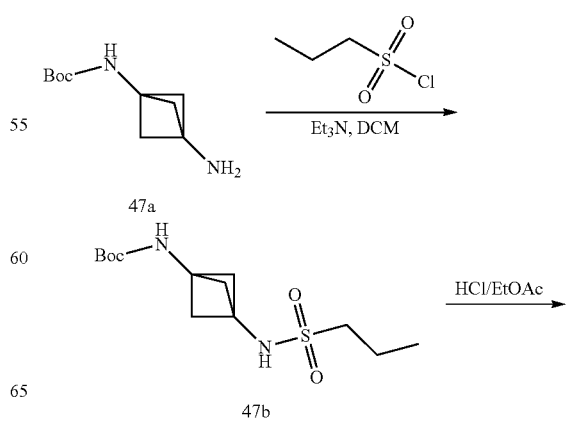

103

-continued

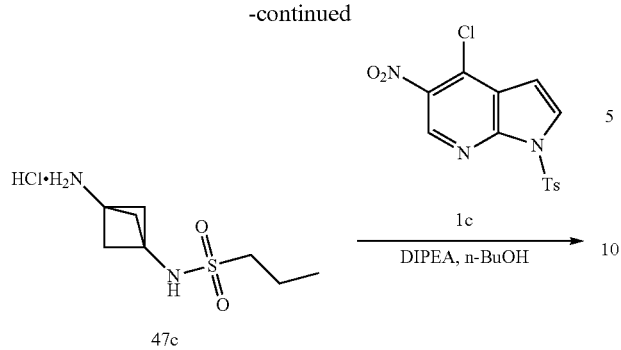

47c

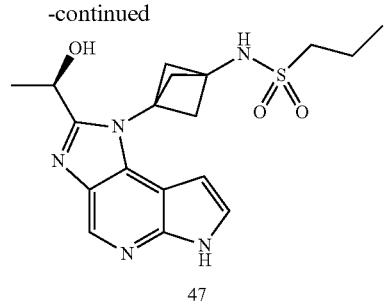

1c

DIPEA, n-BuOH

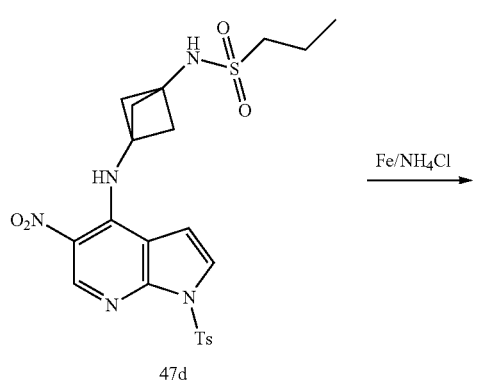

47d

Fe/NH₄Cl

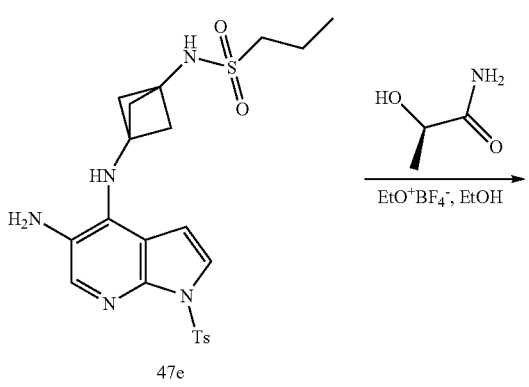

47e

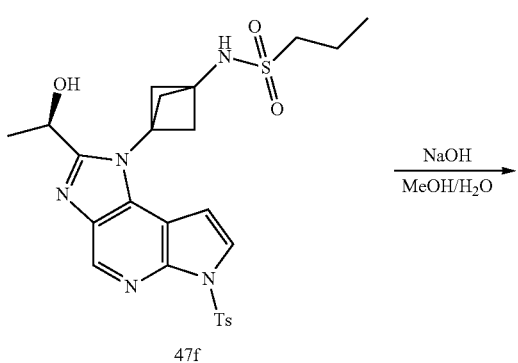

47f

104

-continued

47

NaOH
MeOH/H₂O

Step 1. Tert-butyl (3-(propylsulfonamido)bicyclo
[1.1.1]pentan-1-yl)carbamate (47b)

To a solution of compound 47a (1.0 g, 5.04 mmol) and Et₃N (1.5 g, 15.1 mmol) in DCM (1.5 mL) was added propane-1-sulfonyl chloride (1.0 g, 7.56 mmol) at 0° C. After stirring at RT for 3 hrs, the mixture was diluted with water (100 mL) and extracted with DCM (100 mL*2). The combined organic phases were washed with brine (100 mL*2), dried over Na₂SO₄, and filtered. The filtrate was concentrated to afford the title compound (1.45 g, 97% yield) as a white solid. ¹H NMR (400 MHz, DMSO-d₆) δ 8.00 (s, 1H), 7.55 (s, 1H), 2.94-2.90 (m, 2H), 2.05 (s, 6H), 1.69-1.59 (m, 2H), 1.37 (s, 9H) 1.03-0.91 (m, 3H).

Step 2. N-(3-aminobicyclo[1.1.1]pentan-1-yl)pro-
pane-1-sulfonamide (47c)

To a solution of compound 47b (1.45 g, 4.77 mmol) in EtOAc (20 mL) was added HCl(g) in EtOAc (2 M, 20 mL) at 0° C. The reaction mixture was stirred at RT for 3 hrs. The mixture was concentrated in vacuo to give the title compound (1.2 g, crude, yield~100%) as a white solid. ¹H NMR (400 MHz, DMSO-d₆) δ 9.02 (s, 3H), 8.25 (s, 1H), 2.98-2.95 (m, 2H), 2.13 (s, 6H), 1.73-1.61 (m, 2H), 1.03-0.96 (m, 3H).

Step 3. N-(3-((5-nitro-1-tosyl-1H-pyrrolo[2,3-b]
pyridin-4-yl)amino)bicyclo[1.1.1]pentan-1-yl)pro-
pane-1-sulfonamide (47d)

Compound 47d (2.4 g) was synthesized in 100% yield by utilizing similar preparative procedure of the third step of example 1 with compound 47c (1.2 g, 4.99 mmol) and compound 1c (1.6 g, 4.54 mmol) as starting materials. LC-MS (Method 3): $t_R$=1.68 min, m/z (M+H)⁺=520.1

Step 4. N-(3-((5-amino-1-tosyl-1H-pyrrolo[2,3-b]
pyridin-4-yl)amino)bicyclo[1.1.1]pentan-1-yl)pro-
pane-1-sulfonamide (47e)

To a solution consisting of 47d (2.4 g, 4.62 mmol), NH₄Cl (1.2 g, 23.1 mmole), MeOH (900 mL) and H₂O (300 mL) were added Fe powder (905 mg, 16.2 mmol) at RT. The reaction mixture was stirred at 80° C. for 2 hrs. After cooling to RT, the mixture was filtered and the filter cake was washed with MeOH (20 mL). The filtrate was concentrated in vacuo to afford the title compound (2.2 g, 95.6%, crude) as a brown solid. LC-MS (Method 3): $t_R$=1.44 min, m/z (M+H)⁺=490.1.

Step 5. (R)—N-(3-(2-(1-hydroxyethyl)-6-tosylimi-
dazo[4,5-d]pyrrolo[2,3-b]pyridin-1(6H)-yl)bicyclo
[1.1.1]pentan-1-yl)propane-1-sulfonamide (47f)

(R)-2-hydroxypropanamide (136 mg, 1.53 mmol) and triethyloxonium tetrafluoroborate (291 mg, 1.53 mmol)

were dissolved in THF (5 μmL) and the resulting mixture was stirred at RT for 30 mins under N₂. Then 47e (150 mg, 0.31 mmol) in EtOH (5 μmL) was added to the reaction mixture. The mixture was stirred for 2 hrs at 85° C. After cooling to RT, the mixture was diluted with water (100 mL) and extracted with EtOAc (100 mL*2). The combined organic layers were concentrated and the residue was purified by prep-TLC (DCM:MeOH=10:1) to afford the desired compound (55 mg, yield 50%) as a brown solid. $^1$H NMR (400 MHz, DMSO-d₆) δ 8.72 (s, 1H), 8.36 (s, 1H), 8.00 (s, 1H), 8.99 (d, J=8.0 Hz, 2H), 7.40 (d, J=8.0 Hz, 2H), 7.07 (d, J=4.0 Hz, 1H), 5.53 (d, J=7.2 Hz, 1H), 5.07-5.04 (m, 1H), 3.09-3.05 (m, 2H), 2.81 (s, 6H), 2.32 (s, 3H), 1.75-1.70 (m, 2H), 1.61 (d, J=6.0 Hz, 3H), 1.02 (t, J=7.2 Hz, 3H).

Step 6. (R)—N-(3-(2-(1-hydroxyethyl)imidazo[4,5-d]pyrrolo[2,3-b]pyridin-1(6H)-yl)bicyclo[1.1.1]pentan-1-yl)propane-1-sulfonamide (47)

To a solution of compound 47f (55 mg, 0.10 mmol) in a mixture of MeOH and H₂O (5.5 mL, V:V=1:5) was added NaOH (12 mg, 0.30 mmol) in one portion. After stirring for 25 hours at 30° C., the reaction mixture was diluted with water (20 mL) and washed with DCM (20 mL*2). The separated aqueous layer was concentrated to dryness and the residue was purified by prep-HPLC (Method A) to afford title compound (10 mg, 16% yield) as a white solid. LC-MS (Method 1): $t_R$=2.98 min, m/z (M+H)⁺=390.2. $^1$H NMR (400 MHz, CD₃OD) δ 8.58 (s, 1H), 7.48 (s, 1H), 6.88 (s, 1H), 5.26 (s, 1H), 3.13 (s, 2H), 3.00 (s, 6H), 1.89-1.88 (m, 2H), 1.78 (s, 3H), 1.12 (s, 3H).

Example 48

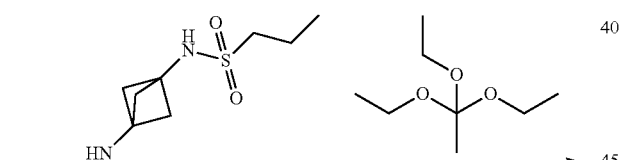

47e

48a

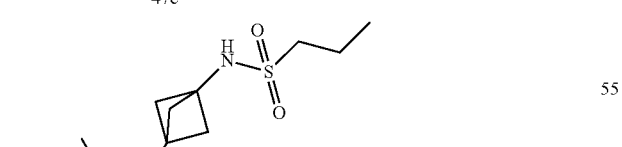

48

Step 1. N-(3-(2-methyl-6-tosylimidazo[4,5-d]pyrrolo[2,3-b]pyridin-1(6H)-yl)bicyclo[1.1.1]pentan-1-yl)propane-1-sulfonamide (48a)

Compound 48a (89 mg) was synthesized in 57% yield by utilizing similar preparative procedure of the fifth step of Example 1 with compound 47e (150 mg, 0.31 mmol) and 1,1,1-triethoxyethane (124 mg, 0.76 mmol) as starting materials. LC-MS (Method 3): $t_R$=1.52 min, m/z (M+H)⁺=514.1.

Step 2. N-(3-(2-methylimidazo[4,5-d]pyrrolo[2,3-b]pyridin-1(6H)-yl)bicyclo[1.1.1]pentan-1-yl)propane-1-sulfonamide (48)

To a solution of compound 48a (85 mg, 0.17 mmol) in MeOH and H₂O (3.3 mL, V:V=1:10) was added NaOH (20 mg, 0.50 mmol) in one portion. After stirring at 30° C. for 20 hrs, the reaction mixture was diluted with water (20 mL) and washed with DCM (20 mL*2). The separated aqueous layers were concentrated to dryness and residue was purified by prep-HPLC (Method A) to afford the title compound (5 μmg, 8% yield) as a white solid. LC-MS (Method 1): $t_R$=3.22 min, m/z (M+H)⁺=360.2. $^1$H NMR (400 MHz, CD₃OD) δ 8.36 (s, 1H), 7.37 (d, J=3.6 Hz, 1H), 6.73 (d, J=3.2 Hz, 1H), 3.05-3.01 (m, 2H), 2.84 (s, 6H), 2.62 (s, 3H), 1.80-1.75 (m, 2H), 1.01 (t, J=7.6 Hz, 3H).

Example 49

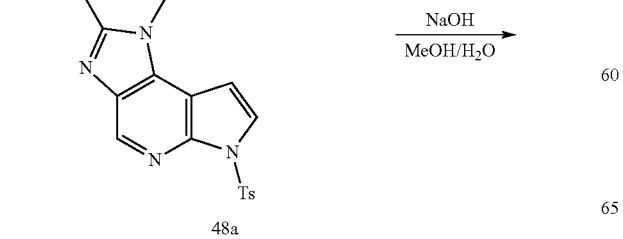

49a

49b

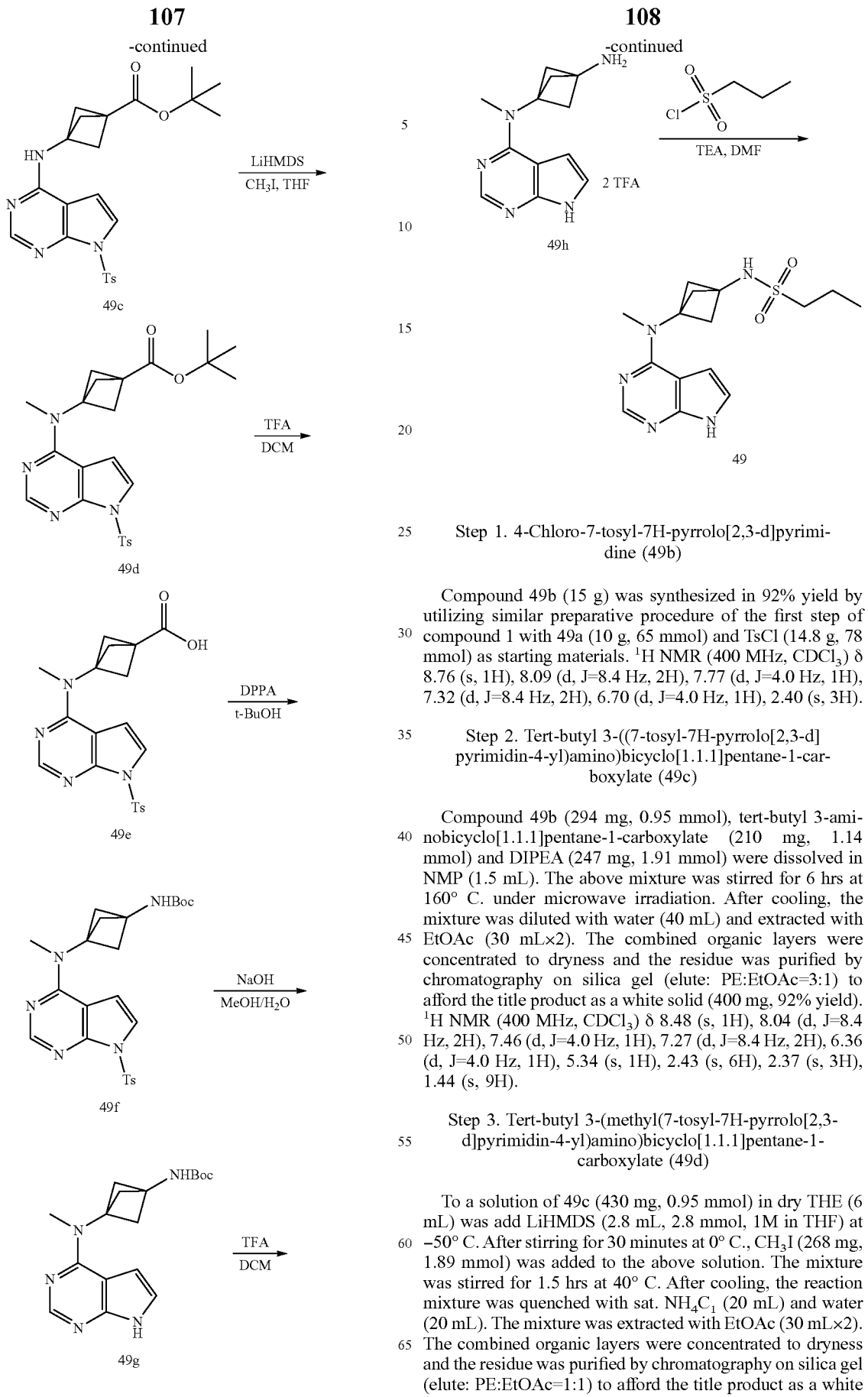

Step 1. 4-Chloro-7-tosyl-7H-pyrrolo[2,3-d]pyrimidine (49b)

Compound 49b (15 g) was synthesized in 92% yield by utilizing similar preparative procedure of the first step of compound 1 with 49a (10 g, 65 mmol) and TsCl (14.8 g, 78 mmol) as starting materials. $^1$H NMR (400 MHz, CDCl$_3$) δ 8.76 (s, 1H), 8.09 (d, J=8.4 Hz, 2H), 7.77 (d, J=4.0 Hz, 1H), 7.32 (d, J=8.4 Hz, 2H), 6.70 (d, J=4.0 Hz, 1H), 2.40 (s, 3H).

Step 2. Tert-butyl 3-((7-tosyl-7H-pyrrolo[2,3-d]pyrimidin-4-yl)amino)bicyclo[1.1.1]pentane-1-carboxylate (49c)

Compound 49b (294 mg, 0.95 mmol), tert-butyl 3-aminobicyclo[1.1.1]pentane-1-carboxylate (210 mg, 1.14 mmol) and DIPEA (247 mg, 1.91 mmol) were dissolved in NMP (1.5 mL). The above mixture was stirred for 6 hrs at 160° C. under microwave irradiation. After cooling, the mixture was diluted with water (40 mL) and extracted with EtOAc (30 mL×2). The combined organic layers were concentrated to dryness and the residue was purified by chromatography on silica gel (elute: PE:EtOAc=3:1) to afford the title product as a white solid (400 mg, 92% yield). $^1$H NMR (400 MHz, CDCl$_3$) δ 8.48 (s, 1H), 8.04 (d, J=8.4 Hz, 2H), 7.46 (d, J=4.0 Hz, 1H), 7.27 (d, J=8.4 Hz, 2H), 6.36 (d, J=4.0 Hz, 1H), 5.34 (s, 1H), 2.43 (s, 6H), 2.37 (s, 3H), 1.44 (s, 9H).

Step 3. Tert-butyl 3-(methyl(7-tosyl-7H-pyrrolo[2,3-d]pyrimidin-4-yl)amino)bicyclo[1.1.1]pentane-1-carboxylate (49d)

To a solution of 49c (430 mg, 0.95 mmol) in dry THF (6 mL) was add LiHMDS (2.8 mL, 2.8 mmol, 1M in THF) at −50° C. After stirring for 30 minutes at 0° C., CH$_3$I (268 mg, 1.89 mmol) was added to the above solution. The mixture was stirred for 1.5 hrs at 40° C. After cooling, the reaction mixture was quenched with sat. NH$_4$C$_1$ (20 mL) and water (20 mL). The mixture was extracted with EtOAc (30 mL×2). The combined organic layers were concentrated to dryness and the residue was purified by chromatography on silica gel (elute: PE:EtOAc=1:1) to afford the title product as a white solid (125 mg, 28% yield). $^1$H NMR (400 MHz, CDCl$_3$) δ 8.39 (s, 1H), 8.04 (d, J=8.0 Hz, 2H), 7.45 (d, J=4.0 Hz, 1H), 7.27 (d, J=8.4 Hz, 2H), 6.63 (d, J=4.0 Hz, 1H), 3.25 (s, 3H), 2.47. (s, 6H), 2.37 (s, 3H), 1.46 (s, 9H).

Step 4. 3-(Methyl(7-tosyl-7H-pyrrolo[2,3-d]pyrimidin-4-yl)amino)bicyclo[1.1.1]pentane-1-carboxylic acid (49e)

Compound 49e (154 mg) was synthesized in 100% yield by utilizing similar preparative procedure of the sixth step of compound 1 with 49d (175 mg, 0.37 mmol) as starting materials. LC-MS (Method 2): $t_R$=1.62 min, m/z (M+H)$^+$=412.9

Step 5. Tert-butyl (3-(methyl(7-tosyl-7H-pyrrolo[2,3-d]pyrimidin-4-yl)amino)bicyclo[1.1.1]pentan-1-yl)carbamate (49f)

Compound 49f (120 mg) was synthesized in 66% yield by utilizing similar preparative procedure of the seventh step of compound 1 with 49e (154 mg, 0.37 mmol) as starting materials. LC-MS (Method 2): $t_R$=1.85 min, m/z (M+H)$^+$=484.2.

Step 6. Tert-butyl (3-(methyl(7H-pyrrolo[2,3-d]pyrimidin-4-yl)amino)bicyclo[1.1.1]pentan-1-yl)carbamate (49g)

Compound 49g (40 mg) was synthesized in 49% yield by utilizing similar preparative procedure of the eighth step of compound 1 with 49f (120 mg, 0.25 mmol) as starting materials. LC-MS (Method 2): $t_R$=1.50 min, m/z (M+H)$^+$=330.2.

Step 7. N-Methyl-N-(7H-pyrrolo[2,3-d]pyrimidin-4-yl)bicyclo[1.1.1]pentane-1,3-diamine 2,2,2-trifluoroacetate (49h)

Compound 49h (55 mg crude) was synthesized in 100% yield by utilizing similar preparative procedure of the ninth step of compound 1 with 49g (40 mg, 0.12 mmol) as starting materials. LC-MS (Method 2): $t_R$=0.22 min, m/z (M+H)$^+$=230.0.

Step 8. N-(3-(Methyl(7H-pyrrolo[2,3-d]pyrimidin-4-yl)amino)bicyclo[1.1.1]pentan-1-yl)propane-1-sulfonamide (49)

Compound 49 (1.8 mg) was synthesized in 4% yield by utilizing similar preparative procedure of the final step of compound 1 with 49h (55 mg crude, 0.12 mmol) and propane-1-sulfonyl chloride (21 mg, 0.15 mmol) as starting materials. LC-MS (Method 1): $t_R$=2.72 min, m/z (M+H)$^+$=336.1. $^1$H NMR (400 MHz, CD$_3$OD) δ 8.15 (s, 1H), 7.07 (d, J=3.6 Hz, 1H), 6.62 (d, J=3.6 Hz, 1H), 3.40 (s, 3H), 3.06-3.02 (m, 2H), 2.53 (s, 6H), 1.86-1.79 (m, 2H), 1.09 (t, J=7.6 Hz, 3H).

Example 50

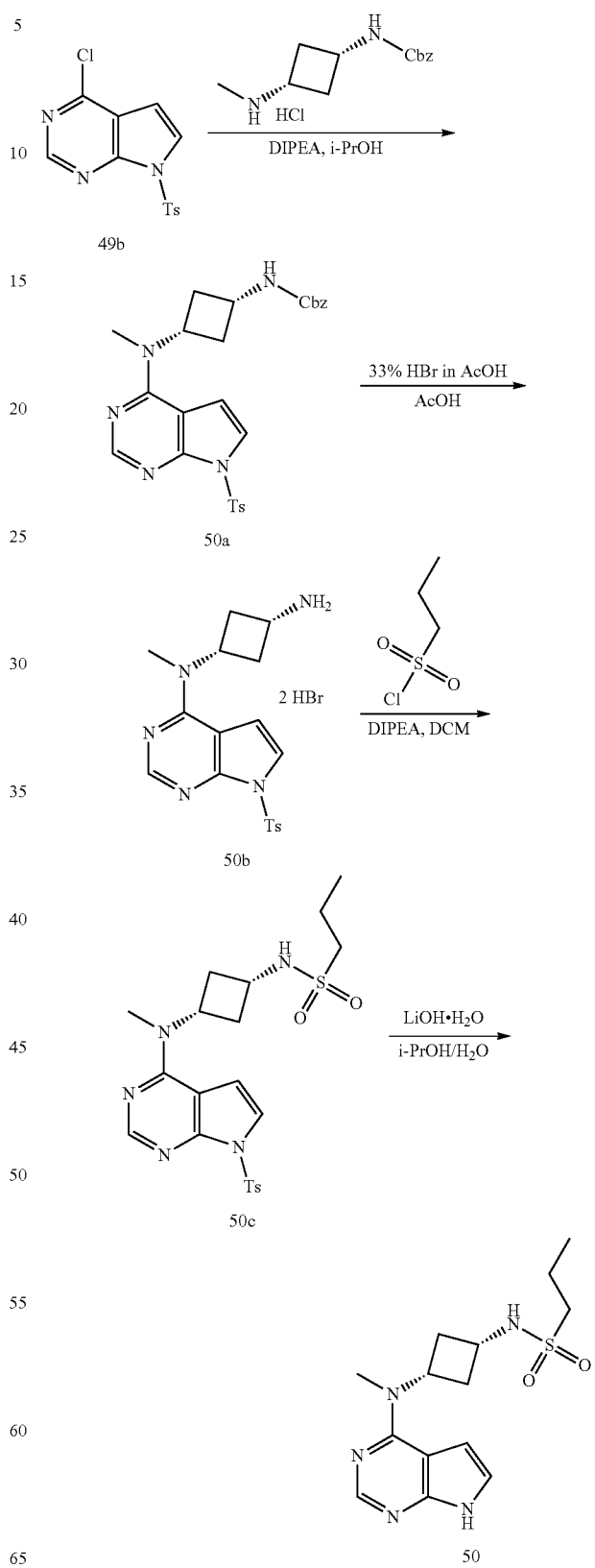

Step 1. Benzyl (cis-3-(methyl(7-tosyl-7H-pyrrolo[2,3-d]pyrimidin-4-yl)amino)cyclobutyl)carbamate (50a)

49b (420 mg, 1.36 mmol), benzyl ((cis)-3-(methylamino) cyclobutyl)carbamate hydrochloride (350 mg, 1.50 mmol) and DIPEA (614 mg, 4.76 mmol) were dissolved in i-PrOH (7 mL). The mixture was stirred at 75° C. for 7 hrs. Then the mixture was filtered. The filter cake was washed with i-PrOH and dried to afford the title product as a white solid (580 mg, 88% yield). LC-MS (Method 2): $t_R$=1.79 min, m/z (M+H)$^+$=506.2.

Step 2. Cis-N$^1$-methyl-N$^1$-(7-tosyl-7H-pyrrolo[2,3-d]pyrimidin-4-yl)cyclobutane-1,3-diamine hydrobromide (50b)

Compound 50a (250 mg, 0.49 mmol) were dissolved in HBr (7 mL, 33% in $CH_3COOH$) and $CH_3COOH$ (2 mL). The solution was stirred at 90° C. for 0.5 hr. The mixture was concentrated to dryness to afford the crude title product as a brown solid (170 mg crude, 65% yield). LC-MS (Method 2): $t_R$=1.34 min, m/z (M+H)$^+$=372.1.

Step 3. N-(cis-3-(methyl(7-tosyl-7H-pyrrolo[2,3-d]pyrimidin-4-yl)amino)cyclobutyl)propane-1-sulfonamide (50c)

To a mixture of 50b (170 mg crude, 0.46 mmol) and DIPEA (614 mg, 4.76 mmol) in DCM (8 mL) was added 3-cyanoazetidine-1-sulfonyl chloride (163 mg, 1.14 mmol) at 0° C. After stirring for 3 hrs at RT, the mixture was diluted with water (70 mL) and extracted with DCM (50 mL). The separated organic layer was concentrated to dryness to afford the crude title product as a brown solid (218 mg, 100% yield). LC-MS (Method 2): $t_R$=1.58 min, m/z (M+H)+=478.1.

Step 4. N-(cis-3-(methyl(7H-pyrrolo[2,3-d]pyrimidin-4-yl)amino)cyclobutyl)propane-1-sulfonamide (50)

50c (215 mg, 0.45 mmol) was dissolved in i-PrOH and $H_2O$ (5.8 mL, V:V=25:4) followed by the addition of LiOH $H_2O$ (95 mg, 2.25 mmol) in one portion. The mixture was stirred at 60° C. for 13 hrs, diluted with water (30 mL) and then extracted with EtOAc (50 mL). The separated organic layer was concentrated to dryness. The residue was purified by prep-HPLC (Method A) to afford the title product as a white solid (50.0 mg, 35% yield). LC-MS (Method 1): $t_R$=2.80 min, m/z (M+H)$^+$=324.1; $^1$H NMR (400 MHz, DMSO-$d_6$) δ 11.62 (s, 1H), 8.10 (s, 1H), 7.48 (d, J=9.2 Hz, 1H), 7.15-7.14 (m, 1H), 6.63 (d, J=1.2 Hz, 1H), 4.92-4.88 (m, 1H), 3.60-3.54 (m, 1H), 3.25 (s, 3H), 2.94 (t, J=7.6 Hz, 2H), 2.62-2.60 (m, 2H), 2.26-2.19 (m, 2H), 1.73-1.64 (m, 2H), 0.98 (t, J=7.6 Hz, 3H).

Biochemical Assay

JAK activity was determined in the reaction buffer 50 mM HEPES, 0.01% Brij35, 10 mM MgCl2, 2 mM DTT by a microfluidic assay. The phosphorylation of a FAM labeled peptide substrate was monitored in the Caliper EZ Reader II (Perkin Elmer). The assay condition for each batch of enzyme (Carna Biosciences) was optimized to obtain 10% conversion rate of peptide substrate.

The test compounds were dissolved in DMSO to a stock concentration of 10 mM. Three-fold serially diluted compounds with top concentration of 5 μM were pre-incubated with JAK1, JAK2 or TYK2 for 10 min at ambient temperature. The final DMSO concentration of assay mixture was 1%. FAM labeled peptide substrate (final concentration 3 μM) and ATP (Km concentration or 1 mM) were sequentially added to initiate the kinase reaction at 28° C. The reaction was stopped by adding 50 mM EDTA.

The well in the test plate without enzyme was defined as 100% inhibition. And the well without compound but with equivalent DMSO was defined as no inhibition. The percent inhibition was calculated by the following formula.

$$\% \text{ Inhibition} = (\text{Conversion}_{max} - \text{Conversion}_{sample}) / (\text{Conversion}_{max} - \text{Conversion}_{min}) * 100$$

Conversion$_{max}$ means the conversion rate in the positive well without addition of compound Conversion$_{sample}$ means the conversion rate in the well without addition of enzyme Conversion$_{sample}$ means the conversion rate of test compounds The dose-response (percent inhibition) curve was plotted and IC50 values were determined by GraphPad software. The IC50 values of tested compounds were list in Table 2.

TABLE 2

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 1 | N-(3-(imidazo[4,5-d]pyrrolo[2,3-b]pyridin-1(6H)-yl)bicyclo[1.1.1]pentan-1-yl)propane-1-sulfonamide | 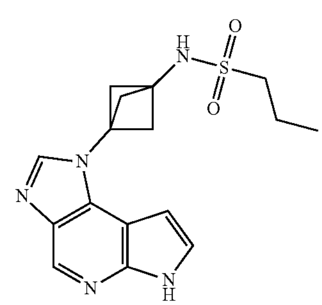 [SMILES: CCCS(=O)(=O)NC12CC(n3cnc4cnc5[nH]ccc5c43)(C1)C2] | 5.95 | 141.3 | 119.0 |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 2 | N-(Cis-3-(imidazo[4,5-d]pyrrolo[2,3-b]pyridin-1(6H)-yl)cyclobutyl)propane-1-sulfonamide | 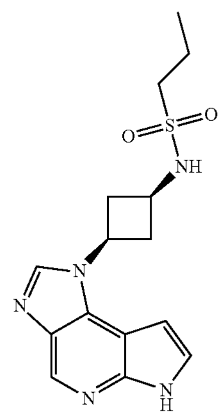 [SMILES: CCCS(=O)(=O)N[C@H]1C[C@@H](n2cnc3cnc4[nH]ccc4c32)C1] | 69.22 | 1086.5 | 2849.0 |
| 3 | N-(trans-3-(imidazo[4,5-d]pyrrolo[2,3-b]pyridin-1(6H)-yl)cyclobutyl)propane-1-sulfonamide | 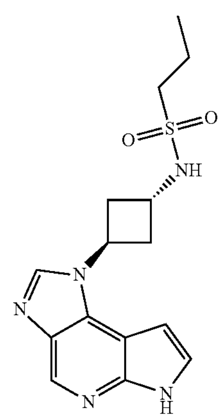 [SMILES: CCCS(=O)(=O)N[C@H]1C[C@H](n2cnc3cnc4[nH]ccc4c32)C1] | 190.1 | 1538.0 | 3658.0 |
| 4 | 3-cyano-N-(3-(imidazo[4,5-d]pyrrolo[2,3-b]pyridin-1(6H)-yl)bicyclo[1.1.1]pentan-1-yl)azetidine-1-sulfonamide | 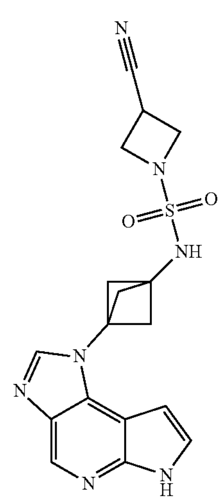 [SMILES: N#CC1CN(S(=O)(=O)NC23CC(n4cnc5cnc6[nH]ccc6c54)(C2)C3)C1] | 3.20 | 83.2 | 111.0 |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 5 | N-(3-(imidazo[4,5-d]pyrrolo[2,3-b]pyridin-1(6H)-yl)bicyclo[1.1.1]pentan-1-yl)-2-methylpropane-1-sulfonamide | 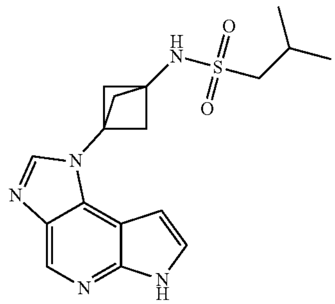 [SMILES: CC(C)CS(=O)(=O)NC12CC(n3cnc4cnc5[nH]ccc5c43)(C1)C2] | 5.53 | 145.2 | 111.0 |
| 6 | N-(3-(imidazo[4,5-d]pyrrolo[2,3-b]pyridin-1(6H)-yl)bicyclo[1.1.1]pentan-1-yl)-2-methoxyethane-1-sulfonamide | 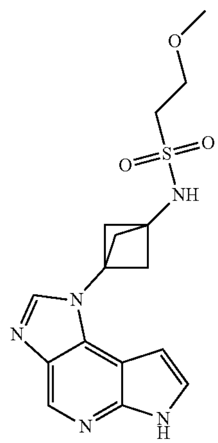 [SMILES: COCCS(=O)(=O)NC12CC(n3cnc4cnc5[nH]ccc5c43)(C1)C2] | 24.4 | 597.1 | 1054.0 |
| 7 | N-(3-(imidazo[4,5-d]pyrrolo[2,3-b]pyridin-1(6H)-yl)bicyclo[1.1.1]pentan-1-yl)cyclopropane-sulfonamide | 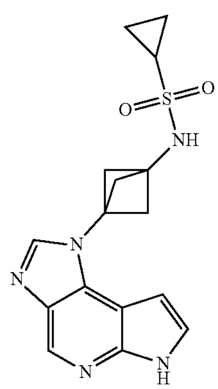 [SMILES: O=S(=O)(NC12CC(n3cnc4cnc5[nH]ccc5c43)(C1)C2)C1CC1] | 45.3 | 469.7 | 574.0 |
| 8 | N-(3-(imidazo[4,5-d]pyrrolo[2,3-b]pyridin-1(6H)-yl)bicyclo[1.1.1]pentan-1-yl)-3-methylbutanamide | 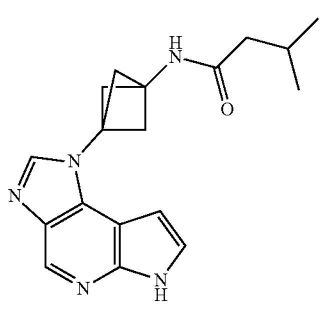 [SMILES: CC(C)CC(=O)NC12CC(n3cnc4cnc5[nH]ccc5c43)(C1)C2] | 47.4 | 328.3 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 9 | N-(3-(imidazo[4,5-d]pyrrolo[2,3-b]pyridin-1(6H)-yl)bicyclo[1.1.1]pentan-1-yl)butyramide | 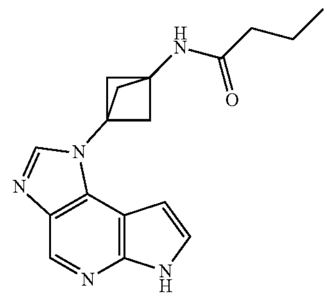 [SMILES: CCCC(=O)NC12CC(n3cnc4cnc5[nH]ccc5c43)(C1)C2] | 58.7 | 440.6 | — |
| 10 | isobutyl (3-(imidazo[4,5-d]pyrrolo[2,3-b]pyridin-1(6H)-yl)bicyclo[1.1.1]pentan-1-yl)carbamate | 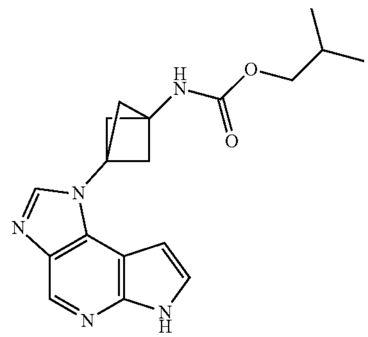 [SMILES: CC(C)COC(=O)NC12CC(n3cnc4cnc5[nH]ccc5c43)(C1)C2] | 164.5 | 867.8 | — |
| 11 | 2-cyano-N-(3-(imidazo[4,5-d]pyrrolo[2,3-b]pyridin-1(6H)-yl)bicyclo[1.1.1]pentan-1-yl)acetamide | 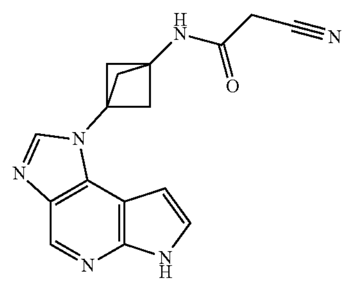 [SMILES: N#CCC(=O)NC12CC(n3cnc4cnc5[nH]ccc5c43)(C1)C2] | 11.7 | 165.7 | — |
| 12 | N-(3-(imidazo[4,5-d]pyrrolo[2,3-b]pyridin-1(6H)-yl)bicyclo[1.1.1]pentan-1-yl)cyclopropane-carboxamide | 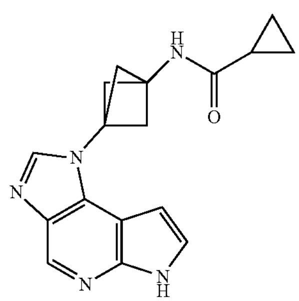 [SMILES: O=C(NC12CC(n3cnc4cnc5[nH]ccc5c43)(C1)C2)C1CC1] | 35.5 | — | — |
| 13 | 2-cyclopropyl-N-(3-(imidazo[4,5-d]pyrrolo[2,3-b]pyridin-1(6H)-yl)bicyclo[1.1.1]pentan-1-yl)acetamide | 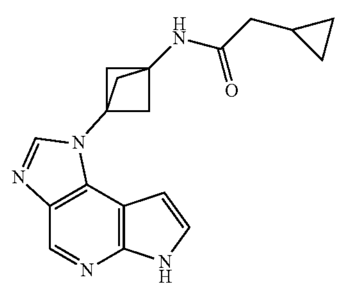 [SMILES: O=C(CC1CC1)NC12CC(n3cnc4cnc5[nH]ccc5c43)(C1)C2] | 14.8 | 121.9 | 400.5 |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 14 | 3-cyano-N-(3-(imidazo[4,5-d]pyrrolo[2,3-b]pyridin-1(6H)-yl)bicyclo[1.1.1]pentan-1-yl)propanamide | 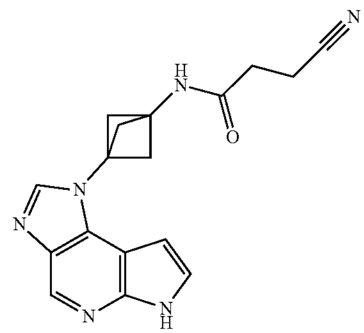 [SMILES: N#CCCC(=O)NC12CC(n3cnc4cnc5[nH]ccc5c43)(C1)C2] | 8.06 | 73.1 | — |
| 15 | 4-chloro-N-(3-(imidazo[4,5-d]pyrrolo[2,3-b]pyridin-1(6H)-yl)bicyclo[1.1.1]pentan-1-yl)benzamide | 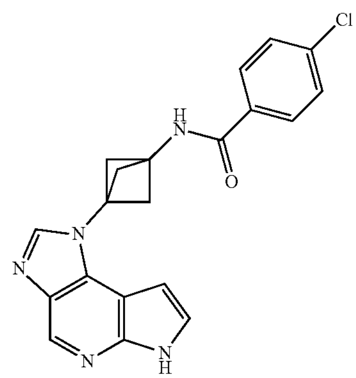 [SMILES: O=C(NC12CC(n3cnc4cnc5[nH]ccc5c43)(C1)C2)c1ccc(Cl)cc1] | 82.6 | — | — |
| 16 | isopropyl (3-(imidazo[4,5-d]pyrrolo[2,3-b]pyridin-1(6H)-yl)bicyclo[1.1.1]pentan-1-yl)carbamate | 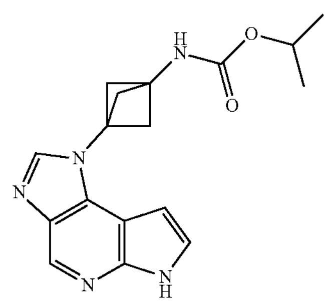 [SMILES: CC(C)OC(=O)NC12CC(n3cnc4cnc5[nH]ccc5c43)(C1)C2] | 64.0 | — | — |
| 17 | 3,3-difluoro-N-(3-(imidazo[4,5-d]pyrrolo[2,3-b]pyridin-1(6H)-yl)bicyclo[1.1.1]pentan-1-yl)cyclobutane-1-carboxamide | 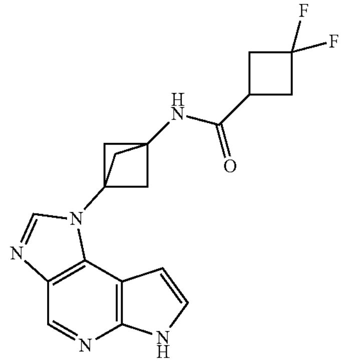 [SMILES: O=C(NC12CC(n3cnc4cnc5[nH]ccc5c43)(C1)C2)C1CC(F)(F)C1] | 8.4 | 89.5 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 18 | 4,4,4-trifluoro-N-(3-(imidazo[4,5-d]pyrrolo[2,3-b]pyridin-1(6H)-yl)bicyclo[1.1.1]pentan-1-yl)butanamide | 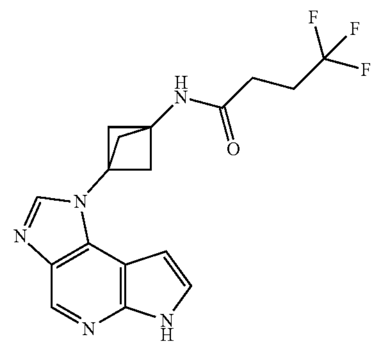 [SMILES: O=C(CCC(F)(F)F)NC12CC(n3cnc4cnc5[nH]ccc5c43)(C1)C2] | 18.7 | 167.2 | — |
| 19 | cyclopropylmethyl (3-(imidazo[4,5-d]pyrrolo[2,3-b]pyridin-1(6H)-yl)bicyclo[1.1.1]pentan-1-yl)carbamate | 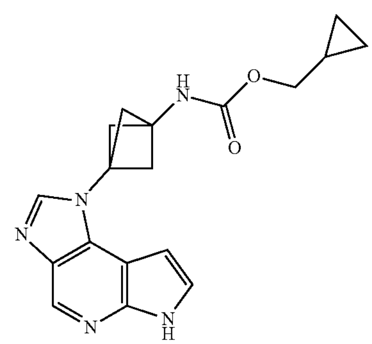 [SMILES: O=C(NC12CC(n3cnc4cnc5[nH]ccc5c43)(C1)C2)OCC1CC1] | 51.3 | 577.7 | — |
| 20 | 3-cyano-N-(3-(imidazo[4,5-d]pyrrolo[2,3-b]pyridin-1(6H)-yl)bicyclo[1.1.1]pentan-1-yl)pyrrolidine-1-sulfonamide | 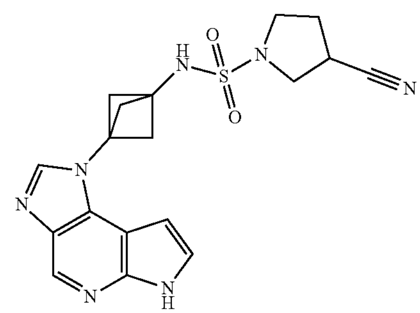 [SMILES: N#CC1CCN(S(=O)(=O)NC23CC(n4cnc5cnc6[nH]ccc6c54)(C2)C3)C1] | 8.3 | 334.4 | 200.3 |
| 21 | N-(3-(imidazo[4,5-d]pyrrolo[2,3-b]pyridin-1(6H)-yl)bicyclo[1.1.1]pentan-1-yl)-3-methoxyazetidine-1-sulfonamide | 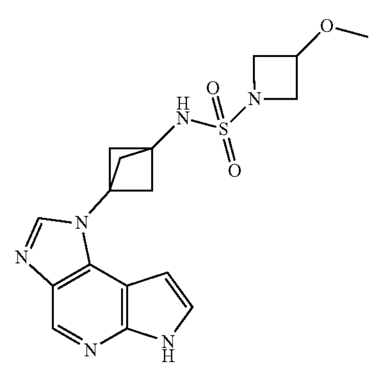 [SMILES: COC1CN(S(=O)(=O)NC23CC(n4cnc5cnc6[nH]ccc6c54)(C2)C3)C1] | 14.2 | 326.0 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 22 | 3-fluoro-N-(3-(imidazo[4,5-d]pyrrolo[2,3-b]pyridin-1(6H)-yl)bicyclo[1.1.1]pentan-1-yl)azetidine-1-sulfonamide | 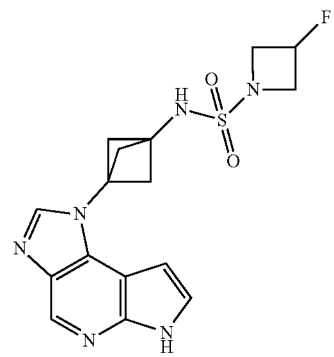 [SMILES: O=S(=O)(NC12CC(n3cnc4cnc5[nH]ccc5c43)(C1)C2)N1CC(F)C1] | 6.1 | 45.5 | 28.4 |
| 23 | 3,3-difluoro-N-(3-(imidazo[4,5-d]pyrrolo[2,3-b]pyridin-1(6H)-yl)bicyclo[1.1.1]pentan-1-yl)azetidine-1-sulfonamide | 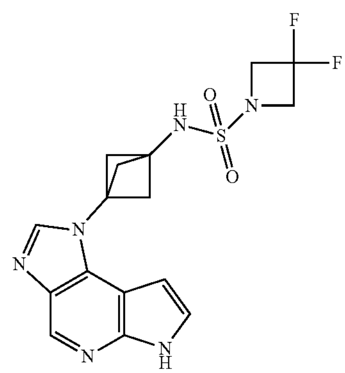 [SMILES: O=S(=O)(NC12CC(n3cnc4cnc5[nH]ccc5c43)(C1)C2)N1CC(F)(F)C1] | 3.4 | 50.8 | 33.5 |
| 24 | N-(3-(imidazo[4,5-d]pyrrolo[2,3-b]pyridin-1(6H)-yl)bicyclo[1.1.1]pentan-1-yl)-N'-dimethyl-1-sulfonamide | 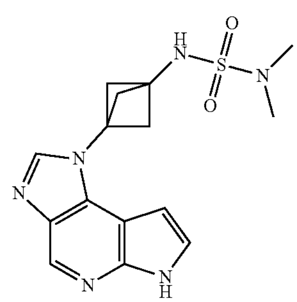 | 23.0 | — | — |
| 25 | N-(3-(imidazo[4,5-d]pyrrolo[2,3-b]pyridin-1(6H)-yl)bicyclo[1.1.1]pentan-1-yl)-N'-methyl-N'-ethyl-1-sulfonamide | 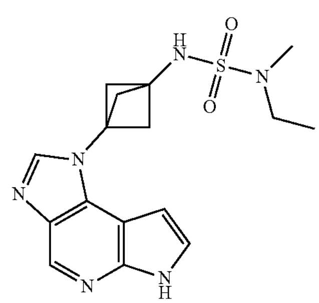 [SMILES: CCN(C)S(=O)(=O)NC12CC(n3cnc4cnc5[nH]ccc5c43)(C1)C2] | 26.1 | — | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 26 | N-(3-(imidazo[4,5-d]pyrrolo[2,3-b]pyridin-1(6H)-yl)bicyclo[1.1.1]pentan-1-yl)-3-methoxypropane-1-sulfonamide | 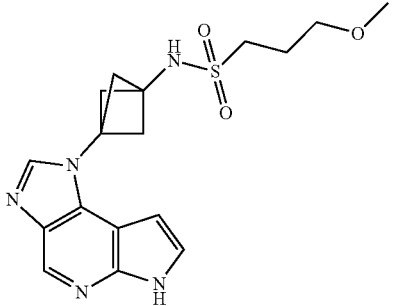 [SMILES: COCCCS(=O)(=O)NC12CC(n3cnc4cnc5[nH]ccc5c43)(C1)C2] | 26.2 | 849.4 | — |
| 27 | N-(3-(imidazo[4,5-d]pyrrolo[2,3-b]pyridin-1(6H)-yl)bicyclo[1.1.1]pentan-1-yl)ethanesulfonamide | 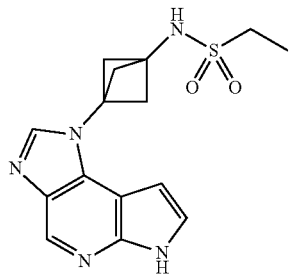 [SMILES: CCS(=O)(=O)NC12CC(n3cnc4cnc5[nH]ccc5c43)(C1)C2] | 20.2 | 291.3 | — |
| 28 | 4-chloro-N-(3-(imidazo[4,5-d]pyrrolo[2,3-b]pyridin-1(6H)-yl)bicyclo[1.1.1]pentan-1-yl)benzenesulfonamide | 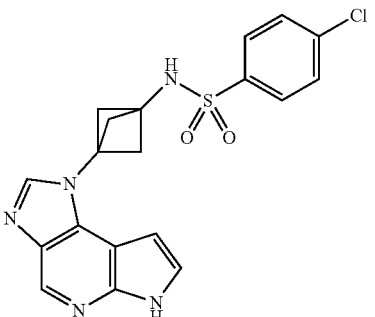 | 6.7 | 258.8 | 412.8 |
| 29 | N-(3-(imidazo[4,5-d]pyrrolo[2,3-b]pyridin-1(6H)-yl)bicyclo[1.1.1]pentan-1-yl)-1-methyl-1H-pyrazole-4-sulfonamide | 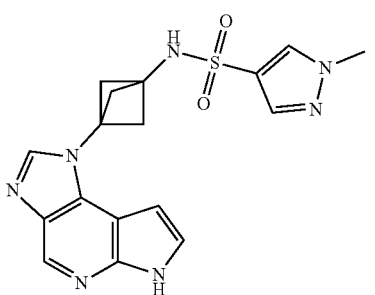 [SMILES: Cn1cc(S(=O)(=O)NC23CC(n4cnc5cnc6[nH]ccc6c54)(C2)C3)cn1] | 90.5 | 992.2 | — |
| 30 | N-(3-(imidazo[4,5-d]pyrrolo[2,3-b]pyridin-1(6H)-yl)bicyclo[1.1.1]pentan-1-yl)propane-2-sulfonamide | 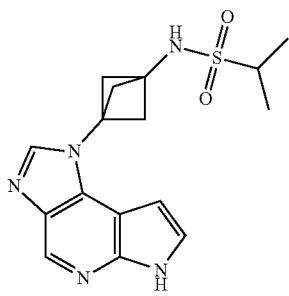 | 25.5 | 226.0 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 31 | N-(3-(imidazo[4,5-d]pyrrolo[2,3-b]pyridin-1(6H)-yl)bicyclo[1.1.1]pentan-1-yl)butane-1-sulfonamide | 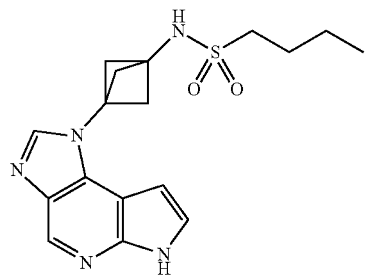 [SMILES: CCCCS(=O)(=O)NC12CC(n3cnc4cnc5[nH]ccc5c43)(C1)C2] | 4.8 | 129.4 | 169.7 |
| 32 | 3,3,3-trifluoro-N-(3-(imidazo[4,5-d]pyrrolo[2,3-b]pyridin-1(6H)-yl)bicyclo[1.1.1]pentan-1-yl)propane-1-sulfonamide | 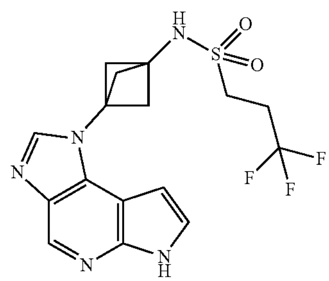 [SMILES: O=S(=O)(CCC(F)(F)F)NC12CC(n3cnc4cnc5[nH]ccc5c43)(C1)C2] | 6.7 | 155.0 | 151.3 |
| 33 | 1-cyano-N-(3-(imidazo[4,5-d]pyrrolo[2,3-b]pyridin-1(6H)-yl)bicyclo[1.1.1]pentan-1-yl)methanesulfonamide | 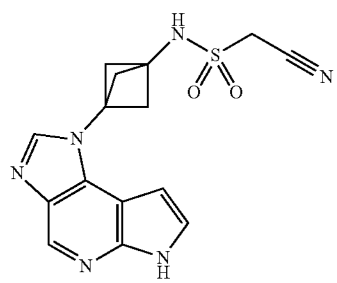 [SMILES: N#CCS(=O)(=O)NC12CC(n3cnc4cnc5[nH]ccc5c43)(C1)C2] | 14.4 | 146.4 | — |
| 34 | 1-(3-(imidazo[4,5-d]pyrrolo[2,3-b]pyridin-1(6H)-yl)bicyclo[1.1.1]pentan-1-yl)-3-propylurea | 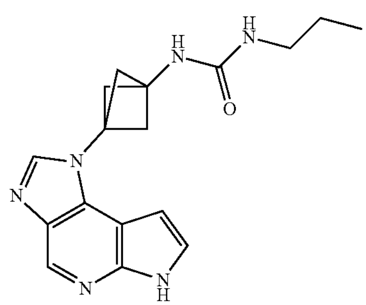 [SMILES: CCCNC(=O)NC12CC(n3cnc4cnc5[nH]ccc5c43)(C1)C2] | 25.4 | 198.9 | — |
| 35 | 1-cyclopropyl-3-(3-(imidazo[4,5-d]pyrrolo[2,3-b]pyridin-1(6H)-yl)bicyclo[1.1.1]pentan-1-yl)urea | 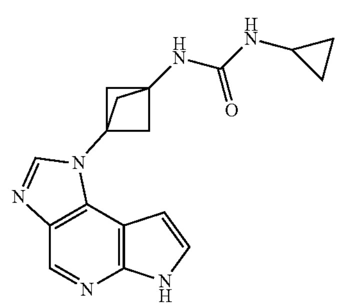 [SMILES: O=C(NC1CC1)NC12CC(n3cnc4cnc5[nH]ccc5c43)(C1)C2] | 234.8 | — | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 36 | 1-(3-(imidazo[4,5-d]pyrrolo[2,3-b]pyridin-1(6H)-yl)bicyclo[1.1.1]pentan-1-yl)-3-isobutylurea | 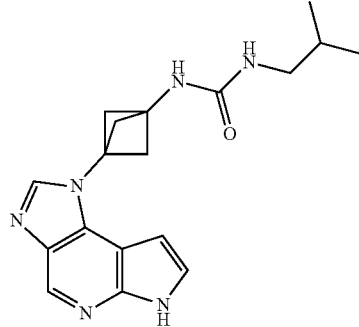 [SMILES: CC(C)CNC(=O)NC12CC(n3cnc4cnc5[nH]ccc5c43)(C1)C2] | 49.5 | — | — |
| 37 | 3,3-difluoro-N-(3-(imidazo[4,5-d]pyrrolo[2,3-b]pyridin-1(6H)-yl)bicyclo[1.1.1]pentan-1-yl)azetidine-1-carboxamide | 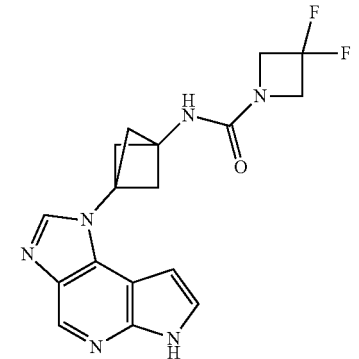 [SMILES: O=C(NC12CC(n3cnc4cnc5[nH]ccc5c43)(C1)C2)N1CC(F)(F)C1] | 100.7 | 677.7 | — |
| 38 | N-(3-(imidazo[4,5-d]pyrrolo[2,3-b]pyridin-1(6H)-yl)bicyclo[1.1.1]pentan-1-yl)-3-methoxyazetidine-1-carboxamide | 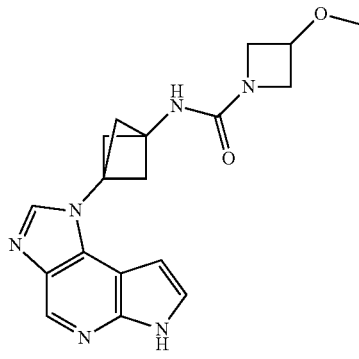 [SMILES: COC1CN(C(=O)NC23CC(n4cnc5cnc6[nH]ccc6c54)(C2)C3)C1] | 388.8 | 3305.0 | — |
| 39 | 3-cyano-N-(3-(imidazo[4,5-d]pyrrolo[2,3-b]pyridin-1(6H)-yl)bicyclo[1.1.1]pentan-1-yl)pyrrolidine-1-carboxamide | 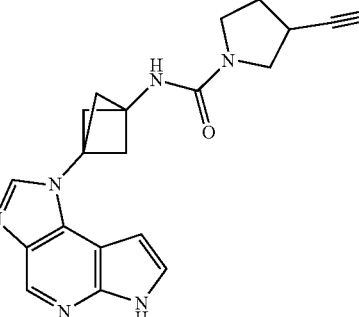 | 68.7 | 525.8 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 40 | 1-(2-cyano-2-methylpropyl)-3-(3-(imidazo[4,5-d]pyrrolo[2,3-b]pyridin-1(6H)-yl)bicyclo[1.1.1]pentan-1-yl)urea | 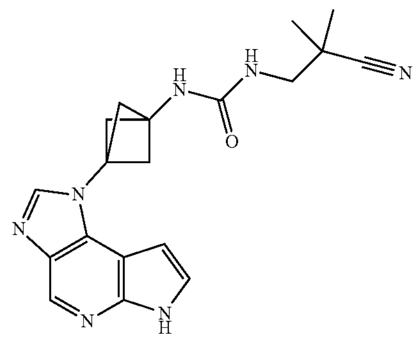 [SMILES: CC(C)(C#N)CNC(=O)NC12CC(n3cnc4cnc5[nH]ccc5c43)(C1)C2] | 49.4 | 354.9 | — |
| 41 | 1-(3-(imidazo[4,5-d]pyrrolo[2,3-b]pyridin-1(6H)-yl)bicyclo[1.1.1]pentan-1-yl)-3-(2,2,2-trifluoroethyl)urea | 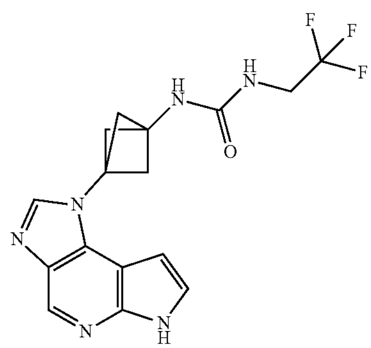 [SMILES: O=C(NCC(F)(F)F)NC12CC(n3cnc4cnc5[nH]ccc5c43)(C1)C2] | 8.5 | 94.6 | — |
| 42 | 2-cyano-2-methylpropyl (3-(imidazo[4,5-d]pyrrolo[2,3-b]pyridin-1(6H)-yl)bicyclo[1.1.1]pentan-1-yl)carbamate | 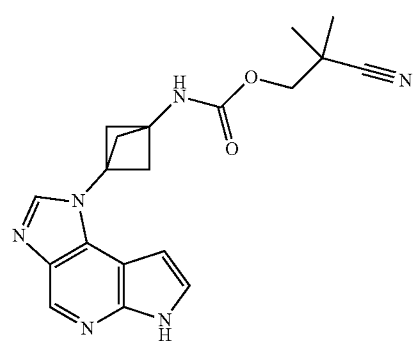 [SMILES: CC(C)(C#N)COC(=O)NC12CC(n3cnc4cnc5[nH]ccc5c43)(C1)C2] | 141.7 | 964.6 | — |
| 43 | 1-(2-cyanoethyl)-3-(3-(imidazo[4,5-d]pyrrolo[2,3-b]pyridin-1(6H)-yl)bicyclo[1.1.1]pentan-1-yl)urea | 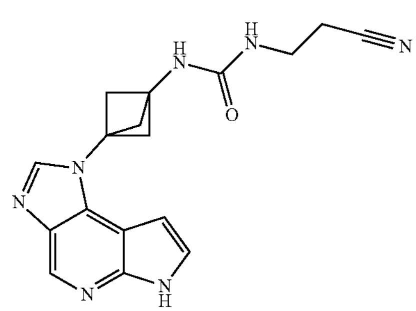 [SMILES: N#CCCNC(=O)NC12CC(n3cnc4cnc5[nH]ccc5c43)(C1)C2] | 15.6 | 223.3 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 44 | 1-((cis)-3-(imidazo[4,5-d]pyrrolo[2,3-b]pyridin-1(6H)-yl)cyclobutyl)-N-methylmethane-sulfonamide | 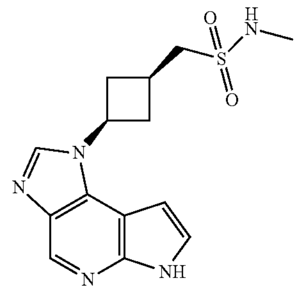 [SMILES: CNS(=O)(=O)C[C@H]1C[C@@H](n2cnc3cnc4[nH]ccc4c32)C1] | 159.2 | 604.5 | — |
| 45 | 1-((((cis)-3-(imidazo[4,5-d]pyrrolo[2,3-b]pyridin-1(6H)-yl)cyclobutyl)methyl)sulfonyl)azetidine-3-carbonitrile | 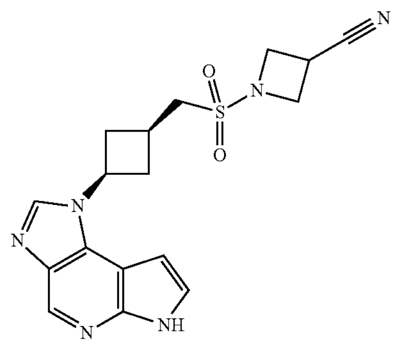 [SMILES: N#CC1CN(S(=O)(=O)C[C@H]2C[C@@H](n3cnc4cnc5[nH]ccc5c43)C2)C1] | 15.7 | 170.0 | — |
| 46 | 1-(3,3-difluorocyclobutyl)-N-(3-(imidazo[4,5-d]pyrrolo[2,3-b]pyridin-1(6H)-yl)bicyclo[1.1.1]pentan-1-yl)methanesulfonamide | 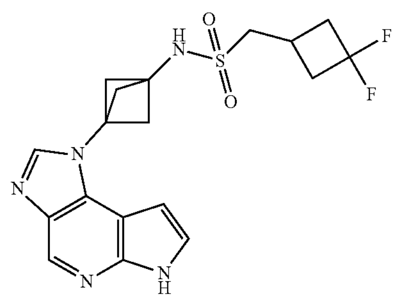 [SMILES: O=S(=O)(CC1CC(F)(F)C1)NC12CC(n3cnc4cnc5[nH]ccc5c43)(C1)C2] | 2.2 | 78.3 | 108.0 |
| 47 | (R)-N-(3-(2-(1-hydroxyethyl)imidazo[4,5-d]pyrrolo[2,3-b]pyridin-1(6H)-yl)bicyclo[1.1.1]pentan-1-yl)propane-1-sulfonamide | 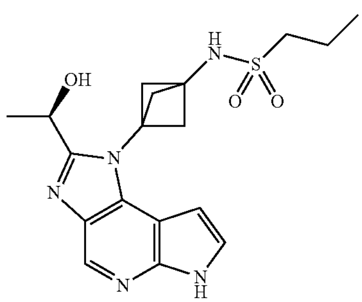 [SMILES: CCCS(=O)(=O)NC12CC(n3c([C@@H](C)O)nc4cnc5[nH]ccc5c43)(C1)C2] | 48.7 | 1108.0 | — |
| 48 | N-(3-(2-methylimidazo[4,5-d]pyrrolo[2,3-b]pyridin-1(6H)-yl)bicyclo[1.1.1]pentan-1-yl)propane-1-sulfonamide | 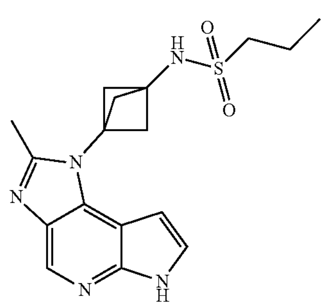 [SMILES: CCCS(=O)(=O)NC12CC(n3c(C)nc4cnc5[nH]ccc5c43)(C1)C2] | 13.0 | 244.1 | — |

TABLE 2-continued

| Example | Name | Structure | JAK1 (5 nM) (1 mM ATP) | JAK2 (0.25 nM) (1 mM ATP) | TYK2 (2.5 nM) (1 mM ATP) |
|---|---|---|---|---|---|
| 49 | N-(3-(Methyl(7H-pyrrolo[2,3-d]pyrimidin-4-yl)amino)bicyclo[1.1.1]pentan-1-yl)propane-1-sulfonamide | 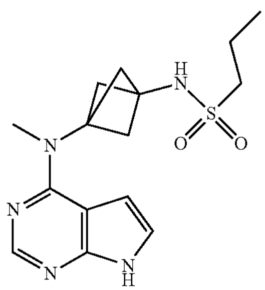 [SMILES: CCCS(=O)(=O)NC12CC(N(C)c3ncnc4[nH]ccc34)(C1)C2] | >5000 | >5000 | — |
| 50 | N-(cis-3-(methyl(7H-pyrrolo[2,3-d]pyrimidin-4-yl)amino)cyclobutyl)propane-1-sulfonamide | 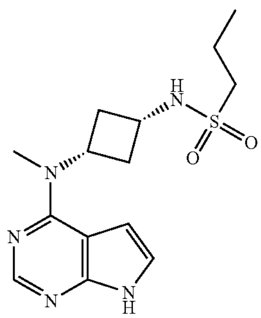 [SMILES: CCCS(=O)(=O)N[C@H]1C[C@@H](N(C)c2ncnc3[nH]ccc23)C1] | 44.1 | 708.9 | 1102.5 |
| 1j | 3-(imidazo[4,5-d]pyrrolo[2,3-b]pyridin-1(6H)-yl)bicyclo[1.1.1]pentan-1-amine | 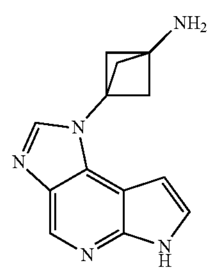 [SMILES: NC12CC(n3cnc4cnc5[nH]ccc5c43)(C1)C2] | 277.9 | — | — |
| 1i | tert-butyl (3-(imidazo[4,5-d]pyrrolo[2,3-b]pyridin-1(6H)-yl)bicyclo[1.1.1]pentan-1-yl)carbamate | 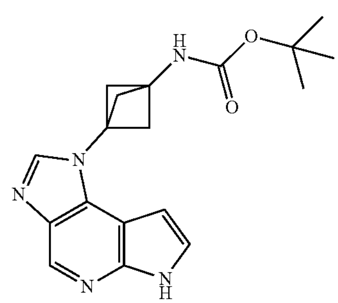 [SMILES: CC(C)(C)OC(=O)NC12CC(n3cnc4cnc5[nH]ccc5c43)(C1)C2] | 43.0 | 472.0 | 2884.0 |
| 2e | (cis)-3-(imidazo[4,5-d]pyrrolo[2,3-b]pyridin-1(6H)-yl)cyclobutan-1-amine | 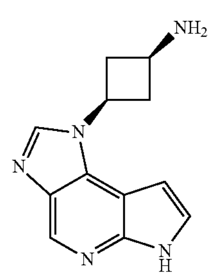 [SMILES: N[C@H]1C[C@@H](n2cnc3cnc4[nH]ccc4c32)C1] | 2570.0 | >5000 | — |

Anti-Proliferative Assay

Dimerization domain of Tel protein fused with JAK kinase domain was permanently transduced into BaF3 cells, whose proliferation is dependent on JAK activity in the absence of IL-3 induction. These engineered BaF3-Tel-JAK cells were used to monitor JAK inhibitory activities of the compounds in the cellular.

BaF3-Tel-JAK cells were cultured in RPMI-1640 (Corning) containing 10% fetal bovine serum. Cells were seeded at 2000/well of white flat bottom 96-well plates. The well containing medium only was used as background control. After 24h growth, cells were treated with compounds. The test compounds were dissolved in DMSO to a stock concentration of 10 mM. 3-fold serially diluted compounds for 9 concentrations with top concentration of 10 μM was added into the each well. The final DMSO concentration was 0.2%. The cells continued to grow at 37° C. in 5% $CO_2$ for 72 h after compound treatment. The viability was measured by cellular ATP determination using the Cell-Titer Glo luciferase reagent (Promega). The Luminescence value was recorded by a multi-label reader Envision (PerkinElmer). Values were transformed to percent inhibition using the following formula.

$$\% \text{ Inhibition} = (\text{Readout}_{max} - \text{Readout}_{sample}) / (\text{Readout}_{max} - \text{Readout}_{min}) * 100$$

The well without compound but with equivalent DMSO was defined as Readout max

The well with only medium and equivalent DMSO was defined as Readout min

The dose-response (percent inhibition) curve was plotted and GI50 values (the concentration that causes 50% growth inhibition) were determined by GraphPad software. The GI50 of tested compounds are shown in Table 3.

TABLE 3

| Example | BaF3-TEL-JAK1 (nM) | BaF3-TEL-JAK2 (nM) |
|---|---|---|
| 1 | 19.6 | 354 |
| 2 | 352 | 2300 |
| 3 | 1090 | 2536 |
| 5 | 10 | 380 |
| 13 | 50.1 | 107.5 |
| 17 | 48.2 | 86.7 |
| 18 | 120.3 | 291.1 |
| 22 | 54.0 | 163.2 |
| 23 | 41.6 | 148.4 |
| 28 | 51 | 285.6 |
| 31 | 27.8 | 198.2 |
| 32 | 33.6 | 121.7 |
| 41 | 99.6 | 999.6 |
| 46 | 14.2 | 132.7 |

Human Liver Microsome Stability Study:

Commercially available human liver microsome (vendor: Corning) were used for study the Phase I stability of test articles.

Microsomes were pre-incubated with test compound or control compounds for 10 min at 37° C. in 100 mM potassium phosphate buffer, pH 7.4, 3.3 mM MgCl2. The reaction was initiated by addition of 80 μL of the NADPH regenerating system to 320 μL of each incubation mixture per time point. The final incubation condition was composed of 0.5 mg/mL microsomal protein, 1 μM test article/positive control, 1.3 mM NADP, 3.3 mM glucose-6-phosphate, and 0.6 U/mL glucose-6-phosphate dehydrogenase. The 0-minute samples were prepared by addition of an 80 μL aliquot of each incubation mixture to 400 μL quench reagent to precipitate proteins. And then a 20 μL aliquot of the NADPH regenerating system was added. At 10, 30, and 90 minutes, the reaction will be stopped by the addition of cold acetonitrile solution containing tolbutamide and propanolol served as internal standard. The samples taken at all time points were centrifuged at 4000×g for 15 minutes. 80 μL of supernatant are taken into 96-well assay plates pre-added with 160 μL ultrapure water, and then analyzed by LC/MS/MS (Shimadzu LC30AD & API4000/API5000)).

Concentrations of test articles, control compounds in the samples were determined by using LC/MS/MS) method. Plotting of the chromatograms and peak area integrations are carried out by Analyst (AB Sciex).

In the determination of the in vitro elimination constant, ke, of the control compounds, the analyte/internal standard peak area ratios will be converted to percentage remaining (% Remaining) with the following equation:

$$\% \text{ Remaining} = \frac{\text{Peak area ratio of analyte to IS at each time point}}{\text{Peak area ratio of analyte to } IS \text{ at } t = 0} \times 100\%$$

The CLint of microsomes was calculated using the formula: CLint (mic)=0.693/T1/2/mg microsome protein per mL. Exemplary results are summarized in Table 4.

TABLE 4

| Example | HLM T½ (min) | HLM Clint (uL/min/mg) |
|---|---|---|
| 1 | 341.30 | 4.10 |
| 4 | 655.42 | 2.11 |
| 13 | 1377.09 | 1.01 |
| 14 | 1788.64 | 0.77 |
| 17 | 1339.12 | 1.04 |
| 22 | 1114.82 | 1.24 |
| 32 | 509.78 | 2.72 |
| 50 | 63.70 | 21.76 |

Rat Pharmacokinetic Study:

Pharmacokinetic profile of test articles were evaluated in fasted Sprague-Dawley rats. Typically, Rats were dosed with 1 mg/kg and 2 mg/kg by intravenous injection and oral gavage, respectively. After dosing, blood samples were collected at each time point. For IV injection group, time points were set at 5, 15, 30 min, and then 1, 2, 4, 8 and 24 hours after dosing. For oral gavage group, time points were set at 15, 30 min, and then 1, 2, 4, 8, and 24 hours. Blood was collected into appropriately labeled tubes containing K2EDTA as the anticoagulant. Plasma was obtained within 1 hours of blood collection by centrifugation at 8000×g and 4° C. for 6 minutes, and then stored at −20° C. until analyzed by LC/MS/MS for quantification.

PK parameter values, including, but not necessarily limited to, the maximum plasma concentrations (Cmax), the time to reach the maximum concentrations (Tmax), and the area under the plasma concentration vs. time curve (AUC)

from time zero to 24-hour (AUC0-24h) were determined using WinNonlin program. Exemplary results are summarized in Table 5.

TABLE 5

Administration Route
Rat iv @1 mpk
0.2 mg/mL in 5% DMSO + 15% Solutol HS 15 + 80% Saline

| Formulation | AUC (h*ng/ml) | t½ (h) | Cl (mL/min/Kg) | Vd (L/Kg) |
|---|---|---|---|---|
| Example 1 | 458.10 | 0.46 | 36.20 | 1.42 |

Administration Route
Rat iv @1 mpk
0.2 mg/mL in 4% DMSO + 15% Solutol HS 15 + 81% Saline

| Formulation | AUC (h*ng/ml) | t½ (h) | Cl (mL/min/Kg) | Vd (L/Kg) |
|---|---|---|---|---|
| Example 4 | 401.70 | 0.26 | 41.90 | 0.93 |

Administration Route
Rat po @2 mpk
0.2 mg/mL in 5% DMSO + 15% Solutol HS 15 + 80% Saline

| Formulation | Cmax (ng/mL) | t½ (h) | AUC (h*ng/ml) | F (%) |
|---|---|---|---|---|
| Example 1 | 92.8 | 2.06 | 190.10 | 21.90% |

Conclusion: Examples 1 and 4 have good Pharmacokinetic profile in rats.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the structural formula (I):

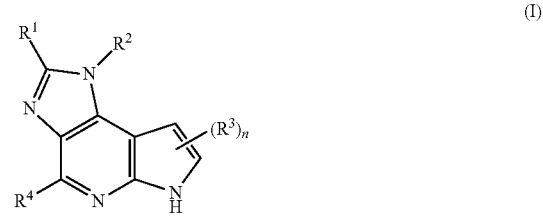

wherein
$R^1$ is H;
$R^2$ is

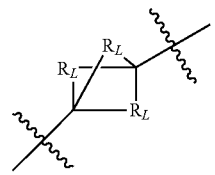

wherein each $R_L$ is $(CH_2)_m$ and m is 1, and wherein $R^2$ is substituted at an open

position with $NR'C(=O)R^x$, $NR'C(=O)OR^x$, or $NR'C(=O)NR^xR^y$;

$R^3$ is H;
$R^4$ is H;
each of $R^x$ and $R^y$ is independently selected from H, alkyl, cycloalkyl, heterocycloalkyl, aryl, heteroaryl and $R^x$ and $R^y$ may together form a 4- or 5-membered ring, and each of $R^x$ and $R^y$ is optionally substituted with one or more of halogen, CN, OR', NR'R", alkyl, haloalkyl, cyanoalkyl, hydroxyalkyl and alkoxyalkyl;
each of R' and R" is independently selected from hydrogen and $C_1$-$C_6$ alkyl; and
n is 1,
or a pharmaceutically acceptable salt thereof.

2. The compound of claim 1, wherein $R^2$ is substituted at the open

position with NR'C(=O)$R^x$.

3. The compound of claim 1, wherein $R^2$ is substituted at the open

position with NR'C(=O)O$R^x$.

4. The compound of claim 1, wherein $R^2$ is substituted at the open

position with NR'C(=O)N$R^x R^y$.

5. The compound of claim 1, selected from:

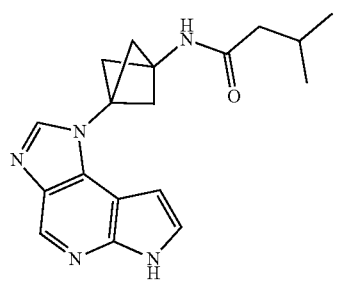

8

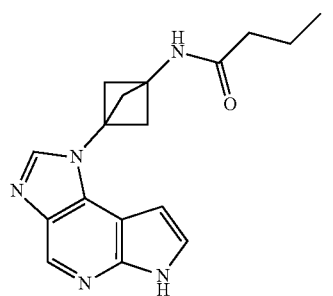

9

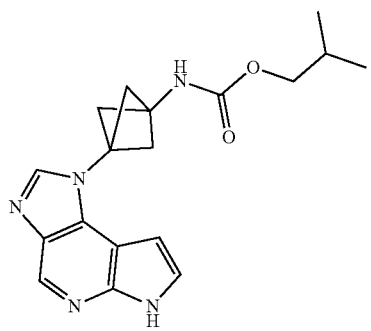

10

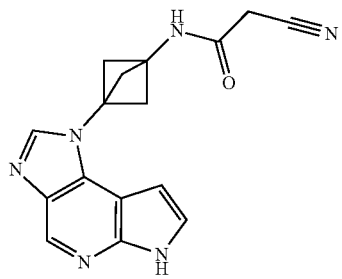

11

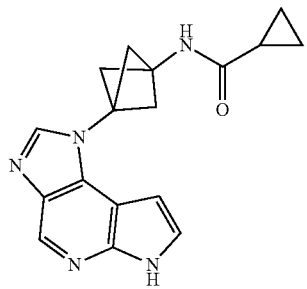

12

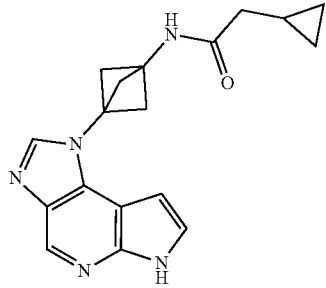

13

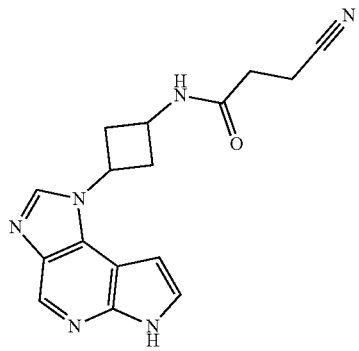

14

-continued
15
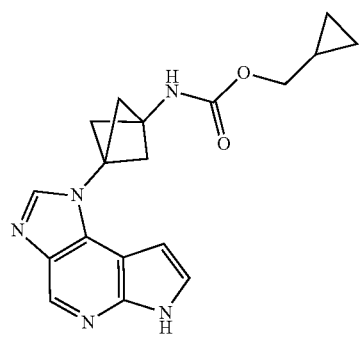
19
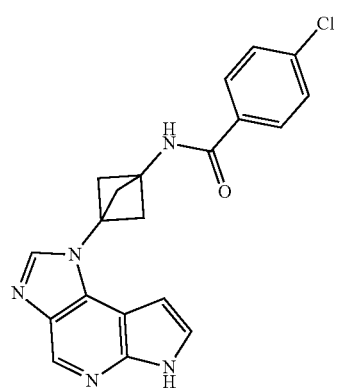
5
10
15
16
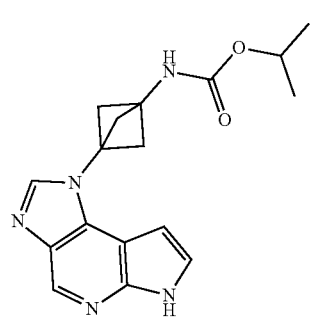
20
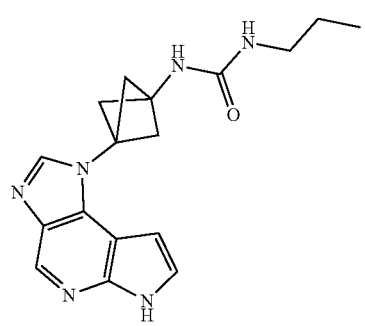
34
25
17
30
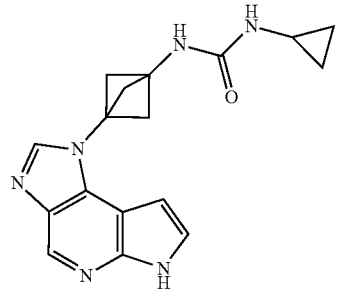
35
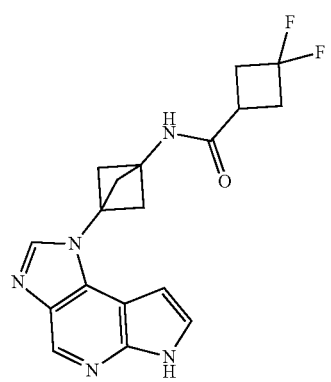
35
40
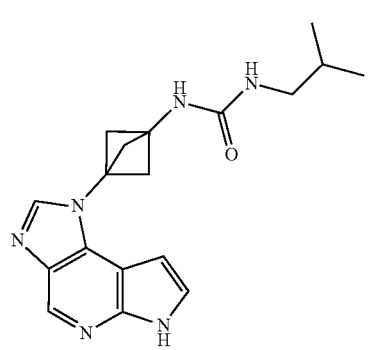
36
45
50
18
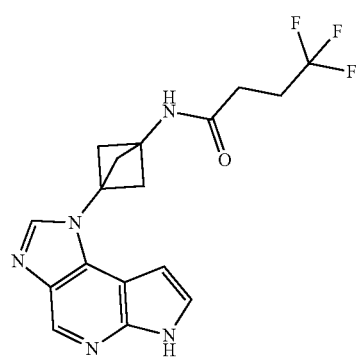
55
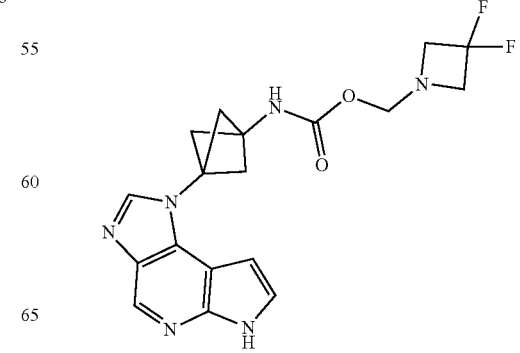
37
60
65

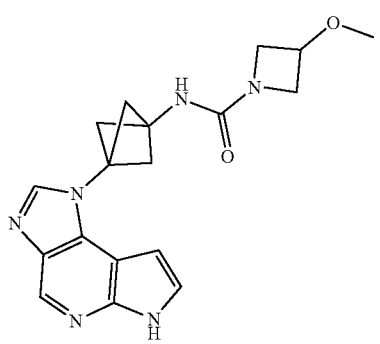
38
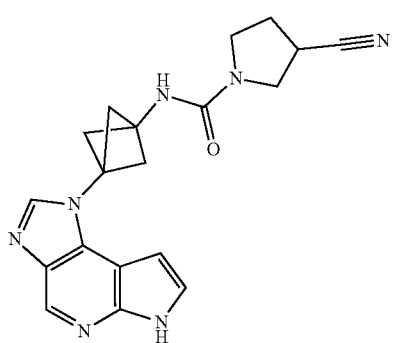
39
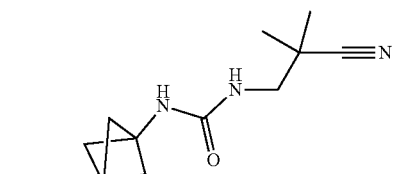
40
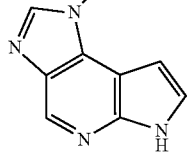
41
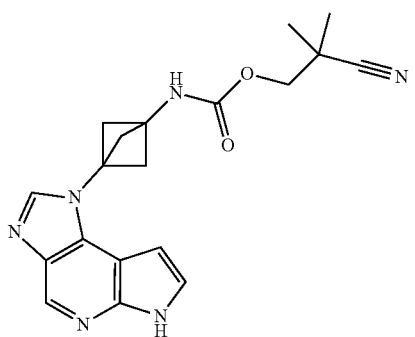
42
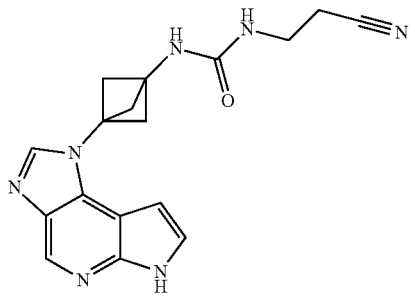
43
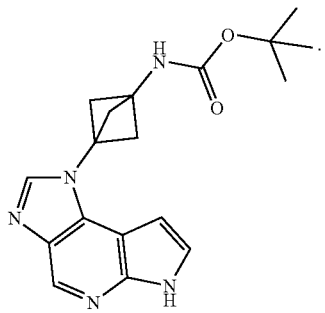
1i
6. The compound of claim 5, selected from:
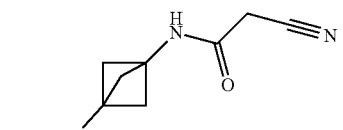
11
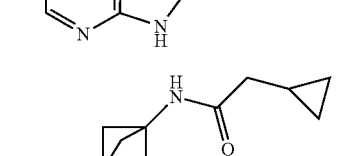
13

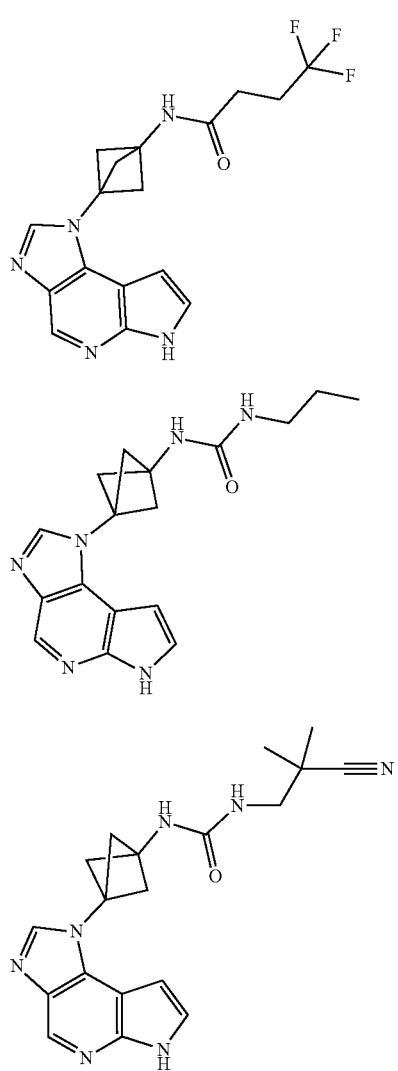
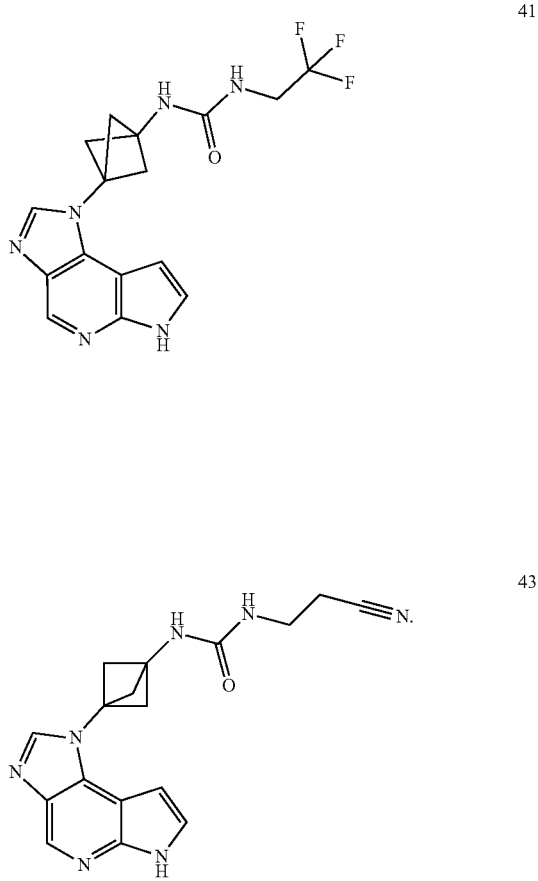
7. A pharmaceutical composition comprising a compound according to claim 1 and a pharmaceutically acceptable excipient, carrier, or diluent.
8. A pharmaceutical composition comprising a compound of claim 5.
\* \* \* \* \*